US005968907A

United States Patent [19]

Hindsgaul

[11] Patent Number: 5,968,907
[45] Date of Patent: *Oct. 19, 1999

[54] 1-THIOGALACTOSE DERIVATIVES

[75] Inventor: Ole Hindsgaul, Edmonton, Canada

[73] Assignee: Synsorb Biotech, Inc., Calgary, Canada

[*] Notice: This patent is subject to a terminal disclaimer.

[21] Appl. No.: 08/970,384

[22] Filed: Nov. 14, 1997

Related U.S. Application Data

[63] Continuation-in-part of application No. 08/751,510, Nov. 15, 1996, Pat. No. 5,780,603
[60] Provisional application No. 60/030,794, Nov. 14, 1996.
[51] Int. Cl.$^6$ .......................... A61K 31/70; C07H 15/24
[52] U.S. Cl. ............................ 514/24; 536/4.1; 536/17.6
[58] Field of Search ................................ 514/24; 536/4.1, 536/18.5, 18.6, 17.6

[56] References Cited

U.S. PATENT DOCUMENTS

| 4,137,401 | 1/1979 | Lemieux et al. ............ 536/116 |
| 5,580,858 | 12/1996 | Ippolito et al. ............ 514/25 |
| 5,780,603 | 7/1998 | Hindsgaul ............ 536/4.1 |

FOREIGN PATENT DOCUMENTS

| 0 649 021 A1 | 4/1995 | European Pat. Off. . |
| WO 94/19360 | 9/1994 | WIPO . |
| WO 95/21628 | 8/1995 | WIPO . |

OTHER PUBLICATIONS

J. Defaye, et al., "Thiooligosaccharides: Their Synthesis and Reactions with Enzymes" in *Studies in Natural Products Chemistry*, vol. 8, pp. 315–357, Elsevier Sciences Publishers (1991).
Collins et al., "Monosaccharides: Their Chemistry and Their Roles in Natural Products," John Wiley & Sons, Chichester, England, 1995, pp. 97–106.
Ferrier et al., *Carbohydrate Chemistry* 1996, 28, 158–164.
Ferrier et al., *Carbohydrate Chemistry* 1993, 27, 140–147.
Williams et al., *Carbohydrate Chemistry* 1983, 17, 116–119.
Horton et al., Thio Sugars and Derivatives, In "The Carbohydrates: Chemistry and Biochemistry", 2$^{nd}$ Edition, Pigman et al., eds. Academic Press, New York, 1980.
Schnabeirauch et al, *Helv. Chim. Acta* 1994, 77, 778.
Spangler, B.D., "Structure and Function of Cholera Toxin and Related *Escherichia coli* Heat–Labile Enterotoxin", *Microbiological Reviews*, 56 (4):622–647 (1992).
Hol, W.G.J., et al., "Structure and Function of *E. coli* Heat–Labile Enteerotoxin and Cholera Toxin B Pentamer", *Bacterial Toxins and Virulence Factors in Disease*, Ed. by J. Moss et al., Marcel Dekker, Inc. (1995).

Evans et al., *J. Amer. Chem. Soc.*, 112:4011–4030 (1990).
Pu et al., *J. Org. Chem.*, 56:1280–1283 (1991).
Williams et al., *J. Amer. Chem Soc.*, 113:9276–9286 (1991).
Kagen et al., *Synlett*, 1990, 643–650.
E. Hasegawa, K. Ishiyama, T. Horaguchi, T. Shimizu, *J. Org. Chem.*, 1991, 56, 1631–1635.
H. Paulsen, K.Eberstein, W. Koebernick, *Tetrahedron Letters*, 1974, 4377–4380.
M. Dubois et al., *Anal. Chem.*, 28, (1979) 350–356.
T. Mukaiyama et al., *Tetrahedron Letters*, 56, 5907–5908 (1968).
H. H. Westal et al., "Methods of Enzymology,"34(b), 64 (1974).
Svennerholm, A–M. et al., *Current Microbiology*, 1:19–23 (1978).
A. Hasagawa et al., *J. Carbohydrate Chem.*, 5, 11–19 (1986).
D.W.K. Acheson et al., *Infect. Immun.*, 61 (3), 1098–1104 (1993).
A. Ramesh et al., *J. Biotechol.*, 43 (1), 45–51–(1995).
P. Fugedi et al., *Glycoconjugate Journal*, 4, 97–100 (1987).
E. Bar–Guilloux et al., *Carbohydrate Research*, 250 (1), 1–8 (1993).
M. Cerny et al., *Collection of Czechoslovak Chemical Communications*, 61 (10), 1489–1500 (1996).
G. Vic et al., *Tetrahedron: Asymmetry*, 5 (12), 2513–1516 (1994).
J. DeFaye et al., *Carbohydrate Research*, 253, 185–194 (1994).
I. Tvaroska et al., *Carbohydrate Research*, 229 (2), 225–231 (1992).
M.–O. Contour–Galcera et al. *Carbohydrate Research*, 281 (1), 99–118 (1996).
M. Petrusova et al., *Carbohydrate Research*, 283, 73–80 (1996).
Witczak, Z.J. et al., Synthesis of L–Fucopyranosyl, 4–Thiodisacchasrides from Levoglucosenone and Their Inhibitory Activity on α–L–Fucosidase, "Bioorganic & Medicinal Chemistry Letters", vol. 5, No. 18:2169–2174, 1995.

*Primary Examiner*—Elli Peselev
*Attorney, Agent, or Firm*—Burns, Doane, Swecker & Mathis, LLP

[57] ABSTRACT

Disclosed are novel 1-thiogalactose derivatives which inhibit binding of toxins, such as heat-labile enterotoxin or cholera toxin, to their receptors either in vitro or in vivo. Additionally, disclosed are compounds which inhibit binding of organisms (e.g., bacteria, virus, fungi, and the like), such as *Vibrio cholerae* and enterotoxigenic strains of *Escherichia coli*, to their cell surface receptors.

87 Claims, 2 Drawing Sheets

1-THIOGALACTOSE DERIVATIVES

CROSS-REFERENCE TO RELATED APPLICATIONS

This application is a continuation-in-part of U.S. Ser. No. 08/751,510, filed Nov. 15, 1996, now U.S. Pat. No. 5,780,603, which application claims the benefit of U.S. Provisional Application No. 60/030,794, filed Nov. 14, 1996, which applications are incorporated herein by reference in their entirety.

BACKGROUND OF THE INVENTION

1. Field of the Invention

This invention relates to novel 1-thiogalactose derivatives which inhibit binding of toxins, such as heat-labile enterotoxin (LT) or cholera toxin (CT), to their receptors either in vitro or in vivo. Additionally, the compounds of this invention inhibit binding of organisms (e.g., bacteria, virus, fungi, and the like), such as *Vibrio cholerae* and enterotoxigenic strains of *Escherichia coli*, to their cell surface receptors.

References

The following publications, patents and patent applications are cited in this application as superscript numbers:

1. Spangler, B. D., "Structure and Function of Cholera Toxin and Related *Escherichia coli* Heat-Labile Enterotoxin", *Microbiological Reviews*, 56(4): 622–647 (1992).
2. Hol, W. G. J., et al., "Structure and Function of *E. coli* Heat-Labile Enterotoxin and Cholera Toxin B Pentamer", *Bacterial Toxins and Virulence Factors in Disease*, Ed. by J. Moss et al., Marcel Dekker, Inc. (1995).
3. Williams (ed.), *Synthesis of Optically Active α-Amino Acids*, Pergamon Press (1989).
4. Evans et al., *J. Amer. Chem. Soc.*, 112: 4011–4030 (1990).
5. Pu et al., *J. Amer. Chem. Soc.*, 56: 1280–1283 (1991).
6. Williams et al., *J. Amer. Chem. Soc.*, 113: 9276–9286 (1991).
7. Kagen et al., *Synlett*, 1990, 643–650.
8. U.S. Pat. No. 5,580,858, issued Dec. 3, 1996, to R. M. Ippolito et al.
9. M. Dubois et al., *Anal. Chem.*, 28, (1979) 350–356.
10. U.S. Pat. No. 4,137,401, issued Jan. 30, 1979, to R. Lemieux et al.
11. H. H. Westal et al., "Methods of Enzymology," 34(b), 64 (1974).
12. T. Mukaiyama et al., *Tetrahedron Letters*, 56, 5907–5908 (1968).
13. Svennerholm, A-M. et al., *Current Microbiology*, 1: 19–23 (1978).

All of the above publications, patents and patent applications are herein incorporated by reference in their entirety to the same extent as if each individual publication, patent or patent application was specifically and individually indicated to be incorporated by reference in its entirety.

2. State of the Art

Toxins produced by organisms, such as bacteria, viruses, protozoa, fungi and other organisms, are known to cause a number of animal and human diseases, including many diarrheal diseases. For example, heat-labile enterotoxin ("LT"), secreted by certain enterotoxigenic strains of *Escherichia coli*, has been identified as one of the causative agents of bacterial-induced traveller's diarrhea.[1] Additionally, cholera toxin ("CT"), produced by *Vibrio cholerae*, has been identified as the causative agent of the severe diarrheal disease, cholera.[1]

Heat-labile enterotoxin and cholera toxin are known to bind to oligosaccharide receptors on host cells as an initial step in the pathological development of the associated disease condition.[2] Specifically, both LT and CT are known to bind to ganglioside $G_{M1}$, a glycosphingolipid situated in the outer leaflet of the host cell membrane.[2] $G_{M1}$ has a characteristic pentasaccharide structure, i.e., Gal(β1→3)GalNAc(β1→4){NeuAc(α2→3)}Gal(β1→4)Glc, on its surface which serves as a receptor for LT and CT. LT is also known to bind to other gangliosides, such as ganglioside $G_{D1b}$.

Additionally, many virulent organisms (e.g., bacteria, virus, fungi, and the like) including enterovirulent organisms bind to cell surface receptors as part of the disease process. For example, bacteria such as *Vibrio cholerae* and enterotoxigenic strains of *Escherichia coli* can directly bind to cell surface receptors forming a colony at the point of attachment. Such binding is detrimental because it permits expressed toxin to immediately interact with the cell surface.

In order to ameliorate or prevent the noxious or deleterious effects caused by toxins and organisms, it would be highly desirable to be able to inhibit the binding of the toxin or the organism to its corresponding cell surface receptor. The present invention provides novel 1-thiogalactose derivatives which effectively inhibit such binding.

SUMMARY OF THE INVENTION

This invention is directed to the discovery of a novel class of 1-thiogalactose derivatives which inhibit the binding of toxins, such as heat-labile enterotoxin (LT) or cholera toxin (CT), to their receptors. The compounds of this invention also inhibit binding of organisms, such as *Vibrio cholerae* and enterotoxigenic strains of *Escherichia coli*, to their cell surface receptors.

Accordingly, in one of its composition aspects, this invention provides compounds of formula I:

wherein $R^1$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;

$R^2$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;

$R^3$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;

or $R^1$ and $R^2$, or $R^1$ and $R^3$, or $R^2$ and $R^3$, or $R^1$, $R^2$ and $R^3$ can be joined, together with the carbon atoms to which $R^1$ and/or $R^2$ and/or $R^3$ are attached, to form a cycloalkyl, cycloalkenyl or heterocyclic ring;

$R^4$ is selected from the group consisting of $—XR^5$, $—XC(W)R^6$, $—XC(W)X'R^7$ and $—C(W)XR^8$; wherein W is selected from the group consisting of oxygen, sulfur and NH; and X and X' are each independently selected from the group consisting of oxygen, sulfur and $—NR^9—$, wherein $R^9$ is selected from the group consisting of hydrogen and alkyl; or when $R^4$ is $—XR^5$ and $R^5$ is not hydrogen, X can also be selected from the group consisting of $—S(O)—$ and $—SO_2—$;

$R^5$ is selected from the group consisting of hydrogen, alkyl, alkenyl, alkaryl, alkoxyalkyl, aryl, cycloalkyl, cycloalkenyl, heteroaryl, heterocyclic and thioalkoxyalkyl, and when X is $—NR^9—$, then $R^9$ together with X can form an amino acid; or $R^5$ and $R^1$, or $R^5$ and $R^2$, or $R^5$ and $R^3$ can be joined, together with X of the $— XR^5$ group and the carbon atoms to which $R^1$ and/or $R^2$ and/or $R^3$ are attached, to form a heterocyclic ring;

$R^6$ is selected from the group consisting of alkyl, alkenyl, alkaryl, alkoxyalkyl, aryl, cycloalkyl, cycloalkenyl, heteroaryl, heterocyclic and thioalkoxyalkyl; or $R^6$ and $R^1$, or $R^6$ and $R^2$, or $R^6$ and $R^3$ can be joined, together with the $—XC(W)—$ moiety of the $—XC(W)R^6$ group and the carbon atoms to which $R^1$ and/or $R^2$ and/or $R^3$ are attached, to form a heterocyclic ring;

$R^7$ is selected from the group consisting of alkyl, alkenyl, alkaryl, alkoxyalkyl, aryl, cycloalkyl, cycloalkenyl, heteroaryl, heterocyclic and thioalkoxyalkyl; or $R^7$ and $R^1$, or $R^7$ and $R^2$, or $R^7$ and $R^3$ can be joined, together with the $—XC(W)X'—$ moiety of the $—XC(W)X'R^7$ group and the carbon atoms to which $R^1$ and/or $R^2$ and/or $R^3$ are attached, to form a heterocyclic ring;

$R^8$ is selected from the group consisting of alkyl, alkenyl, alkaryl, alkoxyalkyl, aryl, cycloalkyl, cycloalkenyl, heteroaryl, heterocyclic and thioalkoxyalkyl; or $R^8$ and $R^1$, or $R^8$ and $R^2$, or $R^8$ and $R^3$ can be joined, together with the $—C(W)X—$ moiety of the $—C(W)XR^8$ group and the carbon atoms to which $R^1$, $R^2$ and/or $R^3$ are attached, to form a heterocyclic ring;

Y is selected from the group consisting of sulfur, $—S(O)—$ and $—S(O)_2—$;

$R^a$, $R^b$, $R^c$ and $R^d$ are each independently selected from the group consisting of hydrogen; sulfate; $—C(O)R^{10}$, wherein $R^{10}$ is selected from the group consisting of alkyl, alkenyl, alkaryl, alkoxyalkyl, aryl, cycloalkyl, cycloalkenyl, heteroaryl, heterocyclic and thioalkoxyalkyl; and $—P(O)(OR^{11})_2$, wherein each $R^{11}$ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl;

n is an integer equal to 0 or 1; and pharmaceutically acceptable salts thereof;

with the proviso that when $R^1$ and $R^2$ are joined, together with the carbon atoms to which $R^1$, $R^2$ and $R^3$ are attached, to form a cyclopentyl ring, $R^3$ is hydrogen, $R^4$ is $—XR^5$, X is oxygen, Y is sulfur, $R^a$, $R^b$, $R^c$ and $R^d$ are each hydrogen and n is 1, then $R^5$ is not hydrogen.

In one preferred embodiment, the present invention is directed to the α-anomers of compounds of formula I. In another preferred embodiment, this invention is directed to the β-anomers of compounds of formula I.

Preferably, $R^1$, $R^2$, $R^3$, $R^5$, $R^6$, $R^7$ and $R^8$ in formula I above are selected so as to form at least one carbocyclic (i.e., cycloalkyl or cycloalkenyl) or heterocyclic ring. More preferably, $R^1$, $R^2$, $R^3$, $R^5$, $R^6$, $R^7$ and $R^8$ are selected so as to form two carbocyclic or heterocyclic rings.

In formula I above, when n is 0, $R^1$ and $R^2$ are preferably joined, together with the carbon to which they are attached, to form a cycloalkyl ring having 5 to 7 carbon atoms optionally substituted with 1 to 3 alkyl groups. More preferably, $R^1$ and $R^2$ are joined, together with the carbon to which they are attached, to form a cyclopentane or cyclohexane ring.

When n is 1, $R^1$ and $R^2$ are preferably joined, together with the carbon atoms to which $R^1$, $R^2$ and $R^3$ are attached, to form a cycloalkyl ring having 5 to 7 carbon atoms optionally substituted with 1 to 3 alkyl groups. More preferably, $R^1$ and $R^2$ are joined, together with the carbon atoms to which $R^1$, $R^2$ and $R^3$ are attached, to form a cyclopentane, dimethylcyclopentane, cyclohexane, dimethylcyclohexane or cycloheptane ring.

Alternatively, $R^2$ and $R^3$ are preferably joined, together with the carbon atoms to which they are attached, to form a norbornene ring (i.e., a bicyclo[2.2.1]heptane ring).

When $R^3$ is not joined with $R^2$ to form a cycloalkyl ring, $R^3$ is preferably hydrogen.

Preferred $R^4$ groups include, by way of example, those having the formula $—XR^5$ where X and $R^5$ form an amino group, a hydroxy group or an amino acid selected from the group consisting of glycine, β-alanine, leucine, histidine, tryptophan and arginine; or those having the formula $—XR^5$ where X is $—NH—$ and $R^5$ is alkyl; or those having the formula $—XR^5$ where X is $—NH—$ and $R^5$ is cycloalkyl; or those having the formula $—XC(O)R^6$ where X is $—NH—$ and $R^6$ is methyl or 2-carboxyphenyl. When $R^4$ is $—XR^5$ where X is $—NH—$ and $R^5$ is alkyl, the alkyl group is preferably a methyl, isopropyl, n-propyl, sec-butyl, pent-3-yl, or n-hexyl group. Additionally, when $R^4$ is $—XR^5$ where X is $—NH—$ and $R^5$ is cycloalkyl, the cycloalkyl group is preferably a cyclobutyl, dimethylcyclobutyl, cyclopentyl, methylcyclopentyl, dimethylcyclopentyl, cyclohexyl, methylcyclohexyl or dimethylcyclohexyl group.

Preferably, $R^a$, $R^b$, $R^c$ and $R^d$ are each independently selected from the group consisting of hydrogen and $—C(O)R^{10}$, where $R^{10}$ is alkyl. More preferably, $R^a$, $R^b$, $R^c$ and $R^d$ are each hydrogen.

Particularly preferred compounds provided by this invention include, by way of example, the following:

2-hydroxycyclopent-1-yl 1-thio-β-D-galactopyranoside
2-hydroxycyclohex-1-yl 1-thio-β-D-galactopyranoside
3-hydroxy-1-phenylbut-1-yl 1-thio-β-D-galactopyranoside
(3-hydroxynorborn-2-yl)methyl 1-thio-β-D-galactopyranoside
3-hydroxycyclohept-1-yl 1-thio-β-D-galactopyranoside
3-hydroxycyclohept-1-yl 1-thio-β-D-galactopyranoside
2,2-dimethyl-4-hydroxycyclopent-1-yl 1-thio-α-D-galactopyranoside
4-hydroxypent-2-yl 1-thio-β-D-galactopyranoside
2,2-dimethyl-5-hydroxycyclohex-1-yl 1-thio-β-D-galactopyranoside
3-hydroxycyclohex-1-yl 1-thio-β-D-galactopyranoside
4,4-dimethyl-3-hydroxycyclohex-1-yl 1-thio-β-D-galactopyranoside
2-aminocyclopent-1-yl 1-thio-β-D-galactopyranoside
2-aminocyclohex-1-yl 1-thio-β-D-galactopyranoside
3-amino-1-phenylbut-1-yl 1-thio-β-D-galactopyranoside
(3-aminonorborn-2-yl)methyl 1-thio-β-D-galactopyranoside
3-aminocyclohept-1-yl 1-thio-β-D-galactopyranoside
2,2-dimethyl-4-aminocyclopent-1-yl 1-thio-β-D-galactopyranoside
3-aminocyclopent-1-yl 1-thio-β-D-galactopyranoside
4-aminopent-2-yl 1-thio-β-D-galactopyranoside
3-aminocyclohex-1-yl 1-thio-β-D-galactopyranoside
3-amino-4,4-dimethylcyclohex-1-yl 1-thio-β-D-galactopyranoside 2-acetamidocyclopent-1-yl 1-thio-β-D-galactopyranoside
2-acetamidocyclohex-1-yl 1-thio-β-D-galactopyranoside
3-acetamido-1-phenylbut-1-yl 1-thio-β-D-galactopyranoside
3-acetamidocyclohept-1-yl 1-thio-β-D-galactopyranoside
3-acetamidocyclopent-1-yl 1-thio-β-D-galactopyranoside
4-acetamidopent-2-yl 1-thio-β-D-galactopyranoside
3-acetamidocyclohexyl 1-thio-β-D-galactopyranoside
3-acetamido-4,4-dimethylcyclohexyl 1-thio-β-D-galactopyranoside
2-(2-carboxybenzamido)cyclopent-1-yl 1-thio-β-D-galactopyranoside
2-(2-carboxybenzamido)cyclohex-1-yl 1-thio-β-D-galactopyranoside
3-(2-carboxybenzamido)-1-phenylbut-1-yl 1-thio-β-D-galactopyranoside
[3-(carboxybenzamido)norborn-2-yl]methyl 1-thio-β-D-galactopyranoside
3-(2-carboxybenzamido)cyclohept-1-yl 1-thio-β-D-galactopyranoside
3-(2-carboxybenzamido)pent-2-yl 1-thio-β-D-galactopyranoside
5-(2-carboxybenzamido)-2,2-dimethylcyclohex-1-yl 1-thio-β-D-galactopyranoside
3-(2-carboxybenzamido)cyclohex-1-yl 1-thio-β-D-galactopyranoside
Nα-[2-(1-thio-β-D-galactopyranosyl)cyclopent-1-yl]glycin
Nα-[2-(1-thio-β-D-galactopyranosyl)cyclopent-1-yl]glycin
Nα-[4-phenyl-4-(1-thio-β-D-galactopyranosyl)but-2-yl]glycine
Nα-[3-((1-thio-β-D-galactopyranosyl)methyl)norbom-2-yl]glycine
Nα-[3-(1-thio-β-D-galactopyranosyl)cyclohept-1-yl]glycine
Nα-[3-(1-thio-α-D-galactopyranosyl)cyclohept-1-yl]glycine
Nα-[4,4-dimethyl-3-(1-thio-β-D-galactopyranosyl)cyclopent-1-yl]glycine
Nα-[3-(1-thio-β-D-galactopyranosyl)cyclopent-1-yl]glycine
Nα-[4-(1-thio-β-D-galactopyranosyl)pent-2-yl]glycine
Nα-[4,4-dimethyl-3-(1-thio-β-D-galactopyranosyl)cyclohex-1-yl]glycine
Nα-[3-(1-thio-β-D-galactopyranosyl)cyclohex-1-yl]glycine
Nα-[5-(1-thio-β-D-galactopyranosyl)-2,2-dimethylcyclohex-1-yl]glycine
Nβ-[2-(1-thio-β-D-galactopyranosyl)cyclopent-1-yl]-β-alanine
Nβ-[2-(1-thio-β-D-galactopyranosyl)cyclohex-1-yl]-β-alanine
Nβ-[4-phenyl-4-(1-thio-β-D-galactopyranosyl)but-2-yl]-β-alanine
Nβ-[3-((1-thio-β-D-galactopyranosyl) methyl)norborn-2-yl]-β-alanine
Nβ-[3-(1-thio-β-D-galactopyranosyl)cyclohept-1-yl]-β-alanine
Nβ-[4,4-dimethyl-3-(1-thio-β-D-galactopyranosyl)cyclopent-1-yl]-β-alanine
Nβ-[3-(1-thio-β-D-galactopyranosyl)cyclopent-1-yl]-β-alanine
Nβ-[4-(1-thio-β-D-galactopyranosyl)pent-2-yl]-β-alanine
Nβ-[4,4-dimethyl-3-(1-thio-β-D-galactopyranosyl)cyclohex-1-yl]-β-alanine
Nβ-[3-(1-thio-β-D-galactopyranosyl)cyclohex-1-yl]-β-alanine
Nβ-[5-(1-thio-β-D-galactopyranosyl)-2,2-dimethylcyclohex-1-yl]-β-alanine
Nα-[2-(1-thio-β-D-galactopyranosyl)cyclopent-1-yl]-L-leucine
Nα-[2-(1-thio-β-D-galactopyranosyl)cyclohex-1-yl]-L-leucine
Nα-[4-phenyl-4-(1-thio-β-D-galactopyranosyl)but-2-yl]-L-leucine
Nα-[1-(1-thio-β-D-galactopyranosyl)cyclohept-3-yl]-L-leucine
Nα-[4,4-dimethyl-3-(1-thio-β-D-galactopyranosyl)cyclopent-1-yl]-L-leucine
Nα-[3-(1-thio-β-D-galactopyranosyl)cyclopent-1-yl]-L-leucine
Nα-[4-(1-thio-β-D-galactopyranosyl)pent-2-yl]-L-leucine
Nα-[4,4-dimethyl-3-(1-thio-β-D-galactopyranosyl)cyclohex-1-yl]-L-leucine
Nα-[3-(1-thio-β-D-galactopyranosyl)cyclohex-1-yl]-L-leucine
Nα-[2-(1-thio-β-D-galactopyranosyl)cyclopent-1-yl]-L-histidine
Nα-[2-(1-thio-β-D-galactopyranosyl)cyclohex-1-yi]-L-histidine
Nα-[4-phenyl-4-(1-thio-β-D-galactopyranosyl)but-2-yl]-L-histidine
Nα-[3-(1-thio-β-D-galactopyranosyl)cyclohept-1-yl]-L-histidine
Nα-[4,4-dimethyl-3-(1-thio-β-D-galactopyranosyl)cyclopent-1-yl]-L-histidine
Nα-[3-(1-thio-β-D-galactopyranosyl)cyclopent-1-yl]-L-histidine
Nα-[4-(1-thio-β-D-galactopyranosyl)pent-2-yl]-L-histidine
Nα-[4,4-dimethyl-3-(1-thio-β-D-galactopyranosyl)cyclohex-1-yl]-L-histidine
Nα-[3-(1-thio-α-D-galactopyranosyl)cyclohex-1-yl]-L-histidine
Nα-[2-(1-thio-α-D-galactopyranosyl)cyclopent-1-yl]-L-tryptophan
Nα-[2-(1-thio-β-D-galactopyranosyl)cyclohex-1-yl]-L-tryptophan
Nα-[4-phenyl-4-(1-thio-β-D-galactopyranosyl)but-2-yl]-L-tryptophan
Nα-[3-(1-thio-β-D-galactopyranosyl)cyclohept-1-yl]-L-tryptophan
Nα-[4,4-dimethyl-3-(1-thio-β-D-galactopyranosyl)cyclopent-1-yl]-L-tryptophan
Nα-[3-(1-thio-β-D-galactopyranosyl)cyclopent-1-yl]-L-tryptophan
Nα-[4-(1-thio-β-D-galactopyranosyl)pent-2-yl]-L-tryptophan
Nα-[4,4-dimethyl-3-(1-thio-β-D-galactopyranosyl)cyclohex-1-yl]-L-tryptophan
Nα-[3-(1-thio-β-D-galactopyranosyl)cyclohex-1-yl]-L-tryptophan
Nα-[2-(1-thio-β-D-galactopyranosyl)cyclopent-1-yl]-L-arginine
Nα-[2-(1-thio-β-D-galactopyranosyl)cyclohex-1-yl]-L-arginine
Nα-[4-phenyl-4-(1-thio-β-D-galactopyranosyl)but-2-yl]-L-arginine
Nα-[3-(1-thio-β-D-galactopyranosyl)cyclohept-1-yl]-L-arginine
Nα-[4,4-dimethyl-3-(1-thio-β-D-galactopyranosyl)cyclopent-1-yl]-L-arginine
Nα-[3-(1-thio-β-D-galactopyranosyl)cyclopent-1-yl]-L-arginine
Nα-[4-(1-thio-β-D-galactopyranosyl)pent-2-yl]-L-arginine
Nα-[4,4-dimethyl-3-(1-thio-β-D-galactopyranosyl)cyclohex-1-yl]-L-arginine Nα-[3-(1-thio-β-D-galactopyranosyl)cyclohex-1-yl]-L-arginine
2,2-dimethyl-4-(methylamino)cyclopent-1-yl 1-thio-β-D-galactopyranoside
2,2-dimethyl-4-(isopropylamino)cyclopent-1-yl 1-thio-β-D-galactopyranoside
2,2-dimethyl-4-(n-propylamino)cyclopent-1-yl 1-thio-β-D-galactopyranoside
2,2-dimethyl-4-((R)-sec-butylamino)cyclopent-1-yl 1-thio-β-D-galactopyranoside
2,2-dimethyl-4-((S)-sec-butylamino)cyclopent-1-yl 1-thio-β-D-galactopyranoside
2,2-dimethyl-4-(pent-3-ylamino)cyclopent-1-yl 1-thio-β-D-galactopyranoside
2,2-dimethyl-4-(n-hexylamino)cyclopent-1-yl 1-thio-β-D-galactopyranoside
2,2-dimethyl-4-(cyclobutylamino)cyclopent-1-yl 1-thioβ-D-galactopyranoside
2,2-dimethyl-4-(3,3-dimethylcyclobut-1-ylamino)cyclopent-1-yl 1-thio-β-D-galactopyranoside
2,2-dimethyl-4-(cyclopentylamino)cyclopent-1-yl 1-thio-β-D-galactopyranoside
2,2-dimethyl-4-(3-methylcyclopent-1-ylamino)cyclopent-1-yl 1-thio-β-D-galactopyranoside
2,2-dimethyl-4-(3,3-dimethylcyclopent-1-ylamino)cyclopent-1-yl 1-thio-β-D-galactopyranoside
2,2-dimethyl-4-(cyclohexylamino)cyclopent-1-yl 1-thio-β-D-galactopyranoside
2,2-dimethyl-4-(3-methylcyclohex-1-ylamino)cyclopent-1-yl 1-thio-β-D-galactopyranoside
2,2-dimethyl-4-(4-methylcyclohex-1-ylamino)cyclopent-1-yl 1-thio-β-D-galactopyranoside
and pharmaceutically acceptable salts thereof.

In another of its composition aspects, this invention provides a compound of formula I above, wherein said compound of formula I inhibits the binding of a toxin, preferably heat-labile enterotoxin or cholera toxin, to its receptor, or said compound inhibits the binding of an organism to a cell surface receptor.

In yet another of its composition aspects, this invention provides a pharmaceutical composition comprising from 1 to 99 weight percent of a pharmaceutically acceptable carrier and from 1 to 99 weight percent of at least one compound of formula I above.

In one of its method aspects, this invention is directed to a method of ameliorating conditions associated with binding of a toxin to its receptor in an animal which method comprises administering to said animal an effective amount of a pharmaceutical composition comprising from 1 to 99 weight percent of a pharmaceutically acceptable carrier and from 1 to 99 weight percent of at least one compound of formula I above, wherein the compound of formula I inhibits the binding of the toxin to its receptor.

In preferred embodiments of this invention, the toxin in the above method is heat-labile enterotoxin or cholera toxin.

In another of its method aspects, this invention is directed to a method of ameliorating conditions associated with binding of an organism to its cell surface receptor in an animal which method comprises administering to said animal an effective amount of a pharmaceutical composition comprising from 1 to 99 weight percent of a pharmaceutically acceptable carrier and from 1 to 99 weight percent of at least one compound of formula I above, wherein the compound of formula I inhibits the binding of the organism to its cell surface receptor.

In preferred embodiments of this invention, the organism in the above method is *Vibrio cholerae* or an enterotoxigenic strain of *Escherichia coli*.

This invention is also directed to 1-thiogalactose derivative-containing supports which are useful for inhibiting the binding of a toxin to its receptor. Supports useful for inhibiting the binding of an organism to its cell surface receptor are also provided.

Accordingly, in yet another of its composition aspects, this invention provides a 1-thiogalactose derivative-containing support comprising a support having covalently bound thereto a plurality of at least one compound of formula I':

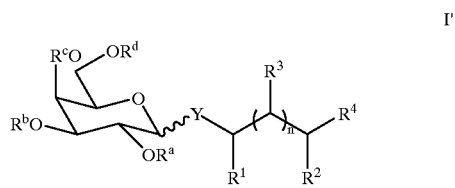

wherein $R^1$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support;

$R^2$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support;

$R^3$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support;

or $R^1$ and $R^2$, or $R^1$ and $R^3$, or $R^2$ and $R^3$, or $R^1$, $R^2$ and $R^3$ can be joined, together with the carbon atoms to which $R^1$ and/or $R^2$ and/or $R^3$ are attached, to form a cycloalkyl, cycloalkenyl or heterocyclic ring;

$R^4$ is selected from the group consisting of —$XR^5$, —$XC(W)R^6$, —$XC(W)X'R^7$ and —$C(W)XR^8$; wherein W is selected from the group consisting of oxygen, sulfur and NH; and X and X' are each independently selected from the group consisting of oxygen, sulfur and —$NR^9$—, wherein $R^9$ is selected from the group consisting of hydrogen and alkyl; or when $R^4$ is —$XR^5$ and $R^5$ is not hydrogen, X can also be selected from the group consisting of —S(O)— and —$SO_2$—;

$R^5$ is selected from the group consisting of hydrogen, alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support, and when X is —$NR^9$—, then $R^9$ together with X can form an amino acid; or $R^5$ and $R^1$, or $R^5$ and $R^2$, or $R^5$ and $R^3$ can be joined, together with X of the —$XR^5$ group and the carbon atoms to which $R^1$ and/or $R^2$ and/or $R^3$ are attached, to form a heterocyclic ring;

$R^6$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^6$ and $R^1$, or $R^6$ and $R^2$, or $R^6$ and $R^3$ can be joined, together with the —XC(W)— moiety of the —$XC(W)R^6$ group and the carbon atoms to which $R^1$ and/or $R^2$ and/or $R^3$ are attached, to form a heterocyclic ring;

$R^7$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^7$ and $R^1$, or $R^7$ and $R^2$, or $R^7$ and $R^3$ can be joined, together with the —XC(W)X'— moiety of the —XC(W)X'R$^7$ group and the carbon atoms to which $R^1$ and/or $R^2$ and/or $R^3$ are attached, to form a heterocyclic ring;

$R^8$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^8$ and $R^1$, or $R^8$ and $R^2$, or $R^8$ and $R^3$ can be joined, together with the —C(W)X— moiety of the —C(W)XR$^8$ group and the carbon atoms to which $R^1$, $R^2$ and/or $R^3$ are attached, to form a heterocyclic ring;

Y is selected from the group consisting of sulfur, —S(O)— and —S(O)$_2$—;

$R^a$, $R^b$, $R^c$ and $R^d$ are each independently selected from the group consisting of hydrogen; sulfate; —C(O)R$^{10}$, wherein $R^{10}$ is selected from the group consisting of alkyl, alkenyl, alkaryl, alkoxyalkyl, aryl, cycloalkyl, cycloalkenyl, heteroaryl, heterocyclic, and thioalkoxyalkyl; and —P(O)(OR$^{11}$)$_2$, wherein each $R^{11}$ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl; and a linking arm covalently linking the compound of formula I' to the support; and n is an integer equal to 0 or 1; and pharmaceutically acceptable salts thereof;

with the proviso that only one of $R^1$, $R^2$, $R^3$, $R^5$, $R^6$, $R^7$, $R^8$, $R^a$, $R^b$, $R^c$ and $R^d$ is linked to the support; and with the further proviso that when $R^1$ and $R^2$ are joined, together with the carbon atoms to which $R^1$, $R^2$ and $R^3$ are attached, to form a cyclopentyl ring, $R^3$ is hydrogen, $R^4$ is —XR$^5$, X is oxygen, Y is sulfur and n is 1, then $R^a$, $R^b$, $R^c$, $R^d$ and $R^5$ are neither hydrogen nor a linking arm covalently linking the compound of formula I' to the support.

In another of its composition aspects, this invention provides a 1-thiogalactose derivative-containing support comprising a support having covalently bound thereto a plurality of at least one compound of formula I' above, wherein said compound of formula I' inhibits the binding of a toxin to its receptor, or said compound inhibits the binding of an organism to its cell surface receptor.

In still another of its composition aspects, this invention provides a pharmaceutical composition comprising from 1 to 99 weight percent of a pharmaceutically acceptable carrier and from 1 to 99 weight percent of a 1-thiogalactose derivative-containing support.

In another of its method aspects, this invention is directed to a method of ameliorating conditions associated with binding of a toxin to its receptor in an animal which method comprises administering to said animal an effective amount of a pharmaceutical composition comprising from 1 to 99 weight percent of a pharmaceutically acceptable carrier and from 1 to 99 weight percent of a 1-thiogalactose derivative-containing support, wherein the compound of formula I' inhibits the binding of the toxin to its receptor.

In another of its method aspects, this invention is directed to a method of ameliorating conditions associated with binding of an organism to its cell surface receptor in an animal which method comprises administering to said animal an effective amount of a pharmaceutical composition comprising from 1 to 99 weight percent of a pharmaceutically acceptable carrier and from 1 to 99 weight percent of a 1-thiogalactose derivative-containing support, wherein the compound of formula I' inhibits the binding of the organism to its cell surface receptor.

In a preferred embodiment of this invention, the support employed in the above compositions and methods is a non-absorbable support. More preferably, the support is a non-absorbable solid support.

Preferred compounds of formula I above for use in this invention include those set forth in formula IA below:

IA wherein $R^1$, $R^2$, $R^3$, $R^4$ and n are selected as shown in Table I below.

TABLE I

| n | $R^1$ | $R^2$ | $R^3$ | $R^4$ |
|---|---|---|---|---|
| 0 | —CH$_2$CH$_2$CH$_2$— | | — | —OH |
| 0 | —CH$_2$CH$_2$CH$_2$CH$_2$— | | — | —OH |
| 1 | —? | —CH$_3$ | —H | —OH |
| 1 | —H | cyclopenta-1,3-diyl | | —OH |
| 1 | —CH$_2$CH$_2$CH$_2$CH$_2$— | | —H | —OH |
| 1 | —C(CH$_3$)$_2$CH$_2$— | | —H | —OH |
| 1 | —CH$_2$CH$_2$— | | —H | —OH |
| 1 | —CH$_3$ | —CH$_3$ | —H | —OH |
| 1 | —C(CH$_3$)$_2$CH$_2$CH$_2$— | | —H | —OH |
| 1 | —CH$_2$CH$_2$CH$_2$— | | —H | —OH |
| 1 | —CH$_2$CH$_2$C(CH$_3$)$_2$— | | —H | —OH |
| 0 | —CH$_2$CH$_2$CH$_2$— | | — | —NH$_2$ |
| 0 | —CH$_2$CH$_2$CH$_2$CH$_2$— | | — | —NH$_2$ |
| 1 | —? | —CH$_3$ | —H | —NH$_2$ |
| 1 | —H | cyclopenta-1,3-diyl | | —NH$_2$ |
| 1 | —CH$_2$CH$_2$CH$_2$CH$_2$— | | —H | —NH$_2$ |
| 1 | —C(CH$_3$)$_2$CH$_2$— | | —H | —NH$_2$ |
| 1 | —CH$_3$ | —CH$_3$ | —H | —NH$_2$ |
| 1 | —CH$_2$CH$_2$CH$_2$— | | —H | —NH$_2$ |
| 1 | —CH$_2$CH$_2$C(CH$_3$)$_2$— | | —H | —NH$_2$ |
| 0 | —CH$_2$CH$_2$CH$_2$— | | — | —NHC(O)CH$_3$ |
| 0 | —CH$_2$CH$_2$CH$_2$CH$_2$— | | — | —NHC(O)CH$_3$ |

TABLE I-continued

| n | R¹ | R² | R³ | R⁴ |
|---|---|---|---|---|
| 1 | —? | —CH₃ | —H | —NHC(O)CH₃ |
| 1 | —H | cyclopenta-1,3-diyl | | —NHC(O)CH₃ |
| 1 | —CH₂CH₂CH₂CH₂— | | —H | —NHC(O)CH₃ |
| 1 | —C(CH₃)₂CH₂— | | —H | —NHC(O)CH₃ |
| 1 | —CH₃ | —CH₃ | —H | —NHC(O)CH₃ |
| 1 | —CH₂CH₂CH₂— | | —H | —NHC(O)CH₃ |
| 1 | —CH₂CH₂C(CH₃)₂— | | —H | —NHC(O)CH₃ |
| 0 | —CH₂CH₂CH₂— | | — | —NHC(O)?-(2-COOH) |
| 0 | —CH₂CH₂CH₂CH₂— | | — | —NHC(O)?-(2-COOH) |
| 1 | —? | —CH₃ | —H | —NHC(O)?-(2-COOH) |
| 1 | —H | cyclopenta-1,3-diyl | | —NHC(O)?-(2-COOH) |
| 1 | —CH₂CH₂CH₂CH₂— | | —H | —NHC(O)?-(2-COOH) |
| 1 | —CH₃ | —CH₃ | —H | —NHC(O)?-(2-COOH) |
| 1 | —CH₂CH₂CH₂— | | —H | —NHC(O)?-(2-COOH) |
| 0 | —CH₂CH₂CH₂— | | — | —NHCH₂COOH |
| 0 | —CH₂CH₂CH₂CH₂— | | — | —NHCH₂COOH |
| 1 | —? | —CH₃ | —H | —NHCH₂COOH |
| 1 | —H | cyclopenta-1,3-diyl | | —NHCH₂COOH |
| 1 | —CH₂CH₂CH₂CH₂— | | —H | —NHCH₂COOH |
| 1 | —C(CH₃)₂CH₂— | | —H | —NHCH₂COOH |
| 1 | —CH₂CH₂— | | —H | —NHCH₂COOH |
| 1 | —CH₃ | —CH₃ | —H | —NHCH₂COOH |
| 1 | —C(CH₃)₂CH₂CH₂— | | —H | —NHCH₂COOH |
| 1 | —CH₂CH₂CH₂— | | —H | —NHCH₂COOH |
| 1 | —CH₂CH₂C(CH₃)₂— | | —H | —NHCH₂COOH |
| 0 | —CH₂CH₂CH₂— | | — | —NHCH₂CH₂COOH |
| 0 | —CH₂CH₂CH₂CH₂— | | — | —NHCH₂CH₂COOH |
| 1 | —? | —CH₃ | —H | —NHCH₂CH₂COOH |
| 1 | —H | cyclopenta-1,3-diyl | | —NHCH₂CH₂COOH |
| 1 | —CH₂CH₂CH₂CH₂— | | —H | —NHCH₂CH₂COOH |
| 1 | —C(CH₃)₂CH₂— | | —H | —NHCH₂CH₂COOH |
| 1 | —CH₂CH₂— | | —H | —NHCH₂CH₂COOH |
| 1 | —CH₃ | —CH₃ | —H | —NHCH₂CH₂COOH |
| 1 | —C(CH₃)₂CH₂CH₂— | | —H | —NHCH₂CH₂COOH |
| 1 | —CH₂CH₂CH₂— | | —H | —NHCH₂CH₂COOH |
| 1 | —CH₂CH₂C(CH₃)₂— | | —H | —NHCH₂CH₂COOH |
| 0 | —CH₂CH₂CH₂— | | — | —NHCH(COOH)CH₂CH(CH₃)₂ |
| 0 | —CH₂CH₂CH₂CH₂— | | — | —NHCH(COOH)CH₂CH(CH₃)₂ |
| 1 | —? | —CH₃ | —H | —NHCH(COOH)CH₂CH(CH₃)₂ |
| 1 | —CH₂CH₂CH₂CH₂— | | —H | —NHCH(COOH)CH₂CH(CH₃)₂ |
| 1 | —C(CH₃)₂CH₂— | | —H | —NHCH(COOH)CH₂CH(CH₃)₂ |
| 1 | —CH₂CH₂— | | —H | —NHCH(COOH)CH₂CH(CH₃)₂ |
| 1 | —CH₃ | —CH₃ | —H | —NHCH(COOH)CH₂CH(CH₃)₂ |
| 1 | —C(CH₃)₂CH₂CH₂— | | —H | —NHCH(COOH)CH₂CH(CH₃)₂ |
| 1 | —CH₂CH₂CH₂— | | —H | —NHCH(COOH)CH₂CH(CH₃)₂ |
| 0 | —CH₂CH₂CH₂— | | —H | —NHCH(COOH)CH₂-(imidizol-4-yl) |
| 0 | —CH₂CH₂CH₂CH₂— | | —H | —NHCH(COOH)CH₂-(imidizol-4-yl) |
| 1 | —? | —CH₃ | —H | —NHCH(COOH)CH₂-(imidizol-4-yl) |
| 1 | —CH₂CH₂CH₂CH₂— | | —H | —NHCH(COOH)CH₂-(imidizol-4-yl) |
| 1 | —C(CH₃)₂CH₂— | | —H | —NHCH(COOH)CH₂-(imidizol-4-yl) |
| 1 | —CH₂CH₂— | | —H | —NHCH(COOH)CH₂-(imidizol-4-yl) |
| 1 | —CH₃ | —CH₃ | —H | —NHCH(COOH)CH₂-(imidizol-4-yl) |
| 1 | —C(CH₃)₂CH₂CH₂— | | —H | —NHCH(COOH)CH₂-(imidizol-4-yl) |
| 1 | —CH₂CH₂CH₂— | | —H | —NHCH(COOH)CH₂-(imidizol-4-yl) |
| 0 | —CH₂CH₂CH₂— | | — | —NHCH(COOH)CH₂-(indol-3-yl) |
| 0 | —CH₂CH₂CH₂CH₂— | | — | —NHCH(COOH)CH₂-(indol-3-yl) |
| 1 | —? | —CH₃ | —H | —NHCH(COOH)CH₂-(indol-3-yl) |
| 1 | —CH₂CH₂CH₂CH₂— | | —H | —NHCH(COOH)CH₂-(indol-3-yl) |
| 1 | —C(CH₃)₂CH₂— | | —H | —NHCH(COOH)CH₂-(indol-3-yl) |
| 1 | —CH₂CH₂— | | —H | —NHCH(COOH)CH₂-(indol-3-yl) |
| 1 | —CH₃ | —CH₃ | —H | —NHCH(COOH)CH₂-(indol-3-yl) |
| 1 | —C(CH₃)₂CH₂CH₂— | | —H | —NHCH(COOH)CH₂-(indol-3-yl) |
| 1 | —CH₂CH₂CH₂— | | —H | —NHCH(COOH)CH₂-(indol-3-yl) |
| 0 | —CH₂CH₂CH₂— | | — | —NHCH(COOH)(CH₂)₃NHC(NH)NH₂ |
| 0 | —CH₂CH₂CH₂CH₂— | | — | —NHCH(COOH)(CH₂)₃NHC(NH)NH₂ |
| 1 | —? | —CH₃ | —H | —NHCH(COOH)(CH₂)₃NHC(NH)NH₂ |
| 1 | —CH₂CH₂CH₂CH₂— | | —H | —NHCH(COOH)(CH₂)₃NHC(NH)NH₂ |
| 1 | —C(CH₃)₂CH₂— | | —H | —NHCH(COOH)(CH₂)₃NHC(NH)NH₂ |
| 1 | —CH₂CH₂— | | —H | —NHCH(COOH)(CH₂)₃NHC(NH)NH₂ |
| 1 | —CH₃ | —CH₃ | —H | —NHCH(COOH)(CH₂)₃NHC(NH)NH₂ |
| 1 | —C(CH₃)₂CH₂CH₂— | | —H | —NHCH(COOH)(CH₂)₃NHC(NH)NH₂ |
| 1 | —CH₂CH₂CH₂— | | —H | —NHCH(COOH)(CH₂)₃NHC(NH)NH₂ |
| 1 | —C(CH₃)₂CH₂— | | —H | —NH—CH₃ |
| 1 | —C(CH₃)₂CH₂— | | —H | —NH—CH(CH₃)₂ |
| 1 | —C(CH₃)₂CH₂— | | —H | —NH—CH₂CH₂CH₃ |
| 1 | —C(CH₃)₂CH₂— | | —H | —NH—CH*(CH₃)CH₂CH₃ *(R)-isomer |
| 1 | —C(CH₃)₂CH₂— | | —H | —NH—CH*(CH₃)CH₂CH₃ *(S)-isomer |

TABLE I-continued

| n | R¹ | R² | R³ | R⁴ |
|---|---|---|---|---|
| 1 | —C(CH₃)₂CH₂— | | —H | —NH—CH(CH₂CH₃)₂ |
| 1 | —C(CH₃)₂CH₂— | | —H | —NH—(CH₂)₅CH₃ |
| 1 | —C(CH₃)₂CH₂— | | —H | —NH-cyclobut-1-yl |
| 1 | —C(CH₃)₂CH₂— | | —H | —NH-(3,3-dimethyl)cyclobut-1-yl |
| 1 | —C(CH₃)₂CH₂— | | —H | —NH-cyclopent-1-yl |
| 1 | —C(CH₃)₂CH₂— | | —H | —NH-(3-methyl)cyclopent-1-yl |
| 1 | —C(CH₃)₂CH₂— | | —H | —NH-(3,3-dimethyl)cyclopent-1-yl |
| 1 | —C(CH₃)₂CH₂— | | —H | —NH-cyclohex-1-yl |
| 1 | —C(CH₃)₂CH₂— | | —H | —NH-(3-methyl)cyclohex-1-yl |
| 1 | —C(CH₃)₂CH₂— | | —H | —NH-(4-methyl)cyclohex-1-yl |

DETAILED DESCRIPTION OF THE INVENTION

Figure 1:
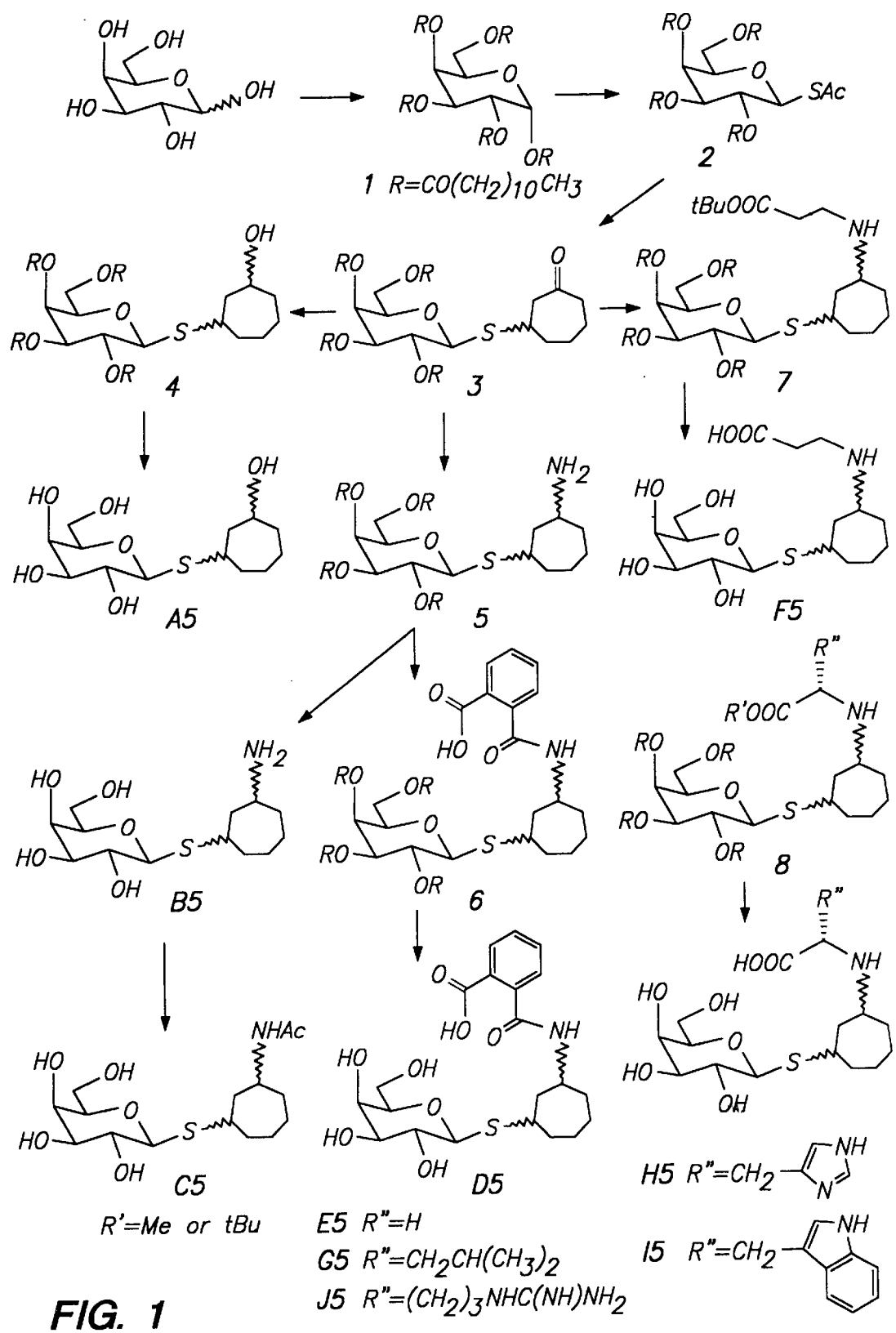
FIG. 1 illustrates a preferred reaction scheme which can be used to prepare various 1-thiogalactose derivatives from an α,β-unsaturated carbonyl compound, i.e., cyclohept-2-en- 1-one.

This invention relates, in one embodiment, to compounds which inhibit the binding of toxins, such as heat-labile enterotoxin or cholera toxin, to their receptors either in vitro or in vivo. In another embodiment, the compounds of this invention inhibit binding of organisms (e.g., bacteria, virus, fungi, and the like), such as *Vibrio cholerae* or enterotoxigenic strains of *Escherichia coli*, to their cell surface receptors. However, prior to describing this invention in further detail, the following terms will first be defined.

Definitions

"Acyl" refers to the groups alkyl—C(O)—, aryl—C(O)—, and heteroaryl—C(O)— where alkyl, aryl and heteroaryl are as defined herein.

"Acylamino" refers to the group —C(O)NRR where each R is independently hydrogen or alkyl.

"Acyloxy" refers to the groups alkyl—C(O)O—, aryl—C(O)O—, heteroaryl—C(O)O—, and heterocyclic—C(O)O—where alkyl, aryl, heteroaryl and heterocyclic are as defined herein.

"Alkaryl" refers to -alkylene-aryl groups preferably having from 1 to 8 carbon atoms in the alkylene moiety and from 6 to 10 carbon atoms in the aryl moiety. Such alkaryl groups are exemplified by benzyl, phenethyl and the like.

"Alkoxy" refers to the group alkyl—O—. Such alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like.

"Alkoxyalkyl" refers to the group -alkylene-O-alkyl which includes by way of example, methoxymethyl (CH₃OCH₂—), methoxyethyl (CH₃—O—CH₂CH₂—) and the like.

"Alkenyl" refers to alkenyl groups preferably having from 2 to 8 carbon atoms and more preferably 2 to 6 carbon atoms and having at least 1 and preferably from 1–2 sites of alkenyl unsaturation. Such alkenyl groups include ethenyl (—CH=CH₂), n-propenyl (i.e., allyl) (—CH₂CH=CH₂), iso-propenyl (—C(CH₃)=CH₂), and the like.

"Alkyl" refers to monovalent alkyl groups preferably having from 1 to 8 carbon atoms and more preferably 1 to 6 carbon atoms. This term is exemplified by groups such as methyl, ethyl, n-propyl, iso-propyl, n-butyl, iso-butyl, n-hexyl, and the like.

"Substituted alkyl" refers to a branched or straight chain alkyl group of from 1 to 8 carbon atoms having from 1 to 3 substituents selected from the group consisting of hydroxy, acyl, acylamino, acyloxy, alkoxy, alkenyl, alkynyl, amino, aminoacyl, aryl, aryloxy, carboxy, carboxyalkyl, cyano, cycloalkyl, guanidino, halo, heteroaryl, heterocyclic, nitro, thiol, thioaryloxy, thioheteroaryloxy, and the like. Preferred substituents include hydroxy and amino.

"Alkylene" or "alkyldiyl" refers to divalent alkylene groups preferably having from 1 to 8 carbon atoms and more preferably 1 to 6 carbon atoms. This term is exemplified by groups such as methylene (—CH₂—), ethylene (—CH₂CH₂—), the propylene isomers (e.g., —CH₂CH₂CH₂— and —CH(CH₃)CH₂—) and the like.

"Alkynyl" refers to alkynyl groups preferably having from 2 to 8 carbon atoms and more preferably 2 to 6 carbon atoms and having at least 1 and preferably from 1–2 sites of alkynyl unsaturation. Such alkynyl groups include ethynyl (—C≡CH), propargyl (—CH₂C≡CH) and the like.

"Amino acid" refers to any of the naturally occurring amino acids, as well as synthetic analogs and derivatives thereof. α-Amino acids comprise a carbon atom to which is bonded an amino group, a carboxy group, a hydrogen atom, and a distinctive group referred to as a "side chain". The side chains of naturally occurring amino acids are well known in the art and include, for example, hydrogen (e.g., as in glycine), alkyl (e.g., as in alanine, valine, leucine, isoleucine, proline), substituted alkyl (e.g., as in threonine, serine, methionine, cysteine, aspartic acid, asparagine, glutamic acid, glutamine, arginine, and lysine), alkaryl (e.g., as in phenylalanine and tryptophan), substituted arylalkyl (e.g., as in tyrosine), and heteroarylalkyl (e.g., as in histidine). One of skill in the art will appreciate that the term "amino acid" can also include β-, γ-, δ-, and ω-amino acids, and the like. Unnatural amino acids are also known in the art, as set forth in, for example, Williams[3], Evans et al.[4], Pu et al.[5], Williams et al.[6], and all references cited therein. Stereoisomers (e.g., D-amino acids) of the twenty conventional amino acids, unnatural amino acids such as α,α-disubstituted amino acids and other unconventional amino acids may also be suitable components for compounds of the present invention. Examples of unconventional amino acids include: 4-hydroxyproline, 3-methylhistidine, 5-hydroxylysine, and other similar amino acids and imino acids (e.g., 4-hydroxyproline).

"Aminoacyl" refers to the group —NRC(O)R where each R is independently hydrogen or alkyl.

"Aryl" refers to an unsaturated aromatic carbocyclic group of from 6 to 14 carbon atoms having a single ring (e.g., phenyl) or multiple condensed rings (e.g., naphthyl or anthryl). Preferred aryls include phenyl, naphthyl and the like.

Unless otherwise constrained by the definition for the aryl substituent, such aryl groups can optionally be substituted with from 1 to 3 substituents selected from the group consisting of hydroxy, acyl, acyloxy, alkyl, substituted alkyl, alkoxy, alkenyl, alkynyl, amino, aminoacyl, aryl, aryloxy, carboxy, carboxyalkyl, cyano, halo, nitro, heteroaryl, trihalomethyl and the like. Preferred substituents include alkyl, alkoxy, halo, carboxy, cyano, nitro, trihalomethyl, and thioalkoxy.

"Aryloxy" refers to the group aryl—O— where the aryl group is as defined herein including optionally substituted aryl groups as also defined herein.

"Carboxy" refers to the group —COOH.

"Carboxyalkyl" refers to the group —C(O)O—alkyl where alkyl is as defined herein.

"Cycloalkyl" refers to cyclic alkyl groups or cyclic alkyl rings of from 3 to 8 carbon atoms having a single cyclic ring or multiple condensed rings which can be optionally substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, aryloxy, carboxy, carboxyalkyl, cyano, halo, nitro, heteroaryl, trihalomethyl and the like. Preferred substituents include alkyl, alkoxy, halo, carboxy, cyano, nitro, trihalomethyl, and thioalkoxy. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl and the like, and spiro compounds. Examples of suitable cycloalkyl rings include single ring structures such as cyclopentane, cyclohexane, cycloheptane, cyclooctane, and the like, or multiple ring structures such as bicyclo[2.2.1]heptane, bicyclo[3.2.1]octane, and the like. Preferred cycloalkyl rings include cyclopentane, cyclohexane, cycloheptane and bicyclo[3.2.1]octane.

"Cycloalkenyl" refers to cyclic alkenyl groups or cyclic alkenyl rings of from 4 to 8 carbon atoms having a single cyclic ring and at least one point of internal unsaturation which can be optionally substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, aryloxy, carboxy, carboxyalkyl, cyano, halo, nitro, heteroaryl, trihalomethyl and the like. Preferred substituents include alkyl, alkoxy, halo, carboxy, cyano, nitro, trihalomethyl, and thioalkoxy. Examples of suitable cycloalkenyl groups include, for instance, cyclobut-2-enyl, cyclopent-3-enyl, cyclooct-3-enyl and the like. Such cycloalkenyl rings include, by way of example, cyclopentene, cyclohexene, and the like.

"Halo" or "halogen" refers to fluoro, chloro, bromo and iodo and preferably is either chloro or bromo.

"α-Halocarbonyl compound" refers to a compound having the general formula: Q—CHR$^1$—C(O)R$^2$ wherein R$^1$ and R$^2$ are as defined herein, and Q is chloro, bromo or iodo. Such α-halocarbonyl compounds include, by way of example, α-chloroaldehydes, α-bromoaldehydes, α-iodoaldehydes, α-chloroketones, α-bromoketones, α-iodoketones and the like.

"Heteroaryl" refers to a monovalent aromatic carbocyclic group of from 2 to 8 carbon atoms and 1 to 4 heteroatoms selected from oxygen, nitrogen and sulfur within the ring.

Unless otherwise constrained by the definition for the heteroaryl substituent, such heteroaryl groups can be optionally substituted with 1 to 3 substituents selected from the group consisting of alkyl, substituted alkyl, alkoxy, aryl, aryloxy, halo, nitro, heteroaryl, thioalkoxy, thioaryloxy and the like. Such heteroaryl groups can have a single ring (e.g., pyridyl or furyl) or multiple condensed rings (e.g., indolizinyl or benzothienyl). Preferred heteroaryls include pyridyl, pyrrolyl and furyl.

"Heterocycle" or "heterocyclic" refers to a monovalent saturated or unsaturated group having a single ring or multiple condensed rings, from 1 to 8 carbon atoms and from 1 to 4 hetero atoms selected from nitrogen, sulfur or oxygen within the ring. For the purposes of this application, the term "heterocycle" or "heterocyclic" does not include carbohydrate rings (i.e. mono- or oligosaccharides).

Unless otherwise constrained by the definition for the heterocyclic substituent, such heterocyclic groups can be optionally substituted with 1 to 3 substituents selected from the group consisting of alkyl, substituted alkyl, alkylene, alkoxy, aryl, aryloxy, halo, nitro, heteroaryl, thioalkoxy, thioaryloxy and the like. Such heteroaryl groups can have a single ring (e.g., pyrrolidinyl, piperidinyl, morpholinyl or tetrahydrofuranyl) or multiple condensed rings (e.g., indolinyl).

Examples of nitrogen heterocycles and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline and the like.

"Michael acceptor" refers to an α,β-unsaturated carbonyl compound having the general formula (II):

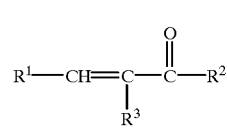

wherein R$^1$, R$^2$ and R$^3$ are as defined herein; or R$^1$CH=CR$^2$—C(O)XR$^8$, wherein R$^1$, R$^2$, R$^8$ and X are as defined herein. Such Michael acceptors include, by way of example, α,β-unsaturated aldehydes, α,β-unsaturated ketones, α,β-unsaturated esters, α,β-unsaturated thioesters, α,β-unsaturated amides and the like.

"Thioalkoxyalkyl" refers to the group -alkylene-S-alkyl which includes by way of example, thiomethoxymethyl (CH$_3$SCH$_2$—), thiomethoxyethyl (CH$_3$—S—CH$_2$CH$_2$—) and the like.

"Thiol" refers to the group —SH.

"Thioalkoxy" refers to the group —S—alkyl wherein the alkyl group is as defined herein.

"Thioaryloxy" refers to the group aryl—S— wherein the aryl group is as defined herein, including optionally substituted aryl groups as also defined herein.

"Thioheteroaryloxy" refers to the group heteroaryl—S— wherein the heteroaryl group is as defined herein, including optionally substituted heteroaryl groups as also defined herein.

The term "linking arm" refers to a chemical group or a covalent bond which optionally covalently attaches the 1-thiogalactose derivative to a support. Such groups typically comprise an alkylene, arylene or alkarylene group and at least one heteroatom, preferably 2 to 6 heteroatoms. A particularly preferred linking arm is illustrated in the formula:

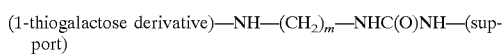

wherein m is an integer of from 2 to about 10. Preferably, m is 6.

The term "support" refers to an inert material or molecule to which a 1-thiogalactose derivative may be covalently bound, either directly or through a linking arm. When used in vivo, the solid support will be biocompatible and pharmaceutically acceptable. Preferably, the support is a non-absorbable support, i.e., when administered orally, the support passes unaffected through the gut without being absorbed into the circulatory system and is essentially completely eliminated from the body. More preferably, the support is a non-absorbable solid support. Typically, the support will contain a plurality of attachment sites for the 1-thiogalactose derivative, i.e. the support is preferably an oligovalent or polyvalent carrier. Suitable supports range, by way of illustration, from low molecular weight molecules, such 1,3,5-benzenetricarboxylic acid (trimesic acid), to organic and inorganic polymers, polysaccharides, polypeptides, glasses, silicates or minerals.

The term "solid support" refers to an inert, non-absorbable solid material to which a 1-thiogalactose derivative may be covalently bound, preferably via a linking arm. When used in vivo, the solid support will be biocompatible and pharmaceutically acceptable. Suitable solid supports include, by way of example only, silica, including synthetic silicates, such as porous glass; biogenic silicates, such as diatomaceous earth; hydrogels; silicate-containing minerals, such as kaolinite; synthetic polymers, such as polystyrene, polypropylene, etc.; polysaccharides such as dextrans, celluloses (CMC), alginates, chitins, chitosans and cyclodextrins; and the like.

Preferred solid support materials for use in this invention are silica supports which have been silylaminated with a w-aminoalkyltrialkoxysilane using conventional procedures. Suitable ω-aminoalkyltrialkoxysilanes include, for example, 3-aminopropyltriethoxysilane, 4-aminobutyltriethoxysilane and the like. A particularly preferred silica for use in such silylamination reactions is silica sold commercially under the tradename Chromosunder P™ by Manville Corp., Denver, Colo.

The term "toxin" refers to a compound produced by an organism which causes or initiates the development of a noxious, poisonous or deleterious effect in a host presented with the toxin. Such deleterious conditions may include fever, nausea, diarrhea, weight loss, neurologic disorders, renal disorders, hemorrhage, and the like. As used herein, the term "toxin" includes bacterial toxins, such as cholera toxin, heat-liable and heat-stable toxins of *E. coli*, toxins A and B of *Clostridium difficile*, aerolysins, hemolysins, and the like; toxins produced by protozoa, such as Giardia; toxins produced by fungi; and the like. Included within this term are exotoxins, i.e., toxins secreted by an organism as an extracelluar product, and enterotoxins, i.e., toxins present in the gut of an organism.

The terms "heat-labile enterotoxin" or "LT" refer to an enterotoxin of enterotoxigenic *E. coli* which initiates traveller's diarrhea and related conditions. This toxin has a lectin-like activity.

The term "traveller's diarrhea" refers to diarrhea of sudden onset, often accompanied by abdominal cramps, vomiting and fever that occurs sporadically in traveller's, usually during the first week of a trip. This diarrhea is most commonly caused by enterotoxigenic *E. coli*.

The term "cholera" refers to an acute epidemic infectious disease caused by *Vibrio cholerae*, wherein a soluble toxin elaborated in the intestinal tract by the Vibrio alters the permeability of the mucosa, causing a profuse watery diarrhea, extreme loss of fluid and electrolytes, and a state of dehydration and collapse, but no gross morphologic change in the intestinal mucosa.

The terms "cholera toxin" or "CT" refer to an enterotoxin of *V. cholerae* which initiates cholera and related conditions. This toxin has a lectin-like activity.

The phrase "inhibit(s) the binding of a toxin to its receptor" means that a compound inhibits the binding of a toxin to its receptor by at least 20%. For example, useful binding inhibition assays may measure inhibition of binding to ganglioside $G_{D1b}$ or ganglioside $G_{M1}$, neutralization of cytotoxic activity, or the like. Such binding is reported herein as percent toxin activity remaining so that those compounds which result in about 80% or less toxin activity remaining under the bioassay conditions disclosed herein are deemed to inhibit the binding of a toxin to its receptor.

The phrase "inhibit(s) the binding of heat-labile enterotoxin (LT) and/or cholera toxin (CT) to an LT and/or CT receptor" means that a compound inhibits the binding of LT and/or CT to an LT and/or CT receptor by at least 20%.

The phrase "inhibit(s) the binding of an organism to its cell surface receptor" means that a compound inhibits the binding of an organism, such as a bacterium, a virus, a protozoan, a fungus, and the like, to its cell surface receptor. For example, for organisms such as *Vibro cholera* or enterotoxigenic strains of *E. coli*, a compound is said to inhibit binding of an organism to a cell surface receptor if it reduces binding of a bacterial surface adhesion antigen, such as CFA I pili, by at least 10%.

The term "pharmaceutically acceptable salt" refers to pharmaceutically acceptable salts of a compound of formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

For purpose of this application, all sugars are referenced using conventional three letter nomenclature. All sugars are assumed to be in the D-form unless otherwise noted, except for fucose, which is in the L-form. Further, all sugars are in the pyranose form.

When chiral centers are found in the 1-thiogalactose derivatives of this invention other than the chiral centers of the galactose moiety, this invention encompasses all possible stereoisomers. For example, when n is 0 in formula I, the carbon atoms to which $R^1$ and $R^2$ are attached may have an R,R or R,S or S,R or S,S configuration. Similarly, when n is 1, the carbon atoms to which $R^1$, $R^2$ and $R^3$ are attached may have an R,R,R or S,R,R or R,S,R or R,R,S or S,S,R or S,R,S or R,S,S or S,S,S configuration.

General Synthetic Procedures

The 1-thiogalactose derivatives of this invention may be prepared by the following general methods and procedures. It should be appreciated that where typical or preferred process conditions (e.g., reaction temperatures, times, mole ratios of reactants, solvents, pressures, etc.) are given, other process conditions may also be used unless otherwise stated. Optimum reaction conditions may vary with the particular reactants or solvents used, but such conditions can be determined by one skilled in the art by routine optimization procedures.

The 1-thiogalactose derivatives of this invention are typically prepared by reaction of a 2,3,4,6-tetra-O-protected 1-thiogalactose intermediate with an α,β-unsaturated carbonyl compound or an α-halocarbonyl compound. The resulting carbonyl-containing intermediate is then reduced or reductively aminated to give an alcohol or an amine compound. Optionally, these alcohol or amine compounds can be further derivatized by reaction with, for example, acyl halides, acyl anhydrides, halo formates and isocyanates to afford esters, amides, carbonates, ureas and the like. Amine compounds can also be reductively alkylated with aldehydes and ketones to from secondary amines. Such derivatization reactions of alcohols and amines are well known to those of ordinary skill in the art and can be accomplished using art recognized procedures.

The α,β-unsaturated carbonyl compounds employed in preparing the 1-thiogalactose derivatives of this invention have the general formula (II):

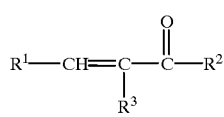

wherein $R^1$, $R^2$ and $R^3$ are as defined above; or $R^1CH=CR^2$—$C(O)XR^8$, wherein $R^1$, $R^2$, $R^8$ and X are as defined above. These compounds are either commercially available or can be prepared from commercially available materials using art recognized procedures. For example, such compounds can be prepared via a Wittig reaction from an aldehyde, $R^1CHO$, and a β-carbonyl phosphorane, such as $(Ph)_3PC(R^3)C(O)R^2$.

Preferred α,β-unsaturated carbonyl compounds for use in this invention include, by way of example, cyclopent-2-en-1-one, 4,4-dimethylcyclopent-2-en-1-one, cyclohex-2-en-1-one, 4,4-dimethylcyclohex-2-en- 1-one, 6,6-dimethylcyclohex-2-en- 1-one, cyclohept-en-1-one, and 3-methylene-2-norbornanone.

The α-halocarbonyl compounds employed in preparing the 1-thiogalactose derivatives of this invention have the general formula: Q—$CHR^1$—$C(O)R^2$ wherein $R^1$ and $R^2$ are as defined above, and Q is chloro, bromo or iodo. Such compounds are either commercially available or can be prepared from commercially available materials using art recognized procedures. Preferred α-halocarbonyl compounds for use in this invention include, by way of example, 2-chlorocyclopentanone and 2-chlorocyclohexanone. Alternatively, carbonyl compounds having a leaving group other than a halogen in the α-position may be employed. Suitable leaving groups include, by way of illustration, various sulfonic ester groups, such as tosylate, mesylate, brosylate and nosylate groups and the like, and fluorinated sulfonic ester groups, such as triflate, nonaflate and tresylate groups and the like.

Figure 2:
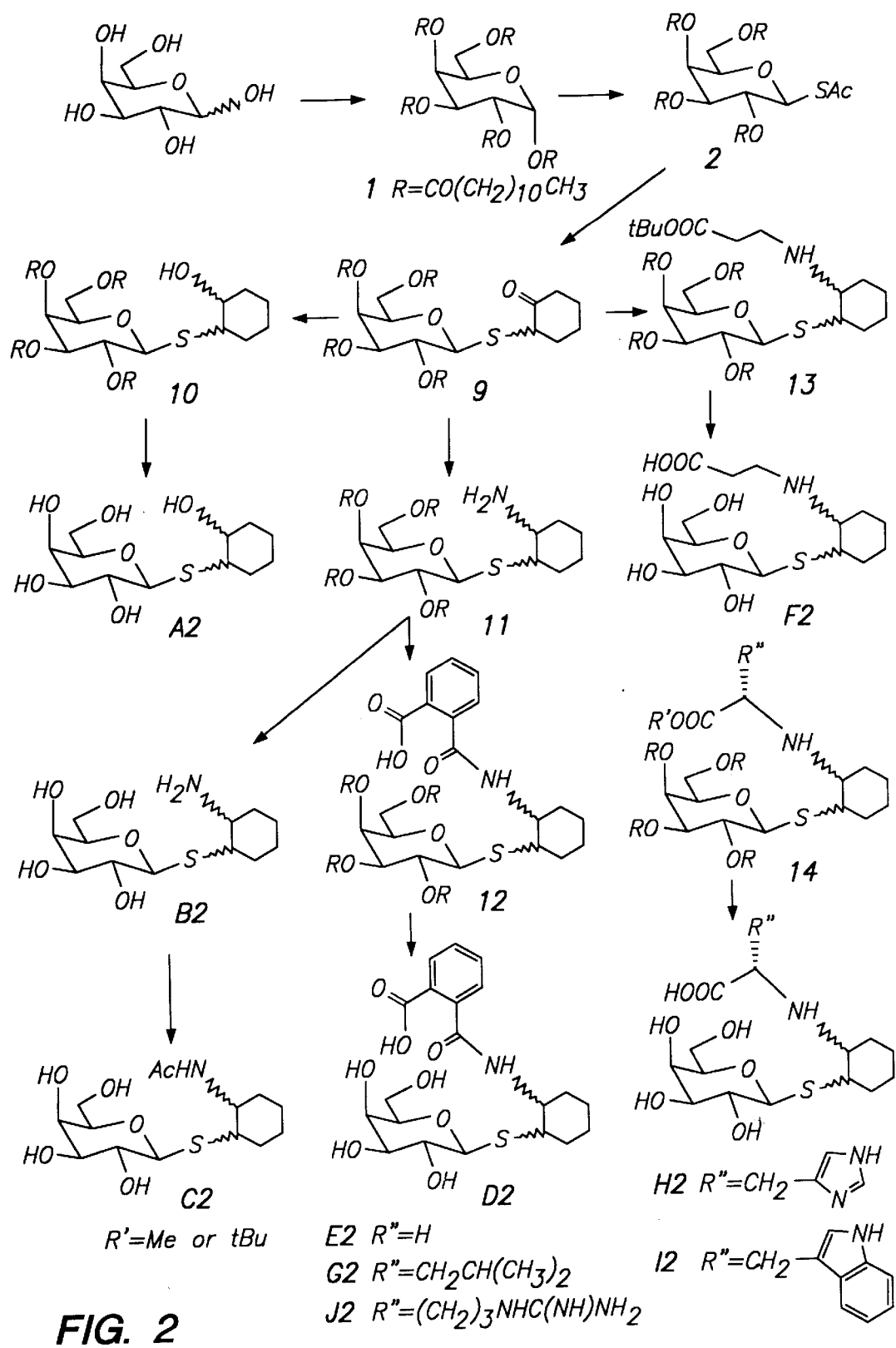
FIG. 2 illustrates a preferred reaction scheme which can be used to prepare various 1-thiogalactose derivatives from an a-halocarbonyl compound, i.e, 2-chlorocyclohexanone.

The synthesis of various 1-thiogalactose derivatives from either an α,β-unsaturated carbonyl compound or an α-halocarbonyl compound is illustrated in FIGS. 1 and 2, respectively. FIG. 1 illustrates the synthesis of various 1-thiogalactose derivatives from cyclohept-2-en-1-one. FIG. 2 illustrates the synthesis of various 1-thiogalactose from 2-chlorocyclohexanone. It will be readily apparent to those of ordinary skill in the art that the synthetic procedure illustrated in FIGS. 1 and 2 and the following reaction conditions can be modified by selecting the appropriate starting materials and reagents to allow the preparation of other 1-thiogalactose derivatives of this invention.

As shown in FIG. 1, D-galactose is perlauroylated by contacting D-galactose with at least 5 equivalents, and preferably 10 equivalents, of lauroyl chloride. This reaction is generally conducted in an inert diluent, such pentane, hexane, dichloromethane and the like, using a tertiary amine such as pyridine or triethylamine to neutralize the hydrochloric acid generated during the reaction. Preferably, a catalytic amount of 4-(N,N-dimethylamino)pyridine is added to the reaction mixture to facilitate this reaction. Typically, this reaction is conducted at a temperature of from about −78° C. to about 30° C. for about 0.5 to about 96 hours to afford 1,2,3,4,6-penta-O-lauroyl-α-D-galactopyranose, 1, in approximately 70% yield from D-galactose.

Compound 1 is then converted into 1-S-acetyl-2,3,4,6-tetra-O-lauroyl-1-thio-β-D-galactopyranose, 2, by reaction of 1 with an excess of thiolacetic acid. In one embodiment, this reaction is conducted in the presence of an excess of boron trifluoride etherate, preferably using about 15 to 20 equivalents of boron trifluoride etherate based on 1, in an inert diluent, such as dichloromethane and the like. Typically, this reaction is conducted initially at about 0° C. and then at about 20° C. to about 30° C. for about 0.5 to about 48 hours.

In another embodiment, compound 2 can be prepared from 1 by contacting 1 with at least one equivalent, preferably 1 to 1.2 equivalents, of benzylamine to selectively remove the 1-lauroyl group. This reaction is typically conducted at about 25° C. to about 30° C. for about 1 to about 96 hours to provide for 2,3,4,6-tetra-O-lauroyl-(α,β)-galactopyranoside. This intermediate is then converted into an O-(2,3,4, 6-tetra-O-lauroyl-(α,β)-galactopyranosyl) trichloroacetimidate intermediate by contacting the tetralauroyl compound with an excess of trichloroacetonitrile, preferably about 10 equivalents, and about 0.8 to about 1.0 equivalents, of 1,8-diazabicyclo[5.4.0]undec-7-ene (DBU) in an inert diluent, such as dichloromethane. The resulting O-trichloroacetidate intermediate is then contacted with an excess of thiolacetic acid in an inert diluent, such as dichloromethane, at about 25° C. to about 30° C. for about 1 to about 96 hours to provide for 1-S-acetyl-2,3,4,6-tetra-O-lauroyl-1-thio-β-D-galactopyranose, 2.

In still another embodiment, compound 2 can be prepared by contacting compound 1 with about 1.5 to about 2.0 equivalents of thiolacetic acid and about 0.5 equivalents of trimethylsilyl trifluoromethanesulfonate based on 1 in an inert diluent, such as dichloromethane and the like. Typically, this reaction is conducted initially at about 0° C. and then at about 20° C. to about 30° C. for about 0.5 to about 72 hours. This method is especially preferred since it provides the highest yield of compound 2 and produces no detectable traces of the corresponding α-isomer.

If desired, however, the ol-isomer, i.e., 1-S-acetyl-2,3,4, 6-tetra-O-lauroyl-1-thio-α-D-galactopyranose, can be readily prepared by contacting compound 1 with an excess, preferably about 20 equivalents, of thioacetic acid in the presence of about 1.0 to 1.1 equivalents of tin (IV) chloride in an inert diluent, such toluene, at ambient temperature for about 0.5 to about 2 hours. Alternatively, treatment of compound 1 with an excess, preferably about 3 to about 6 equivalents, of thioacetic acid in the presence of about 2.0 to 3.0 equivalents of trimethylsilyl trifluoromethanesulfonate in an inert diluent, such dichloromethane, at ambient temperature for about 12 to about 48 hours affords 1-S-acetyl-2,3,4,6-tetra-O-lauroyl-1-thio-β-D-galactopyranose.

The Michael addition of compound 2 to cyclohept-2-en-1-one then affords cycloheptanon-3-yl 2,3,4,6-tetra-O-lauroyl-1-thio-β-D-galactopyranoside, 3. This reaction is typically conducted by contacting 2 with at least one equivalent, preferably 1.0 to 1.2 equivalents, of cyclohep-2-en-1-one in the presence of a molar excess of a dialkylamine, such as diethylamine. Without being limited by any theory, it is believed that the dialkylamine first reacts with the thioacetyl of compound 2 thereby forming in situ the thiol derivative of compound 2 which then reacts under basic conditions generated by the dialkylamine with a Michael adduct.

Typically, this reaction is conducted in an inert diluent, such as dichloromethane, at a temperature of from about −40° C. to about 50° C. for about 1 to about 6 hours.

The carbonyl group of compound 3 can then reduced using a reducing agent to provide for 3-hydroxycycloheptyl 2,3,4,6-tetra-O-lauroyl- 1-thio-β-D-galactopyranoside, galactopyranoside, 4. Preferably, this reduction is conducted by contacting 3 with sodium borohydride, preferably about 1.2 to about 2.0 equivalents of sodium borohydride based on 3. Generally, this reaction is conducted in an inert diluent, such as tetrahydrofuran, isopropanol and mixture thereof, at a temperature of about 25° C. to about 30° C. for about 0.5 to about 3.0 hours. The resulting alcohol, 4, is readily purified by solid-phase extraction on C18 silica gel using pentane as an eluent.

Removal of the lauroyl groups from alcohol 4 is then accomplished by treating 4 with an excess of sodium methoxide in methanol and an inert diluent, such as dichloromethane, at about 25° C. to about 30° C. for about 1 to about 24 hours. for 3-hydroxycycloheptyl 1-thio-β-galactopyranoside, A5.

Alternatively, compound 3 can be reductively aminated to provide for 3-aminocycloheptyl 2,3,4,6-tetra-O-lauroyl-1-thio-β-D-galactopyranoside, 5. In one embodiment of this reaction, compound 3 is contacted with an excess of ammonium acetate and at least one equivalent of sodium cyanoborohydride based on 3. This reaction is typically conducted in an inert diluent, such as methanol, tetrahydrofuran and mixtures thereof, at a temperature of about 25° C. to about 30° C. for about 1 to about 72 hours.

In another preferred embodiment, the reductive amination reaction is accomplished by contacting compound 3 with an excess of ammonium acetate and an excess of trimethyl orthoformate based on 3, in an inert diluent, such as 1,2-dichloroethane at a temperature of about 25° C. to about 30° C. for about 12 to about 72 hours to form an imine intermediate. The imine intermediate is generally not isolated but is contacted in situ with an excess of sodium borohydride, preferably about 1.2 to about 1.5 equivalents of sodium borohydride, based on 3. The resulting amino compound 5 is then readily purified by solid-phase extraction on C18 silica gel using pentane as an eluent.

Optionally, the amine group formed by reductive amination can be acylated with conventional acylating agents under conventional conditions. The acylating agent is generally of the formula L—C(O)R$^6$ where L is a leaving group such as a halide, an activated ester, and the like.

The lauroyl groups are removed from compound 5 by contacting 5 with an excess of sodium methoxide in methanol and an inert diluent, such as dichloromethane, at about 25° C. to about 30° C. for about 1 to about 24 hours. Neutralization of the reaction mixture with Amberlite IR-50S (H$^+$) resin then provides for 3-aminocycloheptyl 1-thio-β-galactopyranoside, B5.

In one example, the primary amine group of compound B5 can optionally be acylated by contacting B5 with an excess of acetic anhydride in methanol containing a trace of water. Generally, this reaction is conducted at about 25° C. to about 30° C. for about 2 to about 24 hours to provide for 3-acetamidocycloheptyl 1-thio-β-galactopyranoside, C5.

Alternatively, the primary amine group of 5 can be acylated with phthalic anhydride before removal of the lauroyl groups to provide for 3-(2-carboxybenzamido) cycloheptyl 2,3,4, 6-tetra-O-lauroyl- 1 -thio-β-D-galactopyranoside, 6. This reaction is typically conducted by contacting compound 5 with at least one molar equivalent, preferably with an excess of phthalic anhydride. Preferably, this reaction is conducted in dry pyridine containing a catalytic amount of 4-(N,N-dimethylamino)pyridine. The reaction is typically conducted at about 25° C. to about 30° C. for about 12 to about 48 hours to provide for compound, 6. Removal of the lauroyl groups from 6 is then accomplished by treating 6 with sodium methoxide in methanol and an inert diluent, such as dichloromethane, at about 25° C. to about 30° C. for about 1 to about 24 hours. Neutralization of the reaction mixture with Amberlite IR-50S (H$^+$) resin then provides for 3-(2-carboxybenzamido)cycloheptyl 1-thio-β-D-galactopyranoside, D5.

As shown in FIG. 1, compound 3 can also be reductively aminated with an amino acid ester to provide for intermediates 7 or 8. Specifically, compound 3 is contacted with a molar excess of β-alanine tert-butyl ester, preferably with 10 equivalents based on 3, in the presence of at least one molar equivalent, preferably about 1.0 to about 1.2 equivalents, of sodium cyanoborohydride. Typically, this reaction is conducted in an essentially anhydrous inert diluent, such as acetonitrile, at a temperature of about 25° C. to about 30° C. for about 1 to about 72 hours. The resulting intermediate 7 is readily purified by solid-phase extraction on C18 silica gel using pentane as the eluent.

The tert-butyl ester group of compound 7 is readily hydrolyzed to the corresponding carboxylic acid by treating 7 with an excess of trifluoroacetic acid in an inert diluent such as dichloromethane. This reaction is typically conducted at about 25° C. to about 30° C. for about 1 to about 10 hours. The lauroyl groups of the resulting carboxylic acid intermediate are then removed using sodium methoxide in methanol as described above to provide for Nβ-[1-thio-β-D-galactopyranosyl)cyclohept-3-yl]-β-alanine, F5.

In a similar manner, compound 3 can be reductively aminated using other amino acid esters, such as glycine tert-butyl ester, L-leucine tert-butyl ester, L-histidine methyl ester, L-tryptophan methyl ester, and L-arginine methyl ester, to provide for intermediate 8. In those cases where the amino acid ester employed is a tert-butyl ester, the tert-butyl ester is cleaved as described above using trifluoroacetic acid to afford Nα-[1-(1-thio-β-D-galactopyranosyl)cyclohept-3-yl]-glycine, E5, and Nα-[1-(1 -thio-β-D-galactopyranosyl) cyclohept-3-yl]-L-leucine, G5. Alternatively, in those cases where an amino acid methyl ester is employed, the lauroyl groups of intermediate 8 are preferably removed before cleaving the methyl ester by treatment of 8 with sodium methoxide in methanol as described above. Subsequently, the methyl ester of the amino acid moiety is cleaved to the corresponding carboxylic acid by treatment with an excess of aqueous lithium hydroxide for about 0.5 to about 2 hours. Neutralization of the reaction mixture with Amberlite IR-50S (H$^+$) resin then provides for Nα-[1-(1-thio-β-D-galactopyranosyl)cyclohept-3-yl]-L-histidine, H5, Nα-[1-(1-thio-β-D-galactopyranosyl)cyclohept-3-yl]-L-tryptophan, I5, and Nα-[1-(1-thio-β-D-galactopyranosyl)cyclohept-3-yl]-L-arginine, J5.

Additionally, if desired, the hydroxyl group of alcohol derivatives, such as compound 4, can be converted into a leaving group, such as the mesylate, tosylate, etc., and displaced with various nucleophiles. For example, treatment of an alcohol derivative with an excess, preferably about 1.1 to about 1.5 equivalents, of methanesulfonyl chloride in pyridine and an inert diluent, such as THF, affords the corresponding mesylate. The mesylate group can then be displaced with, for example, sodium azide to provide the corresponding azido derivative. This reaction is typically conducted by contacting the mesylate compound with an excess, preferably about 5 to about 50 equivalents of sodium azide in an inert diluent, such as N,N-dimethylformamide, THF and mixtures thereof, at a temperature of from about 50° C. to about 100° C. for about 1 to about 6 hours. Preferably, a crown ether, such as 18-crown-6, is added to the reaction mixture to promote the displacement reaction.

The azido derivative can then be reduced with a reducing agent to afford the corresponding primary amine, i.e., a compound such as 5. Preferably, this reaction is conducted by contacting the azido compound with about 1.0 to about 1.1 equivalents of sodium borohydride and about 2.0 to about 2.2 equivalents of nickel chloride ($NiCl_2$) in an inert diluent, such as ethanol, isopropanol, or mixtures thereof, at a temperature of from about 0° C. to about 50° C. for about 0.5 to about 6 hours. Removal of the lauroyl protecting groups can then be accomplished using the procedures described above.

Additionally, the primary amine group of amino compounds such as 5 can be further derivatized by reductive alkylation to afford a secondary amine. Typically, this reaction is conducted by contacting the primary amine with an excess, preferably about 2 to about 500 equivalents of an aldehyde or a ketone in the presence of at least one equivalent, preferably about 1.0 to about 10 equivalents, of a reducing agent, such as sodium triacetoxyborohydride. This reaction is typically conducted in an inert diluent, such as dichloromethane, methanol, or mixtures thereof, at a temperature of about 0° C. to about 50° C. for about 10 to about 48 hours. In a preferred embodiment, the ketone employed in this reaction is a cyclic ketone including, by way of example, cyclobutanones, such as 3,3-dimethylcyclobutan-1-one; cyclopentanones, such as 3,3-dimethylcyclopentan-1-one; cyclohexanones and cycloheptanones.

The lauroyl groups of the resulting secondary amine are then removed by contacting the lauroyl-protected compound with an excess of sodium methoxide in methanol and an inert diluent, such as dichloromethane, at about 25° C. to about 30° C. for about 1 to about 24 hours. Neutralization of the reaction mixture with Amberlite IR-50S ($H^+$) resin then provides the desired secondary amine compound.

As noted above, FIG. 2 illustrates the synthesis of various 1-thiogalactose derivatives using an α-halocarbonyl carbonyl compound, i.e., 2-chlorocyclohexanone. As shown in FIG. 2, 1-S-acetyl-2,3,4,6-tetra-O-lauroyl-1-thio-β-D-galactopyranose, 2, prepared as described above, reacts with 2-chlorocyclohexanone to give cyclohexanon-2-yl 2,3,4,6-tetra-O-lauroyl-1-thio-β-D-galactopyranoside, 9. This reaction is typically conducted by contacting 2 with at least one equivalent, preferably 1.0 to 1.2 equivalents, of 2-chlorocyclohexanone in the presence of an excess of a dialkylamine, such as diethylamine. Typically, this reaction is conducted in an inert diluent, such as dichloromethane, at a temperature of from about −40° C. to about 50° C. for about 1 to about 6 hours to afford compound 9.

Compound 9 can then be reacted using the same reagents and conditions described above for compound 3 to afford various 1-thiogalactose derivatives. Specifically, compound 9 is reduced with sodium borohydride to provide 10 which, after removal of the lauroyl groups, affords 2-hydroxycyclohexyl 1-thio-β-D-galactopyranoside, A2.

Alternatively, compound 9 is reductively aminated with ammonium acetate and sodium cyanoborohydride to provide for intermediate 11 which, upon removal of the lauroyl groups, affords 2-aminocyclohexyl 1-thio-β-D-galactopyranoside, B2. Compound B2 can then be acylated with acetic anhydride to give 2-acetamidocyclohexyl 1-thio-β-D-galactopyranoside, C2. Alternatively, intermediate 11 can be acylated with phthalic anhydride to provide for intermediate 12 which affords 2-(2-carboxybenzamidocyclohexyl 1-thio-β-D-galactopyranoside, D2, by removal of the lauroyl groups using the conditions described above.

Additionally, compound 9 can be reductively aminated using an β-alanine tert-butyl ester to provide for intermediate 13 which then affords Nβ-[1-(1-thio-β-D-galactopyranosyl)cyclohex-2-yl]-β-alanine, F2, upon deprotection. Alternatively, compound 9 can be reductive aminated with other amino acid esters, such as glycine tert-butyl ester, L-leucine tert-butyl ester, L-histidine methyl ester, L-tryptophan methyl ester, and L-arginine methyl ester, to provide intermediate 14 which upon deprotection, affords Nα-[1-(1-thio-β-D-galactopyranosyl)cyclohex-2-yl]-glycine E2, Nα-[1-(1-thio-β-D-galactopyranosyl) cyclohex-2-yl]-L-leucine G2, Nα-[1-(1-thio-β-D-galactopyranosyl)cyclohex-2-yl]-L-histidine H2, Nα-[1-(1-thio-β-D-galactopyranosyl)cyclohex-2-yl]-L-tryptophan I2, and Nα-[1-(1-thio-β-D-galactopyranosyl)cyclohex-2-yl]-L-arginine J2.

Optionally, the 1-thiogalactose derivatives of formula I wherein Y is a sulfide linking group (—S—) can be oxidized using conventional reagents and conditions to provide the corresponding sulfoxide (Y=—S(O)—) and sulfone (Y=—$SO_2$—) derivatives. Suitable reagents for oxidizing a sulfide compound to a sulfoxide include, by way of example, hydrogen peroxide, peracids such as 3-chloroperoxybenzoic acid (MCPBA), sodium periodate, sodium chlorite, sodium hypochlorite, calcium hypochlorite, tert-butyl hypochlorite and the like. Chiral oxidizing reagents (optically active reagents) may also be employed to provide chiral sulfoxides. Such optically active reagents are well known in the art and include, for example, the reagents described in Kagen et al.[7] and references cited therein.

The oxidation reaction is typically conducted by contacting the 1-thiogalactose derivative with about 0.95 to about 1.1 equivalents of the oxidizing reagent in an inert diluent, such as dichloromethane, at a temperature ranging from about 0° C. to about 50° C. for about 1 to about 48 hours. The resulting sulfoxide can then be further oxidized to the corresponding sulfone by contacting the sulfoxide with at least one additional equivalent of an oxidizing reagent, such as hydrogen peroxide, MCPBA, potassium permanganate and the like. Alternatively, the sulfone can be prepared directly by contacting the sulfide with at least two equivalents, and preferably an excess, of the oxidizing reagent.

In a similar manner, the 1-thiogalactose derivatives of formula I, wherein $R^4$ is —$XR^5$, X is sulfur and $R^5$ is a defined substituent other than hydrogen, can be oxidized to afford the corresponding sulfoxide (X=—S(O)—) and sulfone (X=$SO_2$—) derivatives.

Additionally, if desired, the hydroxyl groups of the galactose moiety may be readily acylated, sulfonylated or phosphorylated using art recognized procedures and reagents to provide compounds of formula I wherein at least one of $R^a$, $R^b$, $R^c$, and $R^d$ is —O—$SO^2$—OH, —C(O)$R^{10}$, —P(O)(O$R^{11}$)$_2$ or pharmaceutically acceptable salts thereof, where $R^{10}$ and $R^{11}$ are as defined above. Such acylation reactions may occur as an initial step of the synthesis (i.e., using an acyl halide, such as lauroyl chloride, as described above) or as a post-synthetic transformation of compounds of formula I where $R^a$, $R^b$, $R^c$, and $R^d$ are each hydrogen using, for example, acyl halides, anhydrides, halophosphates, sulfur trioxide, and the like.

For example, a de-blocked hydroxyl group can be sulfonylated by treating the hydroxy-containing compound with an excess, preferably about 1.1 to about 1.2 equivalents, of a pyridine:sulfur trioxide complex in an inert diluent, such as N,N-dimethylformamide, at ambient temperature for about 1 to about 24 hours. Typically, the resulting sulfate (i.e., —O—SO$_2$—OH) is isolated as its salt by treatment with, for example, a Na$^+$resin in an inert diluent, such as methanol. Further reaction conditions suitable for forming sulfates and phosphates can be found, for example, in U.S. Pat. No. 5,580,858[8].

In another embodiment of this invention, the 1-thiogalactose derivatives of this invention can be attached to a support, preferably a solid support, either through the galactose moiety or through the portion of the molecule derived from the Michael acceptor or the α-halocarbonyl compound. Methods for attaching compounds to supports through various functional groups are well known in the art and any of these known methods may be employed to covalently attach the 1-thiogalactose derivatives of this invention to a support.

By way of example, a 1-thiogalactose derivative of formula I wherein $R^4$ contains a carboxylic acid moiety can be covalently attached to an aminated solid support using conventional coupling procedures and reagents. Typically, such a coupling reaction will be conducted using well-known coupling reagents such as carbodiimides, BOP reagent (benzotriazol-1-yloxy-tris(dimethylamino) phosphonium hexafluorophosphonate) and the like. Suitable carbodiimides include, by way of example, dicyclohexylcarbodiimide (DCC), diisopropylcarbodiimide, 1-(3-dimethylaminopropyl)-3-ethylcarbodiimide (EDC) and the like. Preferably, a well-known coupling promoter, such as N-hydroxysuccinimide, 1-hydroxybenzotriazole and the like, is also employed in the reaction mixture to facilitate the coupling reaction.

The coupling reaction is typically conducted by contacting the solid support with an excess, preferably about 1.1 to about 10 or more equivalents, of the 1- thiogalactose derivative (based on the number of equivalents of amino groups present on the solid support) and at least one equivalent, preferably about 1.5 to about 3.0 equivalents, of the coupling reagent (based on the 1-thiogalactose derivative) in an inert diluent, such N,N-dimethylformamide and the like. If desired, least one equivalent, preferably about 1.5 to about 3.0 equivalents (based on the 1-thiogalactose derivative), of a coupling promoter such as 1-hydroxybenzotriazole may also be used in the reaction. Generally, the coupling reaction is conducted at a temperature ranging from about 0° C. to about 50° C. for about 24 to about 100 hours. Upon completion of the reaction, the solid support is preferably contacted with excess acetic anhydride in methanol at a temperature ranging from about 0° C. to about 40° C. for about 12 to about 24 hours to cap any unreacted amino groups present on the solid support. The yield of incorporation of the 1-thiogalactose derivative onto the solid support can be determined using well-established procedures such as those described, for example, by M. Dubois et al.[9].

The 1-thiogalactose derivatives of this invention can also be prepared on a solid support via solid-phase synthesis techniques. Typically, such solid-phase techniques involve first covalently attaching a 1-thiogalactose compound through a hydroxyl group on the galactose moiety to a solid support using conventional procedures and reagents. The covalently-bound 1-thiogalactose compound is then reacted using the procedures described above with an α,β-unsaturated carbonyl compound or an α-halocarbonyl compound. The resulting carbonyl-containing intermediate is then reduced or reductively aminated to give an alcohol or an amine compound which can be further derivatized as described herein.

By way of example, 1-dithioethyl-β-D-galactopyranoside is readily attached to a trityl chloride resin having about 0.80 to about 1.00 mmol/g of active chlorine by contacting the resin with about 0.75 to about 2.0 equivalents of 1-dithioethyl-β-D-galactopyranoside in pyridine containing a catalytic amount of 4-(N,N-dimethylamino)pyridine at a temperature ranging from about 25° C. to about 100° C. for about 12 to 48 hours. A free thiol group at the 1-position of the covalently bound galactose is then generated by treating the resin with dithiothreitol (Cleland's reagent) and triethylamine in an inert diluent, such as methanol, for about 6 to 24 hours at ambient temperature. The resulting 1-thio-β-D-galactopyranoside is then reacted as described above to afford a 1-thiogalactose derivative of formula I covalently attached to the solid support resin. If desired, the 1-thiogalactose derivative can be cleaved from the solid support resin by contacting the resin with an excess of trifluoroacetic acid and triisopropylsilane in an inert diluent, such as dichloromethane, at ambient temperature.

Utility

In one embodiment, the compounds of this invention are useful in blocking binding of toxins, such as heat-labile enterotoxin or cholera toxin, to their receptors either in vitro or in vivo. In another embodiment, the compounds of this invention inhibit binding of organisms (e.g., bacteria, virus, fungi, and the like), such as *Vibrio cholerae* or enterotoxigenic strains of *Escherichia coli,* to their cell surface receptors.

Accordingly, the compounds of this invention can be used to ameliorate conditions associated with infection by an organism, including gastrointestinal infections caused by enterovirulent organisms, such as *Vibrio cholerae* or enterotoxigenic strains of *Escherichia col,* including, by way of example, diarrhea, intestinal bleeding, abdominal pain, and the like.

When used in treating or ameliorating such conditions, the compounds of this invention are typically delivered to a patient in need of such treatment by a pharmaceutical composition comprising a pharmaceutically acceptable diluent and an effective amount of at least one compound of this invention. The amount of compound administered to the patient will vary depending upon what compound and/or composition is being administered, the purpose of the administration, such as prophylaxis or therapy, the state of the patient, the manner of administration, and the like. In therapeutic applications, compositions are administered to a patient already suffering from an infection, such as gastrointestinal infections associated with, for example, *Vibrio cholerae* or enterotoxigenic strains of *Escherichia coli,* in an amount sufficient to at least partially arrest further onset of the symptoms of the disease and its complications. An amount adequate to accomplish this is defined as "therapeutically effective dose." Amounts effective for this use will depend on the judgment of the attending clinician depending upon factors such as the degree or severity of the infection in the patient, the age, weight and general condition of the patient, and the like. Preferably, for use as therapeutics, the compounds described herein are administered at dosages ranging from about 0.1 to about 10 mg/kg/day.

Such pharmaceutical compositions may contain more than one compound of the present invention. For example, they may contain one compound of formula I which is highly effective at inhibiting the binding of LT and a different compound of formula I which is highly effective at inhibiting the binding of enterotoxigenic *E. coli* to cell surface receptors.

When a support having a compound of formula I' covalently attached is used for treating or ameliorating conditions associated with gastrointestinal infections, supports which are non-toxic, resistant to mechanical and chemical deposition are preferred. Those supports which pass unaffected through the gut and which are completely and rapidly eliminated following oral administration are most preferred, since such supports provide for rapid clearance of the toxin and/or pathogen from the subject.

As noted above, the compounds administered to a patient are in the form of pharmaceutical compositions described above which can be administered by a variety of routes including oral, rectal, transdermal, subcutaneous, intravenous, intramuscular, etc. These compounds are effective as both injectable and oral deliverable pharmaceutical compositions. Such compositions are prepared in a manner well known in the pharmaceutical art and comprise at least one active compound.

The pharmaceutical compositions are formulated in the presence of a pharmaceutically acceptable carrier. In making the compositions of this invention, the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, etc., containing, for example, up to 10% by weight of the active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragelatin, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The 1-thiogalactose derivatives of this invention can also be administered in the form of pro-drugs, i.e., as derivatives which are converted into a biologically active compound of formula I in vivo. Such pro-drugs will typically include compounds of formula I in which at least one of $R^a$, $R^b$, $R^c$, or $R^d$ is a biologically liable group, such as —C(O)$R^{10}$ or —P(O)(O$R^{11}$)$_2$, where $R^{10}$ and $R^{11}$ are as defined above.

The following examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| Å = | angstroms |
| bd = | broad doublet |
| bs = | broad singlet |
| BSA = | bovine serum albumin |
| d = | doublet |
| dd = | doublet of doublets |
| DMAP = | dimethylaminopyridine |
| eq. = | equivalents |
| g = | grams |
| L = | liter |
| m = | multiplet |
| meq = | milliequivalent |
| mg = | milligram |
| mL = | milliliter |
| mmol = | millimole |
| N = | normal |
| OPD = | o-phenylenediamine |
| PBS = | phosphate buffered saline at pH 7.2 |
| q = | quartet |
| quint. = | quintet |
| s = | singlet |
| t = | triplet |
| TFA = | trifluoroacetic acid |
| THF = | tetrahydrofuran |
| TLC = | thin layer chromatography |
| Tween 20 = | polyoxyethylenesorbitan monolaurate |
| μL = | microliter |

$^1$H-Nmr spectra were recorded with a Brueker AM-360 spectrometer and MALDI-TOF mass spectra were recorded with a HP G2020A (LD-TOF) instrument. Optical rotations were measured with a Perkin-Elmer 241 polarimeter. Reactions were monitored by TLC on Silica Gel FG254 (E. Merck, Darmstadt, Germany).

Example A

Solid-Phase Extraction of Lauroylated Intermediates

As indicated in the following examples, certain lauroylated reaction intermediates were purified by solid-phase extraction. In this purification procedure, the reaction mixture is concentrated, re-dissolved in methanol, and applied onto C18 silica (Waters Prep C18, 125 Å, 1 g per 20 mg lauroylated carbohydrate). The C18 silica is then washed with methanol (10 mL/g C18 silica) and the product is eluted with pentane (10 mL/g C18 silica). For L-arginine containing compounds, the reaction mixture is concentrated, re-dissolved in 70% methanol and applied onto C18 silica. The C18 silica is then washed with 70% methanol and the product is eluted with methanol. The resulting product contains no residual reagents as determined by TLC, $^1$H-nmr, or MALDI-TOF mass spectroscopy.

Example B

Synthesis of 1 2,3,4 6-Penta-O-lauroyl-α-D-galactopyranose 1

To a suspension of galactose (3.78 g, 21.0 mmol), pyridine (50 mL), and 4-dimethylaminopyridine (cat.) in pentane (150 mL) under argon atmosphere, was added lauroyl chloride (50 mL, 210 mmol) at −78° C. The mixture was allowed to reach ambient temperature. The resulting white slurry slowly dissolved and a fine precipitate of pyridinium hydrochloride formed. After 40 h, the pyridinium hydrochloride was filtered off and the pentane solution was concentrated. Column chromatography (SiO$_2$, pentane/EtOAc 9:1) gave 1 (16.0 g, 70% yield), [α]$_D^{25}$ +39°(c 0.9, CHCl$_3$). $^1$H-Nmr data (CHCl$_3$): δ6.39 (d, 1H, J 2.4 Hz, H-1), 5.51 (br s, 1H, H-4), 5.35 (m, 2H, H-2 and H-3), 4.32 (br t, 1H, J 6.6 Hz, H-5), 4.08 (d, 2H, J 6.6 Hz, H-6a and H-6b), 2.39, 2.38, 2.30, 2.26 (4 t, 2H each, J 7.5 Hz, —$CH_2CO$—), 2.21 (m, 2H, —$CH_2CO$—), 0.88 (t, 15 H, J 7.0 Hz, —$CH_3$). Anal. Calcd for $C_{66}H_{122}O_{11}$: C, 72.2; H, 11.3. Found: C, 72.6; H, 11.5.

Example C

Synthesis of 1-S-Acetyl-2,3,4 6-tetra-O-lauroyl-1-thio-β-D-galactopyranose (2)

Method 1:

To compound 1 (from Example B, 1 g, 0.91 mmol) and thiolacetic acid (0.4 mL, 9.1 mmol) in dry dichloromethane (5 mL) under argon at 0° C., was added boron trifluoride etherate (1.7 mL, 13.6 mmol). The cold-bath was removed after 10 min and after 24 h the mixture was diluted with dichloromethane, washed with saturated sodium bicarbonate, dried over sodium sulfate, and concentrated. Column chromatography ($SiO_2$, pentane/Et2O/EtOAc 9:1:1) gave 2 (0.60 g, 70% yield).

Method 2:

To compound 1 (from Example B, 276.5 mg, 0.253 mmol) in dry tetrahydrofuran (2.0 mL) under argon, was added benzylamine (27.9 μL, 0.255 mmol). The mixture was concentrated after 70 h. The residue was dissolved in dry dichloromethane (4.0 mL) under argon and then trichloroacetonitrile (250 μL, 2.5 mmol) and 1,8-diazabicyclo[5.4.0]undec-7-ene (30 μL, 0.2 mmol) were added. The mixture was concentrated after 3 h and the residue was flashed through a short column ($SiO_2$, pentane/EtOAc 19:1), then concentrated. To the residue in dry dichloromethane (3.5 mL) under argon, was added thiolacetic acid (1 mL). After 96 h, the reaction mixture was concentrated and the residue was purified by column chromatography ($SiO_2$, pentane, EtOAc 19:1) to give 2 (90 mg, 37% yield), $[\alpha]_D^{25}$ 21° (c 1, $CHCl_3$). $^1$H-Nmr data ($CHCl_3$): δ 5.47 (d, 1H, J 3.4 Hz, H-4), 5.32 (t, 1H, J 10.0 Hz, H-2), 5.25 (d, 1H, J 10.0 Hz, H-1), 5.12 (dd, 1H, J 3.4 and 10.0 Hz, H-3), 4.08 (m, 3H, H-5, H-6a and H-6b), 2.14–2.43 (m, 8H, —$CH_2CO$—), 2.37 (s, 3H, -SAc), 0.88 (t, 15 H, J 7.0 Hz, —$CH3$). Anal. Calcd for $C_{56}H_{102}O_{10}S$: C, 69.5; H, 10.6; S, 3.3. Found: C, 69.4; H, 10.8; S, 3.5.

Method 3:

To compound 1 (20.0 g, 18.2 mmol) and thioacetic acid (5.0 mL, 1.9 eq.) in dry dichloromethane (300 mL) under argon, was added trimethylsilyl trifluoromethanesulfonate (5.0 mL, 0.5 eq.) at 0° C. The cold-bath was immediately removed and after 48 h the mixture was diluted with dichloromethane, washed with saturated sodium hydrogen carbonate, dried ($Na_2SO_4$), and concentrated. Column chromatography ($SiO_2$, pentane/EtOAc 20:1) gave 2 (13.7 g, 77%), $[\alpha]_D^{25}$ +21° (c 1, $CHCl_3$). $^1$H-Nmr data ($CHCl_3$): δ 5.47 (d, 1H, J 3.4 Hz, H-4), 5.32 (t, 1H, J 10.0 Hz, H-2), 5.25 (d, 1H, J 10.0 Hz, H-1), 5.12 (dd, 1H, J 3.4 and 10.0 Hz, H-3), 4.08 (m, 3H, H-5, H-6a and H-6b), 2.14–2.43 (m, 8H, —$CH_2CO$—), 2.37 (s, 3H, —SAc), 0.88 (t, 15 H, J 7.0 Hz, —$CH_3$). Anal. Calcd for $C_{56}H_{102}O_{10}S$: C, 69.5; H, 10.6; S, 3.3. Found: C, 69.4; H, 10.8; S, 3.5.

Example C'

Synthesis of 1-S-Acetyl-2,3,4,6-tetra-O-lauroyl-1-thio-α-D-galactopyranose

Method 1:

To compound 1 (20.0 g, 18.2 mmol) and thioacetic acid (27.0 mL, 20 eq.) in dry toluene (80 mL) under argon was added tin (IV) chloride (21.3 mL) dropwise at room temperature. The reaction was monitored by Tlc carefully. After 1 h, 600 mL of 1M aqueous HCl was added to the vigorously stirred mixture and the resulting mixture was filtered through Celite to remove the emulsion of tin salts. The mixture was diluted with pentane (800 mL), washed with water (2×400 mL), saturated sodium hydrogen carbonate (300 mL) and water (300 mL), dried with $Na_2SO_4$ and concentrated. The residue was purified by column chromatography three times ($SiO_2$, pentane/EtOAc 20:1, 30:1, 40:1) to give 1-S-acetyl-2,3,4,6-tetra-O-lauroyl-1-thio-α-D-galactopyranose (3.65 g, 21%). $^1$H-Nmr data ($CHCl_3$): δ 6.26 (d, 1H, J 5.5 Hz, H-1), 5.47 (dd, 1H, J 11.0 Hz, 5.5 Hz, H-2), 5.46 (d, 1H, J 3.5 Hz, H-4), 5.04 (dd, 1H, J 11.0 Hz, 3.5 Hz, H-3), 4.17 (t, 1H, J 6.5 Hz, H-5), 4.06 (d, 2H, J 6.5 Hz, H-6a and H-6b), 2.38 (t, 8H, J 7.0 Hz, —$COCH_2$—), 2.40 (s, 3H, —SAc), 0.87 (t, 15H, J 7.0 Hz, —$CH_3$).

Method 2:

To compound 1 (25.0 g, 22.9 mmol) and thioacetic acid (8.5 mL, 114.5 mmol) in dry dichloromethane (100 mL) under argon, was added trimethylsilyl trifluoromethanesulfonate (5.6 mL, 45.8 mmol) at room temperature. After 20 h, the mixture was diluted with dichloromethane (600 mL), washed with saturated sodium hydrogen carbonate (250 mL) and water (2×200 mL), dried with $Na_2SO_4$ and concentrated. The residue was purified by column chromatography three times ($SiO_2$, pentane/EtOAc 20:1, 30:1, 40:1) to give 1-S-acetyl-2,3,4,6-tetra-O-lauroyl-1-thio-α-D-galactopyranose (1.59 g, 7.2%).

Example D

General Procedure for Michael Additions and α-Halocarbonyl Substitutions

To compound 2 (1 mmol) and an electrophile (1.2 mmol) in dry dichloromethane (8 mL) under argon, was added $Et_2NH$ (4 mL). After 1–3 h, the mixture was concentrated and the residue was purified by column chromatography on $SiO_2$ by eluting with pentane/EtOAc. The products were characterized with $^1$H-nmr spectroscopy and MALDI-TOF mass spectroscopy.

Example E

General Procedure for Reduction to Alcohols

To the product from Example D (100 μmol) in dry tetrahydrofuran (2.0 mL) and isopropanol (0.7 mL) under argon atmosphere, was added $NABH_4$ (150 μmol). After 0.5–3 h, the mixture was concentrated (acetic acid (about 40 μL) was added prior to concentration in some cases) and the residue was purified according to the solid-phase extraction procedure of Example A. The product alcohols were characterized with $^1$H-nmr spectroscopy and MALDI-TOF mass spectroscopy.

Example F

General Procedure for Reductive Amination to a Primary Amine

Method 1:

To the product from Example D (100 μmol) and ammonium acetate (75 mg, 1 mmol) in dry methanol (2.3 mL) and tetrahydrofuran (0.9 mL) under argon, was added $NaCNBH_3$ (100 μmol). After 1–72 h, the mixture was concentrated and the residue purified according to the solid-phase extraction procedure of Example A. The product amines were characterized with $^1$H-nmr spectroscopy and MALDI-TOF mass spectroscopy.

Method 2:

The product from Example D (200 mg, 0.198 mmol) and dry NH$_4$OAc (30 mg, 0.4 mmol) were stirred in dry MeOH (6 mL), dry 1,2-dichloroethane (6 mL), and trimethyl orthoformate (1 mL) under argon for 24 h (until TLC analysis showed that most of the starting material was consumed). NaBH$_4$ (10 mg, 0.26 mmol) was added and after 1 h the mixture was concentrated. The residue was purified according to the solid-phase extraction procedure of Example A to provide the primary amine (containing traces of the corresponding alcohol). This mixture was dissolved in pentane/EtOAc (1:1) and applied onto a Waters Sep-Pak Plus Longbody SiO$_2$ cartridge. The cartridge was washed with pentane/EtOAc (1:1, 20 mL) (to remove the corresponding alcohol), followed by elution with toluene/EtOH (9:1, 30 mL) to afford the primary amine.

Example G

General Procedure for Acylation of Primary Amines with Phthalic Anhydride

The -O-lauroylated primary amine from Example F (100 μmol), phthalic anhydride (2.7 mmol), and 4-(N,N-dimethylamino)pyridine (catalytic) were dissolved in dry pyridine. The mixture was concentrated after 12–48 h and the residue purified according to the solid-phase extraction procedure of Example A. The product 2-carboxybenzamides were characterized with $^1$H-nmr spectroscopy and MALDI-TOF mass spectroscopy.

Example H

General Procedure for Reductive Amination with Amino Acids

To the product from Example D (100 μmol) and an amino acid tert-butyl ester hydrochloride or methyl ester hydrochloride (1 mmol) in dry MeCN (2.25 mL) and THF (0.75 mL), was added NaCNBH$_3$ (100 μmol). After 1–72 h, the mixture was concentrated and the residue was purified according to the solid-phase extraction procedure of Example A. The product N-alkylated amino acids were characterized with $^1$H-nmr spectroscopy and MALDI-TOF mass spectroscopy.

Example I

General Procedure for Deblocking of Alcohols

To the lauroylated alcohol from Example E (100 μmol) in dry methanol (7.1 mL) and dichloromethane (1.4 mL) under argon atmosphere, was added methanolic sodium methoxide (1 M, 50 μL). After 1–24 h, the mixture was neutralized with Amberlite IR-50S (H$^+$) resin, filtered and concentrated. The residue was dissolved in water and applied onto a column of C18 silica (Waters Prep C18, 125 Å, 5 g). The C18 silica was washed with water (50 mL), and the product was then eluted with 70% methanol (50 mL). The resulting alcohols were characterized with $^1$H-nmr spectroscopy and MALDI-TOF mass spectroscopy.

Example J

General Procedure for Deblockinz of Primary Amines

To the -O-lauroylated primary amine from Example F (100 μmol) in dry methanol (7.1 mL) and dichloromethane (1.4 mL) under argon, was added methanolic sodium methoxide (1 M, 50 μL). After 1–24 h, the mixture was neutralized with Amberlite IR-50S (H$^+$) resin, filtered and concentrated. The residue was dissolved in dichloromethane/methanol 2:1 and applied to a Waters SepPak Plus Longbody SiO$_2$ cartridge. The cartridge was washed with dichloromethane/methanol (2:1) and then the product was eluted with dichloromethane/methanol/water (5:5:1) (20 mL) and concentrated. The residue was dissolved in water and applied onto a column of C18 silica (Waters Prep C8, 125 Å, 5 g). The C18 silica was washed with water (50 mL) and then the product was eluted with methanol (50 mL). The resulting primary amines were characterized with $^1$H-nmr spectroscopy and MALDI-TOF mass spectroscopy.

Example K

General Procedure for N-Acetylation of Primary Amines

To the primary amine from Example J (100 μmol) in moist methanol (4.4 mL) was added acetic anhydride (0.4 mL). The mixture was concentrated after 2–24 h, re-dissolved in water and applied to a column of C18 silica (Waters Prep C18, 125 Å, 5 g). The C18 silica was washed with water (50 mL) and then the product was eluted with methanol (50 mL). The resulting acetamides were characterized with $^1$H-nmr spectroscopy and MALDI-TOF mass spectroscopy.

Example L

General Procedure for Deblocking of 2-Carboxybenzamides

To the -O-lauroylated 2-carboxybenzamide from Example G (100 μmol) in dry methanol (7.1 mL) and dichloromethane (1.4 mL) under argon, was added methanolic sodium methoxide (1 M, 50 μL). After 1–24 h, the mixture was neutralized with Amberlite IR-50S (H$^+$) resin, filtered and concentrated. The residue was dissolved in dichloromethane/methanol (8:1) and applied to a Waters SepPak Plus Longbody SiO$_2$ cartridge. The cartridge was washed with dichloromethane/methanol (8:1) and then the product was eluted with dichloromethane/methanol/water (65:35:5) (20 mL) and concentrated. The residue was dissolved in water and applied to a column of C18 silica (Waters Prep C18, 125 Å, 5 g). The C18 silica was washed with water (50 mL), and then the product was eluted with methanol (50 mL). The resulting 2-carboxybenzamides were characterized with $^1$H-nmr spectroscopy and MALDI-TOF mass spectroscopy.

Example M

General Procedure for Deblocking of N-Alkylated Glycine, β-Alanine, and L-Leucine Compounds The N-alkylated amino acid tert-butyl ester from Example H (100 μmol) was treated with trifluoroacetic acid (3.5 mL) in dry dichloromethane (3.5 mL) for 1–10 h. n-Propyl acetate (8 mL) and toluene (16 mL) were added and the mixture was concentrated, then co-concentrated twice with toluene. To the residue in dry methanol (7.1 mL) and dichloromethane (1.1 mL) under an argon atmosphere was added methanolic sodium methoxide (1 M, 200 μL). After 1–24 h, the mixture was neutralized with Amberlite IR-50S (H$^+$) resin, filtered and concentrated. The residue was dissolved in dichloromethane/methanol (9:1) and applied to a Waters SepPak Plus Longbody SiO$_2$ cartridge. The cartridge was washed with dichloromethane/methanol (9:1) and then the product was eluted with dichloromethane/methanol/water (65:35:5) (20 mL) and concentrated. The residue was dissolved in water and applied to a column of C18 silica (Waters Prep C18, 125 Å, 5 g). The C18 silica was washed with water (50 mL) and then the product was eluted with 70% methanol (50 mL). The resulting N-alkylated glycine, β-alanine, and L-leucine compounds were characterized with $^1$H-nmr spectroscopy and MALDI-TOF mass spectroscopy.

Example N

General Procedure for Deblocking of N-Alkylated L-Histidine and L-Tryptophan Compounds To the N-alkylated amino acid methyl ester from Example H (100 µmol) in dry methanol (7.3 mL) and dichloromethane (1.1 mL) under an argon atmosphere was added methanolic sodium methoxide (1 M, 50 µL). After 1–24 h, the mixture was neutralized with Amberlite IR-50S (H$^+$) resin, filtered and concentrated. The residue was dissolved in 70% methanol and applied to a column of C18 silica (Waters Prep C18, 125 Å, 5 g) and then the product was eluted with 70% methanol (50 mL). To the residue in water (3.7 mL) was added aqueous lithium hydroxide (1M, 0.3 mL). After 0.5–2 h, the mixture was neutralized with Amberlite IR-50S (H$^+$) resin, filtered and concentrated. The residue was dissolved in dichloromethane/methanol (9:1) and applied to a Waters SepPak Plus Longbody SiO$_2$ cartridge. The cartridge was washed with dichloromethane/methanol (9:1) and then the product was eluted with dichloromethane/methanol/water (65:35:5) (20 mL) and concentrated. The residue was dissolved in water and applied to a column of C18 silica (Waters Prep C18, 125 Å, 5 g). The C18 silica was washed with water (50 mL), and the product was eluted with 70% methanol (50 mL). The resulting N-alkylated L-histidine and L-tryptophan compounds were characterized with $^1$H-nmr spectroscopy and MALDI-TOF mass spectroscopy.

Example O

General Procedure for Deblocking of N-Alkylated L-Arginine Compounds

To the N-alkylated arginiiie methyl ester from Example H (100 µmol) in dry methanol (7.3 mL) and dichloromethane (1.1 mL) under an argon atmosphere was added methanolic sodium methoxide 1M, 50 µL). After 1–24 h, the mixture was neutralized with Amberlite IR-50S (H$^+$) resin, filtered and concentrated. The residue was dissolved in 70% methanol and applied to a column of C18 silica and then the product was eluted with 70% methanol (50 mL). To the residue in water (3.7 mL) wa then added aqueous lithium hydroxide (1M, 0.3 mL). After 0.5–2 h, the mixture was neutralized with Amberlite IR-50s (H$^+$) resin, filtered and concentrated. The residue was dissolved in water and applied to column of C18 silica (Waters Prep C18, 125 Å, 5 g). The C18 silica was washed with water (50 mL) and then the product was eluted with 50% methanol (50 mL). The resulting N-alkylated L-arginine compounds were characterized with $^1$H-nmr spectroscopy and MALDI-TOF mass spectroscopy.

Example P

General Procedure for the Preparation of Mesylates

To the alcohol from Example D (0.3 mmol) in dry tetrahydrofuran (2 mL) and dry pyridine (4 mL) under an argon atmosphere was added methanesulfonyl chloride (0.5 mL). After 12–24 h, the mixture was washed with 0.5M HCl and extracted with pentane. The pentane extracts were concentrated and the residue was purified on C18-silica to afford the mesylate derivative.

Example Q

General Procedure for the Preparation of Azido Compounds

To the mesylate from Example P (0.2 mmol) in dry DMF (8 mL) and dry THF (3 mL) under an argon atmosphere at 60° C. was added sodium azide (5 mmol) and 18-crown-6 (180 mg). After 2 hours, the reaction mixture was concentrated and the residue was purified on C18-silica. In some cases, the product was re-chromatographed with silica gel using pentane/EtOAc (9:1) as the eluant to afford the azido derivative.

Example R

General Procedure for Reduction of Azido Groups to Primary Amines

To a solution of the azido compound from Example S (15 µmol) in dry isopropanol (1 mL) and dry ethanol (1 mL) under an argon atmosphere, was added NaBH$_4$ (15 µmol) and NiCl$_2$ (30 µmol). After 1 hour, the reaction mixture was neutralized with acetic acid (1 drop), concentrated and purified on C18-silica to afford the primary amine.

Example S

General Procedure for Reductive Alkylation of Primary Amines

To the primary amine from Example F or S (6.8 µmol) in dry methanol (1 mL) and dry dichloromethane (1 mL) under an argon atmosphere was added an aldehyde or ketone (3.4 mmol) and sodium triacetoxyborohydride (47 µmol). After 24–48 hours, toluene (1 mL) was added and the mixture was concentrated and the residue purified on C18-silica gel.

Example T

General Procedure for Reductive Amination

To the product from Example D (0.1 mmol) and a primary amine (0.45 mmol) in dry dichloromethane (2 mL), methanol (2 mL) and triethylorthoformate (1 mL) under argon, was added NaCNBH$_3$ (1 mmol). After 24 h, the mixture was concentrated and dissolved in toluene (1 mL) and purified on C18-silica gel (5 g).

Example U

General Procedure for Deblocking of Secondary Amines

To the -O-lauroylated secondary amine from Example S or T (100 µmol) in dry methanol (7.1 mL) and dichloromethane (1.4 mL) under argon, was added methanolic sodium methoxide 1M, 50 µL). After 1–24 h, the mixture was neutralized with Amberlite IR-50S (H$^+$) resin, filtered and concentrated. The residue was dissolved in dichloromethane/methanol 2:1 and applied to a Waters Sep-Pak Plus Longbody SiO$_2$ cartridge. The cartridge was washed with dichloromethane/methanol (2:1) and then the product was eluted with dichloromethane/methanol/water (5:5:1) (20 mL) and concentrated. The residue was dissolved in water and applied onto a column of C18 silica (Waters Prep C18, 125 Å, 5 g). The C18 silica was washed with water (50 mL) and then the product was eluted with methanol (50 mL). The resulting secondary amines were characterized with 1H-nmr spectroscopy and MALDI-TOF mass spectroscopy.

Example A1

Synthesis of 2-Hydroxycyclopent-1-yl 1-Thio-β-D-galactopyranoside

The title compound was prepared according to procedures D, E and I above using 2-chlorocyclopentanone as the electrophile. Mass spectra data was as follows: M (calcd.): 280.34; M (found): 304.9 (M+Na$^+$). Selected nmr data was as follows: $^1$H-nmr (CD$_3$OD): δ4.44 (H-1), 4.42, 4.38, and 4.35.

Example A2

Synthesis of 2-Hydroxycyclohex-1-yl 1-Thio-β-D-galactopyranoside

The title compound was prepared according to procedures D, E and I above using 2-chlorocyclohexanone as the electrophile. Mass spectra data was as follows: M (calcd.): 294.34; M (found): 318.8 (M+Na$^+$). Selected nmr data was as follows: $^1$H-nmr (CD$_3$OD): δ4.55 (H-1), 4.43, 4.39, and 4.34.

Example A3

Synthesis of 3-Hydroxy-1-phenylbut-1-yl 1-Thio-β-D-galactopyranoside

The title compound was prepared according to procedures D, E and I above using 4-phenylbut-3-en-2-one as the electrophile. Mass spectra data was as follows: M (calcd.): 345.43; M (found): 368.0 (M+Na$^+$). Selected nmr data was as follows: $^1$H-nmr (CD$_3$OD): δ4.45 (H-1), 4.43, 4.31, and 4.25.

Example A4

Synthesis of (3-Hydroxynorborn-2-yl)methyl 1-Thio-β-D-galactopyranoside

The title compound was prepared according to procedures D, E and I above using 3-methylene-2-norbornanone as the electrophile. Mass spectra data was as follows: M (calcd.): 320.41; M (found): 344.6 (M+Na$^+$). Selected nmr data was as follows: $^1$H-nmr (CD$_3$OD): δ4.30 (H-1) and 4.29.

Example A5

Synthesis of 3-Hydroxycyclohept-1-yl 1-Thio-β-D-galactopyranoside

The title compound was prepared according to procedures D, E and I above using cyclohept-en-1-one as the electrophile. Mass spectra data was as follows: M (calcd.): 308.40; M (found): 332.1 (M+Na$^+$). Selected nmr data was as follows: $^1$H-nmr (CD$_3$OD): δ4.394 (H-1), 4.389, and 4.381.

Example A5'

Synthesis of 3-Hydroxycyclohept-1-yl 1-Thioa-α-D-galactopyranoside

The title compound was prepared according to procedures D, E and I above using 1-S-acetyl-2,3,4,6-tetra-O-lauroyl-1-thio-α-D-galactopyranose (from Example C'above) and cyclohept-en-1-one as the electrophile. Mass spectra data was as follows: M (calcd.): 308.40; M (found): 331.3 (M+Na$^+$). Selected nmr data was as follows: $^1$H-nmr (CD$_3$OD): δ5.44 (d, J 5.8 Hz, H-1) and 5.45 (d, J 5.8 Hz, H-1).

Example A6

Synthesis of 2,2-Dimethyl-4-hydroxycyclopent-1-yl 1-Thio-β-D-galactopyranoside

The title compound was prepared according to procedures D, E and I above using 4,4-dimethylcyclopent-2-en-1-one as the electrophile. Mass spectra data was as follows: M (calcd.): 308.40; M (found): 332.1 (M+Na$^+$). Selected nmr data was as follows: $^1$H-nmr (CD$_3$OD): δ4.34 (H-1), 4.315, 4.310, and 4.305.

Example A7

Synthesis of 3-Hydroxycyclopent-1-yl 1-Thio-β-D-galactopyranoside

The title compound was prepared according to procedures D, E and I above using cyclopent-2-en-1-one as the electrophile. Mass spectra data was as follows: M (calcd.): 280.34; M (found): 304.9 (M+Na$^+$). Selected nmr data was as follows: $^1$H-nmr (CD$_3$OD): δ4.36 (H-1), 4.355, and 4.34.

Example A8

Synthesis of 4Hydroxypent-2-yl 1-Thio-β-D-galactopyranoside

The title compound was prepared according to procedures D, E and I above using pent-3-en-2-one as the electrophile. Mass spectra data was as follows: M (calcd.): 282.35; M (found): 305.3 (M+Na$^+$). Selected nmr data was as follows: $^1$H-nmr (CD$_3$OD): β 4.42 (H-1), 4.41, and 4.39.

Example A9

Synthesis of 2,2-Dimethyl-5-hydroxycyclohex-1-yl 1-Thio-β-D-galactopyranoside

The title compound was prepared according to procedures D, E and I above using 4,4-dimethylcyclohex-2-en-1-one as the electrophile. Mass spectra data was as follows: M (calcd.): 322,42; M (found): 346.6 (M+Na$^+$). Selected nmr data was as follows: $^1$H-nmr (CD$_3$OD): δ4.34 (H-1), 4.33, and 4.32.

Example A10

Synthesis of 3-Hydroxycyclohex-1-yl 1-Thio-β-D-galactopyranoside

The title compound was prepared according to procedures D, E and I above using cyclohex-2-en-1-one as the electrophile. Mass spectra data was as follows: M (calcd.): 294.37; M (found): 317.3 (M+Na$^+$). Selected nmr data was as follows: $^1$H-nmr (CD$_3$OD): δ4.422 (H-1), 4.417, and 4.38.

Example A11

Synthesis of 4,4Dimethyl-3-hydroxycyclohex-1-yl 1-Thio-β-D-galactopyranoside

The title compound was prepared according to procedures D, E and I above using 6,6-dimethylcyclohex-2-en-1-one as the electrophile.

Example B1

Synthesis of 2-Aminocyclopent-1-yl 1-Thio-β-D-galactopyranoside

The title compound was prepared according to procedures D, F and J above using 2-chlorocyclopentanone as the electrophile. Mass spectra data was as follows: M (calcd.): 279.36; M (found): 276.3 (M+H$^+$). Selected nmr data was as follows: $^1$H-nmr (CD$_3$OD): δ4.46 (H-1), 4.45, 4.37 and 4.27.

Example B2

Synthesis of 2-Aminocyclohex-1-yl 1-Thio-β-D-galactopyranoside

The title compound was prepared according to procedures D, F and J above using 2-chlorocyclohexanone as the electrophile. Mass spectra data was as follows: M (calcd.): 293.38; M (found): 295.8 (M+H$^+$), and 319.7 (M+Na$^+$). Selected nmr data was as follows: $^1$H-nmr (CD$_3$OD): δ4.48 (H-1), 4.44, 4.40 and 4.30.

Example B3

Synthesis of 3-Amino-1-phenylbut-1-yl 1-Thio-β-D-galactopyranoside

The title compound was prepared according to procedures D, F and J above using 4-phenylbut-3-en-2-one as the electrophile. Mass spectra data was as follows: M (calcd.): 344.45; M (found): 345.1 (M+H$^+$). Selected nmr data was as follows: $^1$H-nmr (CD$_3$OD): δ4.41 (H-1), 4.12, and 3.90.

Example B4

Synthesis of (3-Aminonorborn-2-yl)methyl 1-Thio-β-D-galactopyranoside

The title compound was prepared according to procedures D, F and J above using 3-methylene-2-norbornanone as the electrophile. Mass spectra data was as follows: M (calcd.): 319.42; M (found): 321.6 (M+H$^+$). Selected nmr data was as follows: $^1$H-nmr (CD$_3$OD): δ4.42 (H-1), 4.41, 4.38, and 4.35.

Example B5

Synthesis of 3-Aminocyclohept-1-yl 1-Thio-β-D-galactopyranoside

The title compound was prepared according to procedures D, F and J above using cyclohept-2-en-1-one as the electrophile. Mass spectra data was as follows: M (calcd.): 307.41; M (found): 333.0 (M+Na$^+$). Selected nmr data was as follows: $^1$H-nmr (CD$_3$OD): δ4.41 (H-1), 4.39, and 4.38.

Example B6

Synthesis of 2,2-Dimethyl-4aminocyclopent-1-yl 1-Thio-β-D-galactopyranoside

The title compound was prepared according to procedures D, F and J above using 4,4-dimethylcyclopent-2-en-1-one as the electrophile. Mass spectra data was as follows: M (calcd.): 307.41; M (found): 307.2 (M+H$^+$). Selected nmr data was as follows: $^1$H-nmr (CD$_3$OD): δ4.35 (H-1), 4.33, 4.32, and 4.30.

Example B6A

Synthesis of 2,2-Dimethyl-4- (methylamino)-cyclopent-1-yl 1-Thio-β-D-galactopyranoside The title compound was prepared according to procedures D, T and U above using 4,4-dimethylcyclopent-2-en-1-one as the electrophile and methylamine as the primary amine. Mass spectra data was as follows: M (calcd.): 321.43; M (found): 322.7 (M+H$^+$). Selected nmr data was as follows: $^1$H-nmr (CD$_3$OD): δ4.325 (H-1), 4.315, 4.308, 4.304.

Example B6B

Synthesis of 2,2-Dimethyl-4(isopropylamino)-cyclopent-1-yl 1-Thio-β-D-galactopyranoside The title compound was prepared according to procedures D, T and U above using 4,4-dimethylcyclopent-2-en-1-one as the electrophile and isopropylamine as the primary amine. Mass spectra data was as follows: M (calcd.): 349.48: M (found): 350.7 (M+H$^+$). Selected nmr data was as follows: $^1$H-nmr (CD$_3$OD): δ4/460 (H-1), 4.401, 4.400, 4.391.

Example B6C

Synthesis of 2,2-Dimethyl-4(n-propylamino)-cyclopent-1-yl 1-Thio-β-D-galactopyranoside The title compound was prepared according to procedures D, T and U above using 4,4-dimethylcyclopent-2-en-1-one as the electrophile and n-propylamine as the primary amine. Mass spectra data was as follows: M (calcd.): 349.49; M (found): 350.5 (M+H$^+$). Selected nmr data was as follows: $^1$H-nmr (CD$_3$OD): δ4.324 (H-1), 4.317, 4.310, 4.307.

Example B6D

Synthesis of 2,2-Dimethyl-4((R)-sec-butylamino)-cyclopent-1-yl 1-Thio-β-D-galactopyranoside The title compound was prepared according to procedures D, T and U above using 4,4-dimethylcyclopent-2-en-1-one as the electrophile and (R)-(−)-sec-butylamine as the primary amine. Mass spectra data was as follows: M (calcd.): 364.52; M (found): 364.6 (M+H$^+$). Selected nmr data was as follows: $^1$H-nmr (CD$_3$OD): δ 4.328 (H-1), 4.319, 4.313, 4.311.

Example B6E

Synthesis of 2,2-Dimethyl-4-((S)-sec-butylamino)-cyclopent-1-yl 1-Thio-β-D-galactopyranoside The title compound was prepared according to procedures D, T and U above using 4,4-dimethylcyclopent-2-en-1-one as the electrophile and (S)-(+)-sec-butylamine as the primary amine. Mass spectra data was as follows: M (calcd.): 364.52; M (found): 364.6 (M+H$^+$). Selected nmr data was as follows: $^1$H-nmr (CD$_3$OD): δ4.333 (H-1), 4.330, 4.300, 4.290.

Example B6F

Synthesis of 2,2-Dimethyl-4-(pent-3-ylamino)-cyclopent-1-yl 1-Thio-β-D-galactopyranoside The title compound was prepared according to procedures D, T and U above using 4,4-dimethylcyclopent-2-en-1-one as the electrophile and 3-pentylamine as the primary amine. Mass spectra data was as follows: M (calcd.): 377.53; M (found): 376.7 (M+H$^+$). Selected nmr data was as follows: $^1$H-nmr (CD$_3$OD): δ4.333 (H-1), 4.329, 4.300, 4.290.

Example B6G

Synthesis of 2,2-Dimethyl-4-(n-hexylamino)-cyclopent-1-yl 1-Thio-β-D-galactopyranoside The title compound was prepared according to procedures D, T and U above using 4,4-dimethylcyclopent-2-en-1-one as the electrophile and n-hexylamine as the primary amine. Mass spectra data was as follows: M (calcd.): 391.57; M (found): 394.3 (M+H$^+$). Selected nmr data was as follows: $^1$H-nmr (CD$_3$OD): δ4.336 (H-1), 4.332, 4.303, 4.291.

Example B6H

Synthesis of 2,2-Dimethyl-4-(cyclobut-1-ylamino)-cyclopent-1-yl 1-Thio-β-D-galactopyranoside The title compound was prepared according to procedures D, T and U above using 4,4-dimethylcyclopent-2-en-1-one as the electrophile and cyclobutyl amine as the primary amine. Mass spectra data was as follows: M (calcd.): 361.50; M (found): 361.6 (M+H$^+$). Selected nmr data was as follows: $^1$H-nmr (CD$_3$OD): δ4.315 (H-1), 4.300, 4.292, 4.290.

Example B6I

Synthesis of 2,2-Dimethyl-4-(3,3-dimethylcyclobut-1-ylamino)-cyclopent-1-yl 1-Thio-β-D-galactopyranoside The title compound was prepared according to procedures D, T and U above using 4,4-dimethylcyclopent-2-en-1-one as the electrophile and 3,3-dimethylcyclobut-1-ylamine as the primary amine. Mass spectra data was as follows: M (calcd.): 389.55; M (found): 392.2 (M+H$^+$). Selected nmr data was as follows: $^1$H-nmr (CD$_3$OD): δ4.324 (H-1), 4.311, 4.305, 4.294.

Example B6J

Synthesis of 2,2-Dimethyl-4-(cyclopent-1-ylamino)-cyclopent-1-yl 1-Thio-β-D-galactopyranoside The title compound was prepared according to procedures D, T and U above using 4,4-dimethylcyclopent-2-en-1-one as the electrophile and cyclopentylamine as the primary amine. Mass spectra data was as follows: M (calcd.): 375.52; M (found): 376.6 (M+H$^+$). Selected nmr data was as follows: $^1$H-nmr (CD$_3$OD): δ 4.322 (H-1), 4.310, 4.304, 4.295.

Example B6K

Synthesis of 2,2-Dimethyl-4-(cyclohex-1-ylamino)-cyclopent-1-yl 1-Thio-β-D-galactopyranoside The title compound was prepared according to procedures D, T and U above using 4,4-dimethylcyclopent-2-en-1-one as the electrophile and cyclohexylamine as the primary amine. Mass spectra data was as follows: M (calcd.): 389.55; M (found): 391.2 (M+H$^+$). Selected nmr data was as follows: $^1$H-nmr (CD$_3$OD): δ4.319 (H-1), 4.310, 4.307, 4.293.

Example B6L

Synthesis of 2,2-Dimethyl-4-(4-methylcyclohex-1-ylamino)-cyclopent-1-yl 1-Thio-β-D-galactopyranoside The title compound was prepared according to procedures D, T and U above using 4,4-dimethylcyclopent-2-en- 1-one as the electrophile and 4-methylcyclohex-1-ylamine as the primary amine. Mass spectra data was as follows: M (calcd.): 403.47; M (found): 404.8 (M+H$^+$). Selected nmr data was as follows: $^1$H-nmr (CD$_3$OD): δ4.333 (H-1), 4.312, 4.300, 4.295.

Example B6Q

Synthesis of 2,2-Dimethyl-4-(3-methylcyclopent-1-ylamino)-cyclopent-1-yl 1-Thio-β-D-galactopyranoside The title compound was prepared according to procedures D, T and U above using 4,4-dimethylcyclopent-2-en-1-one as the electrophile and 3-methylcyclopent-1-ylamine as the primary amine. Mass spectra data was as follows: M (calcd.): 389.55; M (found): 390.7 (M+H$^+$). Selected nmr data was as follows: $^1$H-nmr (CD$_3$OD): δ 4.383 (H-1), 4.325, 4.300, 4.292.

Example B6R

Synthesis of 2,2-Dimethyl-4-(3,3-dimethylcyclopent-1-ylamino)-cyclopent-1-yl 1-Thio-β-D-galactopyranoside The title compound was prepared according to procedures D, T and U above using 4,4-dimethylcyclopent-2-en-1-one as the electrophile and 3,3-dimethylcyclopent-1-ylamine as the primary amine. Mass spectra data was as follows: M (calcd.): 4.295; M (found): 404.3 (M+H$^+$). Selected nmr data was as follows: $^1$H-nmr (CD$_3$OD): δ4.322 (H-1), 4.305, 4.300, 4.295.

Example B6T

Synthesis of 2,2-Dimethyl-4-(3-methylcyclohex-1-ylamino)-cyclopent-1-yl 1-Thio-β-D-galactopyranoside The title compound was prepared according to procedures D, T and U above using 4,4-dimethylcyclopent-2-en- 1-one as the electrophile and 3-methylcyclohex- 1-ylamine as the primary amine. Mass spectra data was as follows: M (calcd.): 403.57; M (found): 404.8 (M+H$^+$). Selected nmr data was as follows: $^1$H-nmr (CD$_3$OD): δ 4.326 (H-1), 4.313, 4.303, 4.294.

Example B7

Synthesis of 3-Aminocyclopent-1-yl 1-Thio-β-D-galactopyranoside

The title compound was prepared according to procedures D, F and J above using cyclopent-2-en-1-one as the electrophile. Mass spectra data was as follows: M (calcd.): 279.35; M (found): n.a. Selected nmr data was as follows: 1H-nmr (CD$_3$OD): δ4.46, 4.40, 4.38, and 4.34 (4 d, J 10 Hz), 3.88 (br s), 2.61, 2.27, 2.15, 1.82, and 1.64 (5 m).

Example B8

Synthesis of 4-Aminopent-2-yl 1-Thio-β-D-galactopyranoside

The title compound was prepared according to procedures D, F and J above using pent-3-en-2-one as the electrophile. Mass spectra data was as follows: M (calcd.): 281.37; M (found): 283.4 (M+H$^+$). Selected nmr data was as follows: $^1$H-nmr (CD$_3$OD): δ4.41 (H-1), 4.40, and 4.36.

Example B10

Synthesis of 3-Aminocyclohex-1-yl 1-Thio-β-D-galactopyranoside

The title compound was prepared according to procedure D, F and J above using cyclohex-2-en-1-one as the electrophile. Mass spectra data was as follows: M (calcd.): 293.38; M (found): 317.9 (M+Na$^+$). Selected nmr data was as follows: $^1$H-nmr (CD$_3$OD): δ4.54 (H-1), 4.52, 4.49, and 4.47.

Example B 11

Synthesis of 3-Amino-4,4-dimethylcyclohex-1-yl 1-Thio-β-D-galactopyranoside

The title compound was prepared according to procedure D, F and J above using 6,6-dimethylcyclohex-2-en-1-one as the electrophile.

Example C1

Synthesis of 2-Acetamidocyclopent-1-yl 1-Thio-β-D-galactopyranoside

The title compound was prepared according to procedures D, F, J and K above using 2-chlorocyclopent-1-one as the electrophile. Mass spectra data was as follows: M (calcd.): 321.39; M (found): 345.8 (M+Na$^+$). Selected nmr data was as follows: $^1$H-nmr (CD$_3$OD): δ4.53 (H-1), 4.44, 4.32, and 4.24.

Example C2

Synthesis of 2-Acetamidocyclohex-1-yl 1-Thio-β-D-galactopyranoside

The title compound was prepared according to procedures D, F, J and K above using 2-chlorocyclohexan-1-one as the electrophile. Mass spectra data was as follows: M (calcd.): 335.42; M (found): 359.4 (M+Na$^+$). Selected nmr data was as follows: $^1$H-nmr (CD$_3$OD): δ4.43 (H-1), 4.42, 4.32, and 4.29.

Example C3

Synthesis of 3-Acetamido-1-phenylbut-1-yl 1-Thio-β-D-galactopyranoside

The title compound was prepared according to procedures D, F, J and K above using 4-phenylbut-3-en-2-one as the electrophile. Mass spectra data was as follows: M (calcd.): 386,48; M (found): 408.3 (M+Na$^+$). Selected nmr data was as follows: $^1$H-nmr (CD$_3$OD): δ4.32 (H-1), 4.25, 3.83, and 3.79.

Example C5

Synthesis of 3-Acetamidocyclohept-1-yl 1-Thio-β-D-galactopyranoside

The title compound was prepared according to procedures D, F, J and K above using cyclohept-2-en-1-one as the electrophile. Mass spectra data was as follows: M (calcd.): 349.42; M (found): 372.5 (M+Na$^+$). Selected nmr data was as follows: $^1$H-nmr (CD$_3$OD): δ4.403 (H-1), 4.397, 4.34, and 4.33.

Example C7

Synthesis of 3-Acetamidocyclopent-1-yl 1-Thio-β-D-galactopyranoside

The title compound was prepared according to procedures D, F, J and K above using cyclopent-2-en-1-one as the electrophile. Mass spectra data was as follows: M (calcd.): 321.39; M (found): 349.5 (M+Na$^+$).

Example C8

Synthesis of 4-Acetamidopent-2-yl 1-Thio-β-D-galactopyranoside

The title compound was prepared according to procedures D, F, J and K above using pent-3-en-2-one as the electrophile. Mass spectra data was as follows: M (calcd.): 323.40; M (found): 347.7 (M+Na$^+$). Selected nmr data was as follows: $^1$H-nmr (CD$_3$OD): δ4.42 (H-1), 4.38, 4.37, and 4.35.

Example C10

Synthesis of 3-Acetamidocyclohexyl 1-Thio-β-D-galactopyranoside

The title compound was prepared according to procedures D, F, J and K above using cyclohex-2-en-1-one as the electrophile. Mass spectra data was as follows: M (calcd.): 335.42; M (found): 373.7 (M+Na$^+$). Selected nmr data was as follows: $^1$H-nmr (CD$_3$OD): δ4.52 (H-1), 4.464, and 4.455.

Example C11

Synthesis of 3-Acetamido-4,4-dimethylcyclohexyl 1-Thio-β-D-galactopyranoside

The title compound was prepared according to procedures D, F, J and K above using 6,6-dimethylcyclohex-2-en-1-one as the electrophile.

Example D1

Synthesis of 2-(2-Carboxybenzamido)cyclopent-1-yl 1-Thio-β-D-galactopyranoside

The title compound was prepared according to procedures D, F, G and L above using 2-chlorocyclopentan-1-one as the electrophile. Mass spectra data was as follows: M (calcd.): 427.47; M (found): 450.5 (M+H$^+$). Selected nmr data was as follows: $^1$H-nmr (CD$_3$OD): δ4.69 (H-1), 4.58, 4.27, and 4.22.

Example D2

Synthesis of 2-(2-Carboxybenzamido)cyclohex-1-yl 1-Thio-β-D-galactopyranoside

The title compound was prepared according to procedures D, F, G and L above using 2-chlorocyclohexan-l-one as the electrophile. Mass spectra data was as follows: M (calcd.): 441.50; M (found): 465.9 (M+Na$^+$). Selected nmr data was as follows: $^1$H-nmr (CD$_3$OD): δ4.54 (H-1), 4.52, 4.50, and 4.35.

Example D3

Synthesis of 3-(2-Carboxybenzamido)-1-phenylbut-1-yl 1-Thio-β-D-galactopyranoside The title compound was prepared according to procedures D, F, G and L above using 4-phenylbut-3-en-2-one as the electrophile. Mass spectra data was as follows: M (calcd.): 492.56; M (found): 513.0 (M+Na$^+$). Selected nmr data was as follows: $^1$H-nmr (CD$_3$OD): δ4.41 (H-1), 4.115, 4.110, and 3.90.

Example D4

Synthesis of [3-(Carboxybenzamido)norborn-2-yl] methyl 1-Thio-β-D-galactopyranoside The title compound was prepared according to procedures D, F, G and L above using 3-methylene-2-norbornanone as the electrophile. Mass spectra data was as follows: M (calcd.): 467.54; M (found): 492.9 (M+Na$^+$). Selected nmr data was as follows: $^1$H-nmr (CD$_3$OD): δ4.39 (H-1), 4.34, 4.31, and 4.26.

Example D5

Synthesis of 3-(2-Carboxybenzamido)cyclohept-1-yl 1-Thio-βD-galactopyranoside

The title compound was prepared according to procedures D, F, G and L above using cyclohept-2-en-1-one as the electrophile. Mass spectra data was as follows: M (calcd.): 453.52; M (found): 479.6 (M+Na$^+$). Selected nmr data was as follows: $^1$H-nmr (CD$_3$OD): δ4.53 (H-1), 4.51, 4.42, and 4.40.

Example D8

Synthesis of 3-(2-Carboxybenzamido)pent-2-yl 1-Thio-β-D-galactopyranoside

The title compound was prepared according to procedures D, F, G and L above using pent-3-en-2-one as the electrophile. Mass spectra data was as follows: M (calcd.): 429.48; M (found): 452.7 (M+Na$^+$). Selected nmr data was as follows: $^1$H-nmr (CD$_3$OD): δ4.42 (H-1), 4.41, 4.40, and 4.35.

Example D9

Synthesis of 5-(2-Carboxybenzamido)-2,2-dimethylcyclohex-1-yl 1-Thio-β-D-galactopyranoside The title compound was prepared according to procedures D, F, G and L above using 4,4-dimethylcyclohex-2-en-1-one as the electrophile. Mass spectra data was as follows: M (calcd.): 469.55, M (found): 492.4 (M+Na$^+$).

Example D10

Synthesis of 3-(2-Carboxybenzamido)cyclohex-1-yl 1-Thio-β-D-galactopyranoside

The title compound was prepared according to procedures D, F, G and L above using cyclohex-2-en-1-one as the electrophile. Mass spectra data was as follows: M (calcd.): 441.50, M (found): n.a. Selected nmr data was as follows: $^1$H-nmr (CD$_3$OD): δ4.37 (H-1), 4.34, and 4.32.

Example E1

Synthesis of Nα-[2-(1-Thio-β-D-galactopyranosyl) cyclopent-1-yl]glycine

The title compound was prepared according to procedures D, H and M above using 2-chlorocyclopentan-1-one as the electrophile and glycine tert-butyl ester as the amino acid ester. Mass spectra data was as follows: M (calcd.): 337.39; M (found): 359.8 (M+Na$^+$). Selected nmr data was as follows: $^1$H-nmr (CD$_3$OD): δ4.44 (H-1), 4.41, 4.40, and 4.34.

Example E2

Synthesis of Nα-[2-(1-Thio-β-D-galactopyranosyl) cyclohex-1-yl]glycine

The title compound was prepared according to procedures D, H and M above using 2-chlorocyclohexan-1-one as the electrophile and glycine tert-butyl ester as the amino acid ester. Mass spectra data was as follows: M (calcd.): 351.42; M (found): 353.5 (M+H$^+$), 376.5 (M+Na$^+$). Selected nmr data was as follows: $^1$H-nmr (CD$_3$OD): δ4.48 (H-1), 4.47, 4.36, and 4.29.

Example E3

Synthesis of Nα-[4-Phenyl-4-(1-thio-β--galactopyranosyl)but-2-yl]glycine

The title compound was prepared according to procedures D, H and M above using 4-phenylbut-3-en-2-one as the electrophile and glycine tert-butyl ester as the amino acid ester. Mass spectra data was as follows: M (calcd.): 401.48; M (found): 403.1 (M+H$^+$). Selected nmr data was as follows: $^1$H-nmr (CD$_3$OD): δ4.29 (H-1), 4.18, 3.92, and 3.91.

Example E4

Synthesis of Nα-[3-((1-Thio-β-D-galactopyranosyl) methyl) norborn-2-yl]glycine

The title compound was prepared according to procedures D, H and M above using 3-methylene-2-norbornanone as the electrophile and glycine tert-butyl ester as the amino acid ester. Mass spectra data was as follows: M (calcd.): 377.46; M (found): 401.4 (M+Na$^+$). Selected nmr data was as follows: $^1$H-nmr (CD$_3$OD): δ4.42 (H-1), 4.40, 4.383, 4.377, and 4.35.

Example E5

Synthesis of Nα-[3-(1-Thio-β-D-galactopyranosyl) cyclohept-1-yl]glycine

The title compound was prepared according to procedures D, H and M above using cyclohept-2-en-1-one as the electrophile and glycine tert-butyl ester as the amino acid ester. Mass spectra data was as follows: M (calcd.): 365.45; M (found): 367.4 (M+H$^+$), 389.9 (M+Na$^+$). Selected nmr data was as follows: $^1$H-nmr (CD$_3$OD): δ4.46 (H-1), 4.45, 4.42, and 4.38.

Example E5'

Synthesis of Nα-[3-(1-Thio-β-D-galactopyranosyl) cyclohept-1-yl]glycine

The title compound was prepared according to procedures D, H and M above using 1-S-acetyl-2,3,4,6-tetra-O-lauroyl-1-thio-β-D-galactopyranose (from Example C'above), cyclohept-2-en-1-one as the electrophile and glycine tert-butyl ester as the amino acid ester. Mass spectra data was as follows: M (calcd.): 365.45; M (found): 366.6 (M+H$^+$). Selected nmr data was as follows: $^1$H-nmr (CD$_3$OD): δ5.51 (d, J 5.5 Hz, H-1 (major), 5.46 (d, J 5.5 Hz, H-1), 5.47 (d, J 5.5 Hz, H-1 (minor)), 5.48 (d, J 5.5 Hz, H-1).

Example E6

Synthesis of Na-[4,4-Dimethyl-3-(1-thio-β-D-galactopyranosyl)-cyclopent-1-yl]glycine The title compound was prepared according to procedures D, H and M above using 4,4-dimethylcyclopent-2-en-1-one as the electrophile and glycine tert-butyl ester as the amino acid ester. Mass spectra data was as follows: M (calcd.): 365.44; M (found): 368.0 (M+H$^+$). Selected nmr data was as follows: $^1$H-nmr (CD$_3$OD): β4.330 (H-1), 4.325, 4.320, and 4.30.

Example E7

Synthesis of Nα-[3-(1-Thio-β-D-galactopyranosyl) cyclopent-1-yl]glycine

The title compound was prepared according to procedures D, H and M above using cyclopent-2-en-1-one as the electrophile and glycine tert-butyl ester as the amino acid ester. Mass spectra data was as follows: M (calcd.): 337.39; M (found): 360.9 (M+Na$^+$). Selected nmr data was as follows: $^1$H-nmr (CD$_3$OD): δ 4.38 (H-1), 4.375, 4.36, and 4.35.

Example E8

Synthesis of Nα-[4-(1-Thio-β-D-galactopyranosyl) pent-2-yl]glycine

The title compound was prepared according to procedures D, H and M above using pent-3-en-2-one as the electrophile and glycine tert-butyl ester as the amino acid ester. Mass spectra data was as follows: M (calcd.): 338.39; M (found): 363.9 (M+Na+). Selected nmr data was as follows: $^1$H-nmr (CD$_3$OD): δ4.43, 4.42, 4.37 (H-1), and 4.36.

Example E9

Synthesis of Nα-[4,4-Dimethyl-3-(1-thio-β-D-galactopyranosyl)-cyclohex-1-yl]glycine The title compound was prepared according to procedures D, H and M above using 4,4-dimethylcyclohex-2-en-1-one as the electrophile and glycine tert-butyl ester as the amino acid ester. Mass spectra data was as follows: M (calcd.): 379.47; M (found): 380.6 (M+H+), 403.5 (M+Na+). Selected nmr data was as follows: $^1$H-nmr (CD$_3$OD): δ4.38 (H-1), 4.36, 4.34, and 4.31.

Example E10

Synthesis of Nα-[3-(1-Thio-β-D-galactopyranosyl) cyclohex-1-yl]glycine

The title compound was prepared according to procedures D, H and M above using cyclohex-2-en-1-one as the electrophile and glycine tert-butyl ester as the amino acid ester. Mass spectra data was as follows: M (calcd.): 351.42; M (found): 377.1 (M+Na+). Selected nmr data was as follows: $^1$H-nmr (CD$_3$OD): δ4.46 (H-1), 4.44, 4.40, and 4.36.

Example E1

Synthesis of Nα-[5-(1-Thio-β-D-galactopyranosyl)-2,2-dimethylcyclohex-1-yl]glycine The title compound was prepared according to procedures D, H and M above using 6,6-dimethylcyclohex-2-en-1-one as the electrophile and glycine tert-butyl ester as the amino acid ester.

Example F1

Synthesis of Nβ-[2-(1-Thio-β-D-galactopyranosyl) cyclopent-1-yl]-β-alanine

The title compound was prepared according to procedures D, H and M above using 2-chlorocyclopentan-1-one as the electrophile and β-alanine tert-butyl ester as the amino acid ester. Mass spectra data was as follows: M (calcd.): 351.42; M (found): 372.9 (M+Na+). Selected nmr data was as follows: $^1$H-nmr (CD$_3$OD): δ4.54 (H-1), 4.52, 4.36, and 4.35.

Example F2

Synthesis of Nβ-[2-(1-Thio-β-D-galactopyranosyl) cyclohex-1-yl]-β-alanine

The title compound was prepared according to procedures D, H and M above using 2-chlorocyclohexan-1-one as the electrophile and β-alanine tert-butyl ester as the amino acid ester. Mass spectra data was as follows: M (calcd.): 365.45; M (found): 367.4 (M+H+), 389.9 (M+Na+), 412.0 (M+K+). Selected nmr data was as follows: $^1$H-nmr (CD$_3$OD): δ4.47 (H-1), 4.42, 4.41, and 4.33.

Example F3

Synthesis of Nβ-[4-Phenyl-4-(1-thio-β-galactopyranosyl)but-2-yl]β-alanine

The title compound was prepared according to procedures D, H and M above using 4-phenylbut-3-en-2-one as the electrophile and β-alanine tert-butyl ester as the amino acid ester. Mass spectra data was as follows: M (calcd.): 415.50; M (found): 417.0 (M+H+). Selected nmr data was as follows: $^1$H-nmr (CD$_3$OD): δ4.28 (H-1), 4.17, 3.97, and 3.96.

Example F4

Synthesis of Nβ-[3-((1-Thio-β-D-galactopyranosyl) methyl)norborn-2-yl]-β-alanine The title compound was prepared according to procedures D, H and M above using 3-methylene-2-norbornanone as the electrophile and β-alanine tert-butyl ester as the amino acid ester. Mass spectra data was as follows: M (calcd.): 391.48; M (found): 393.6 (M+H+). Selected nmr data was as follows: $^1$H-nmr (CD$_3$OD): δ 4.40 (H-1), 4.37, 4.34, and 4.33.

Example F5

Synthesis of Nβ-[3-(1-Thio-β-D-galactopyranosyl) cyclohept-1-yl]-β-alanine

The title compound was prepared according to procedures D, H and M above using cyclohept-2-en-1-one as the electrophile and β-alanine tert-butyl ester as the amino acid ester. Mass spectra data was as follows: M (calcd.): 379.45; M (found): 381.7 (M+H+), 403.5 (M+Na+), 426.0 (M+K+). Selected nmr data was as follows: $^1$H-nmr (CD$_3$OD): δ4.46 (H-1), and 4.38.

Example F6

Synthesis of Nβ-[4,4-Dimethyl-3-(1-thio-β-D-galactopyranosyl)-cyclopent-1-yl]-βalanine The title compound was prepared according to procedures D, H and M above using 4,4-dimethylcyclopent-2-en-1-one as the electrophile and β-alanine tert-butyl ester as the amino acid ester. Mass spectra data was as follows: M (calcd.): 379.44; M (found): 383.2 (M+H+). Selected nmr data was as follows: $^1$H-nmr (CD$_3$OD): δ4.34 (H-1), 4.33, 4.315, and 4.310.

Example F7

Synthesis of N-β-[3-(1-Thio-β-D-galactopyranosyl) cyclopent-1-yI]-β-alanine

The title compound was prepared according to procedures D, H and M above using cyclopent-2-en-1-one as the electrophile and β-alanine tert-butyl ester as the amino acid ester. Mass spectra data was as follows: M (calcd.): 351.42; M (found): 375.1 (M+Na+). Selected nmr data was as follows: $^1$H-nmr (CD$_3$OD): δ4.41 (H-1), and 4.40.

Example F8

Synthesis of Nβ-[4-(1-Thio-β-D-galactopyranosyl) pent-2-yl]-β-alanine

The title compound was prepared according to procedures D, H and M above using pent-3-en-2-one as the electrophile and β-alanine tert-butyl ester as the amino acid ester. Mass spectra data was as follows: M (calcd.): 352.42; M (found): 356.0 (M+H+). Selected nmr data was as follows: $^1$H-nmr (CD$_3$OD): δ4.49 (H-1), 4.440, and 4.435.

Example F9

Synthesis of Nβ-[4,4Dimethyl-3-(1-thio-β-D-galactopyranosyl)-cyclohex-1-yl]-β-alanime The title compound was prepared according to procedures D, H and M above using 4,4-dimethylcyclohex-2-en-1-one as the electrophile and β-alanine tert-butyl ester as the amino acid ester. Mass spectra data was as follows: M (calcd.): 393.50; M (found): 399.3 (M+H⁺), 419.5 (M+Na⁺), 442.4 (M+K⁺). Selected nmr data was as follows: ¹H-nmr (CD₃OD): δ4.35 (H-1), 4.34, and 4.32.

Example F10

Synthesis of Nβ-[3-(1-Thio-β-D-galactopyranosyl) cyclohex-1-yl]-β-alanine

The title compound was prepared according to procedures D, H and M above using cyclohex-2-en-1-one as the electrophile and β-alanine tert-butyl ester as the amino acid ester. Mass spectra data was as follows: M (calcd.): 365.45; M (found): 367.0 (M+H⁺), 389.9 (M+Na⁺). Selected nmr data was as follows: ¹H-nmr (CD₃OD): δ4.46 (H-1), 4.44, 4.43, and 4.36.

Example F11

Synthesis of N-β-[5-(1-Thio-α-D-galactopyranosyl)-2,2-dimethylcyclohex-1-yl]-β-alanine The title compound was prepared according to procedures D, H and M above using 6,6-dimethylcyclohex-2-en-1-one as the electrophile and β-alanine tert-butyl ester as the amino acid ester.

Example G1

Synthesis of Nα-[2-(1-Thio-β-D-galactopyranosyl) cyclopent-1-yl]-L-leucine

The title compound was prepared according to procedures D, H and M above using 2-chlorocyclopentan-1-one as the electrophile and L-leucine tert-butyl ester as the amino acid ester. Mass spectra data was as follows: M (calcd.): 393.50; M (found): 396.4 (M+H⁺). Selected nmr data was as follows: ¹H-nmr (CD₃OD): δ 4.47 (H-1), 4.43, 4.36, and 4.34.

Example G2

Synthesis of Nα-[2-(1-Thio-β-D-galactopyranosyl) cyclohex-1-yl]-L-leucine

The title compound was prepared according to procedures D, H and M above using 2-chlorocyclohexan-1-one as the electrophile and L-leucine tert-butyl ester as the amino acid ester. Mass spectra data was as follows: M (calcd.): 407.53; M (found): 410.9, (M+H⁺), 435.5 (M+Na⁺). Selected nmr data was as follows: ¹H-nmr (CD₃OD): δ4.49 (H-1), 4.44, 4.41, and 4.37.

Example G3

Synthesis of Nα-[4-Phenyl-4-(1-thio-β-galactopyranosyl)but-2-yl]-L-leucine

The title compound was prepared according to procedures D, H and M above using 4-phenylbut-3-en-2-one as the electrophile and L-leucine tert-butyl ester as the amino acid ester. Mass spectra data was as follows: M (calcd.): 458.59; M (found): 480.5 (M+Na⁺). Selected nmr data was as follows: ¹H-nmr (CD₃OD): δ4.39 (H-1), 4.36, 4.29, and 4.21.

Example G5

Synthesis of Nα-[1-(1-Thio-β-D-galactopyranosyl) cyclohept-3-yl]-L,leucine

The title compound was prepared according to procedures D, H and M above using cyclohept-2-en-1-one as the electrophile and L-leucine tert-butyl ester as the amino acid ester. Mass spectra data was as follows: M (calcd.): 421.55; M (found): 421.7 (M+H⁺), 448.0 (M+Na⁺). Selected nmr data was as follows: ¹H-nmr (CD₃OD): δ4.44 (H-1), 4.43, and 4.36.

Example G6

Synthesis of Nα-[4,4Dimethyl-3-(1-thio-β-D-galactopyranosyl)-cyclopent-1-yl]-L-leucine The title compound was prepared according to procedures D, H and M above using 4,4-dimethylcyclopent-2-en-1-one as the electrophile and L-leucine tert-butyl ester as the amino acid ester. Mass spectra data was as follows: M (calcd.): 421.55; M (found): 422.3 (M+H⁺). Selected nmr data was as follows: ¹H-nmr (CD₃OD): δ4.320 (H-1) and 4.315.

Example G7

Synthesis of Nα-[3-(1-Thio-β-D-galactopyranosyl) cyclopent-1-yl]-L-leucine

The title compound was prepared according to procedures D, H and M above using cyclopent-2-en-1-one as the electrophile and L-leucine tert-butyl ester as the amino acid ester. Mass spectra data was as follows: M (calcd.): 393.50; M (found): 393.6 (M+H⁺), 417.0 (M+Na⁺). Selected nmr data was as follows: ¹H-nmr (CD₃OD): δ4.380 (H-1), 4.375, 4.370 and 4.367.

Example G8

Synthesis of Nα-[4-(1-Thio-β-D-galactopyranosyl) pent-2-yl]-L-leucine

The title compound was prepared according to procedures D, H and M above using pent-3-en-2-one as the electrophile and L-leucine tert-butyl ester as the amino acid ester. Mass spectra data was as follows: M (calcd.): 395.51; M (found): 396.8 (M+H⁺), 419.1 (M+Na⁺), and 440.9 (M+K⁺). Selected nmr data was as follows: ¹H-nmr (CD₃OD): δ4.42 (H-1), 4.41, 4.405 and 4.40.

Example G9

Synthesis of Nα-[4,4-Dimethyl-3-(1-thio-β-D-galactopyranosyl)-cyclohex-1-yl]-L-leucine The title compound was prepared according to procedures D, H and M above using 4,4-dimethylcyclohex-2-en-1-one as the electrophile and L-leucine tert-butyl ester as the amino acid ester. Mass spectra data was as follows: M (calcd.): 436.58; M (found): 438.0 (M+H⁺), 461.4 (M+Na⁺). Selected nmr data was as follows: ¹H-nmr (CD₃OD): δ4.38 (H-1) and 4.34.

Example G10

Synthesis of Nα-[3-(1-Thio-β-D-galactopyranosyl) cyclohex-1-yl]-L-leucine

The title compound was prepared according to procedures D, H and M above using cyclohex-2-en-1-one as the electrophile and L-leucine tert-butyl ester as the amino acid ester. Mass spectra data was as follows: M (calcd.): 407.53; M (found): 408.4 (M+H⁺). Selected nmr data was as follows: ¹H-nmr (CD₃OD): δ4.46 (H-1), 4.42, 4.40, and 4.33.

Example H1

Synthesis of Nα-[2-(1-Thio-β-D-galactopyranosyl) cyclopent-1-yl]-L-histidine

The title compound was prepared according to procedures D, H and N above using 2-chlorocyclopentan-1-one as the electrophile and L-histidine methyl ester as the amino acid ester. Mass spectra data was as follows: M (calcd.): 417.48; M (found): 418.7 (M+H$^+$). Selected nmr data was as follows: $^1$H-nmr (CD$_3$OD): δ4.45 (H-1), 4.41, 4.40, and 4.29.

Example H2

Synthesis of Nα-[2-(1-Thio-β-D-galactopyranosyl)cyclohex-1-yl]-L-histidine

The title compound was prepared according to procedures D, H and N above using 2-chlorocyclohexan-1-one as the electrophile and L-histidine methyl ester as the amino acid ester. Mass spectra data was as follows: M (calcd.): 431.50; M (found): 433.6 (M+H$^+$). Selected nmr data was as follows: $^1$H-nmr (CD$_3$OD): δ4.52 (H-1), 4.45, 4.40, and 4.28.

Example H3

Synthesis of Nα-[4-Phenyl-4-(1-thio-β-D-galactopyranosyl)but-2-yl]-L-histidine

The title compound was prepared according to procedures D, H and N above using 4-phenylbut-3-en-2-one as the electrophile and L-histidine methyl ester as the amino acid ester. Mass spectra data was as follows: M (calcd.): 481.56; M (found): 482.8 (M+H$^+$). Selected nmr data was as follows: $^1$H-nmr (CD$_3$OD): δ4.38 (H-1), 4.36, 4.23, and 4.16.

Example H5

Synthesis of Nα-[3-(1-Thio-β-D-galactopyranosyl)cyclohept-1-yl]-L-histidine

The title compound was prepared according to procedures D, H and N above using cyclohept-2-en-1-one as the electrophile and L-histidine methyl ester as the amino acid ester. Mass spectra data was as follows: M (calcd.): 445.54; M (found): 448.0 (M+H$^+$). Selected nmr data was as follows: $^1$H-nmr (CD$_3$OD): δ4.50 (H-1), 4.44, 4.41, and 4.32.

Example H6

Synthesis of Nα-[4,4-Dimethyl-3-(1-thio-β-D-galactopyranosyl)-cyclopent-1-yl]-L-histidine The title compound was prepared according to procedures D, H and N above using 4,4-dimethylcyclopent-2-en-1-one as the electrophile and L-histidine methyl ester as the amino acid ester. Mass spectra data was as follows: M (calcd.): 445.54; M (found): 447.6 (M+H$^+$). Selected nmr data was as follows: $^1$H-nmr (CD$_3$OD): δ4.33 (H-1), 4.32, 4.305, and 4.30.

Example H7

Synthesis of Nα-[3-(1-Thio-β-D-galactopyranosyl)cyclopent-1-yl]-L-histidine

The title compound was prepared according to procedures D, H and N above using cyclopent-2-en-1-one as the electrophile and L-histidine methyl ester as the amino acid ester. Mass spectra data was as follows: M (calcd.): 418.48; M (found): 418.0 (M+H$^+$). Selected nmr data was as follows: $^1$H-nmr (CD$_3$OD): δ4.39 (H-1), 4.38, 4.36, and 4.32.

Example H8

Synthesis of Nα-[4-(1-Thio-β-D-galactopyranosyl)pent-2-yl]-L-histidine

The title compound was prepared according to procedures D, H and N above using pent-3-en-2-one as the electrophile and L-histidine methyl ester as the amino acid ester. Mass spectra data was as follows: M (calcd.): 419.49; M (found): 420.2 (M+H$^+$). Selected nmr data was as follows: $^1$H-nmr (CD$_3$OD): δ4.44 (H-1), 4.41, 4.40, and 4.36.

Example H9

Synthesis of Nα-[4,4-Dimethyl-3-(1-thio-β-D-galactopyranosyl)-cyclohex-1-yl]-L-histidine The title compound was prepared according to procedures D, H and N above using 4,4-dimethylcyclohex-2-en-1-one as the electrophile and L-histidine ethyl ester as the amino acid ester. Mass spectra data was as follows: M (calcd.): 459.56; M (found): 462.2 (M+H$^+$). Selected nmr data was as follows: $^1$H-nmr (CD$_3$OD): δ4.364 (H-1), 4.357, and 4.34.

Example H10

Synthesis of Nα-[3-(1-Thio-β-D-galactopyranosyl)cyclohex-1-yl]-L-histidine

The title compound was prepared according to procedures D, H and N above using cyclohex-2-en-1-one as the electrophile and L-histidine methyl ester as the amino acid ester. Mass spectra data was as follows: M (calcd.): 431.51; M (found): 433.2 (M+H$^+$). Selected nmr data was as follows: $^1$H-nmr (CD$_3$OD): δ4.43 (H-1), 4.425, 4.39 and 4.35.

Example I1

Synthesis of Nα-[2-(1-Thio-β-D-galactopyranosyl)cyclopent-1-yl]-L-tryptophan

The title compound was prepared according to procedures D, H and N above using 2-chlorocyclopentan-1-one as the electrophile and L-tryptophan methyl ester as the amino acid ester. Mass spectra data was as follows: M (calcd.): 466.55; M (found): 467.5 (M+H$^+$). Selected nmr data was as follows: $^1$H-nmr (CD$_3$OD): δ4.51 (H-1), 4.39, 4.28 and 4.27.

Example I2

Synthesis of Nα-[2-(1-Thio-β-D-galactopyranosyl)cyclohex-1-yl]-L-tryptophan

The title compound was prepared according to procedures D, H and N above using 2-chlorocyclohexan-1-one as the electrophile and L-tryptophan methyl ester as the amino acid ester. Mass spectra data was as follows: M (calcd.): 480.59; M (found): 481.9 (M+H$^+$), 505.3 (M+Na$^+$). Selected nmr data was as follows: $^1$H-nmr (CD$_3$OD): δ4.46 (H-1), 4.40, 4.24 and 4.09.

Example I3

Synthesis of Nα-[4-Phenyl-4-(1-thio-β-D-galactopyranosyl)but-2-yl]-L-tryptophan

The title compound was prepared according to procedures D, H and N above using 4-phenylbut-3-en-2-one as the electrophile and L-tryptophan methyl ester as the amino acid ester. Mass spectra data was as follows: M (calcd.): 531.64; M (found): 531.3 (M+H$^+$). Selected nmr data was as follows: $^1$H-nmr (CD$_3$OD): δ4.24 (H-1), 4.23, 4.14 and 4.09.

Example I5

Synthesis of Nα-[3-(1-Thio-β-D-galactopyranosyl)cyclohept-1-yl]-L-tryptophan

The title compound was prepared according to procedures D, H and N above using cyclohept-2-en-1-one as the electrophile and L-tryptophan methyl ester as the amino acid ester. Mass spectra data was as follows: M (calcd.): 494.60; M (found): 495.9 (M+H$^+$). Selected nmr data was as follows: $^1$H-nmr (CD$_3$OD): δ4.50 (H-1), 4.44, 4.41 and 4.32.

Example I6

Synthesis of Nα-[4,4-Dimethyl-3-(1-thio-β-D-galactopyranosyl)-cyclopent-1-yl]-L-tryptophan The title compound was prepared according to procedures D, H and N above using 4,4-dimethylcyclopent-2-en-1-one as the electrophile and L-tryptophan methyl ester as the amino acid ester. Mass spectra data was as follows: M (calcd.): 494.60; M (found): 495.6 (M+H$^+$). Selected nmr data was as follows: $^1$H-nmr (CD$_3$OD): δ4.26 (H-1), 4.22, 4.20 and 4.13.

Example I7

Synthesis of Nα-[3-(1-Thio-β-D-galactopyranosyl) cyclopent-1-yl]-L-tryptophan

The title compound was prepared according to procedures D, H and N above using cyclopent-2-en-1-one as the electrophile and L-tryptophan methyl ester as the amino acid ester. Mass spectra data was as follows: M (calcd.): 466.55; M (found): 467.9 (M+H$^+$). Selected nmr data was as follows: $^1$H-nmr (CD$_3$OD): δ4.33 (H-1), 4.32, 4.30 and 4.23.

Example I8

Synthesis of Nα-[4-(1-Thio-β-D-galactopyranosyl) pent-2-yl]-L-tryptophan

The title compound was prepared according to procedures D, H and N above using pent-3-en-2-one as the electrophile and L-tryptophan methyl ester as the amino acid ester. Mass spectra data was as follows: M (calcd.): 468.57; M (found): 490.9 (M+Na$^+$). Selected nmr data was as follows: $^1$H-nmr (CD$_3$OD): δ4.30 (H-1), 4.27, 4.22 and 4.09.

Example I9

Synthesis of Nα-[4,4-Dimethyl-3-(1-thio-β-D-galactopyranosyl)-cyclohex-1-yl]-L-tryptophan The title compound was prepared according to procedures D, H and N above using 4,4-dimethylcyclohex-2-en-1-one as the electrophile and L-tryptophan methyl ester as the amino acid ester. Mass spectra data was as follows: M (calcd.): 508.63; M (found): 512.1 (M+H$^+$). Selected nmr data was as follows: $^1$H-nmr (CD$_3$OD): δ4.30 (H-1), 4.26, and 4.21.

Example I10

Synthesis of Nα-[3-(1-Thio-β-D-galactopyranosyl) cyclohex-1-yl]-L-tryptophan

The title compound was prepared according to procedures D, H and N above using cyclohex-2-en-1-one as the electrophile and L-tryptophan methyl ester as the amino acid ester. Mass spectra data was as follows: M (calcd.): 480.59; M (found): 483.9 (M+H$^+$). Selected nmr data was as follows: $^1$H-nmr (CD$_3$OD): δ4.36 (H-1), 4.35, 4.33, and 4.24.

Example J1

Synthesis of Nα-[2-(1-Thio-β-D-galactopyranosyl) cyclopent-1-yl]-L-arginine

The title compound was prepared according to procedures D, H and O above using 2-chlorocyclopentan-1-one as the electrophile and L-arginine methyl ester as the amino acid ester. Mass spectra data was as follows: M (calcd.): 436.52; M (found): 436.2 (M+H$^+$). Selected nmr data was as follows: $^1$H-nmr (CD$_3$OD): δ4.54 (H-1), 4.43, 4.41, and 4.28.

Example J2

Synthesis of Nα-[2-(1-Thio-β-D-galactopyranosyl) cyclohex-1-yl]-L-arganine

The title compound was prepared according to procedures D, H and O above using 2-chlorocyclohexan-1-one as the electrophile and L-arginine methyl ester as the amino acid ester. Mass spectra data was as follows: M (calcd.): 450.56; M (found): 453.5 (M+H$^+$). Selected nmr data was as follows: $^1$H-nmr (CD$_3$OD): δ4.47 (H-1), 4.45, 4.44, and 4.38.

Example J3

Synthesis of Nα-[4-Phenyl-4-(1-Thio-β-D-galactopyranosyl)but-2-yl]-L-arginine

The title compound was prepared according to procedures D, H and O above using 2-chlorocyclohexan-1-one as the electrophile and L-arginine methyl ester as the amino acid ester. Mass spectra data was as follows: M (calcd.): 501.62; M (found): 503.8 (M+H$^+$). Selected nmr data was as follows: $^1$H-nmr (CD$_3$OD): δ4.32 (H-1), 4.31, and 4.30.

Example J5

Synthesis of Nα-[3-(1-Thio-β-D-galactopyranosyl) cyclohept-1-yl]-L-arginine

The title compound was prepared according to procedures D, H and O above using cyclohept-2-en-1-one as the electrophile and L-arginine methyl ester as the amino acid ester. Mass spectra data was as follows: M (calcd.): 464.58; M (found): 467.1 (M+H$^+$). Selected nmr data was as follows: $^1$H-nmr (CD$_3$OD): δ4.48 (H-1), 4.46, and 4.43.

Example J6

Synthesis of Nα-[4,4-Dimethyl-3-(1-thio-β-D-galactopyranosyl)-cyclopent-1-yl]-L-arginine The title compound was prepared according to procedures D, H and O above using 4,4-dimethylcyclopent-2-en-1-one as the electrophile and L-arginine methyl ester as the amino acid ester. Mass spectra data was as follows: M (calcd.): 464.58; M (found): 465.6 (M+H$^+$). Selected nmr data was as follows: $^1$H-nmr (CD$_3$OD): δ4.37 (H-1), 4.35, 4.34, and 4.30.

Example J7

Synthesis of Nα-[3-(1-Thio-β-D-galactopyranosyl) cyclopent-1-yl]-L-arginine

The title compound was prepared according to procedures D, H and O above using cyclopent-2-en-1-one as the electrophile and L-arginine methyl ester as the amino acid ester. Mass spectra data was as follows: M (calcd.): 436.53; M (found): 437.6 (M+H$^+$). Selected nmr data was as follows: $^1$H-nmr (CD$_3$OD): δ4.37 (H-1), 4.35, and 4.34.

Example J8

Synthesis of Nα-[4-(1-Thio-β-D-galactopyranosyl) pent-2-yl]-L-arginine

The title compound was prepared according to procedures D, H and O above using pent-3-en-2-one as the electrophile and L-arginine methyl ester as the amino acid ester. Mass spectra data was as follows: M (calcd.): 438.54; M (found): 437.3 (M+H⁺). Selected nmr data was as follows: ¹H-nmr (CD₃OD): δ4.46 (H-1), 4.41, 4.39, and 4.38.

Example J9

Synthesis of Nα-[4,4-Dimethyl-3-(1-thio-β-D-galactopyranosyl)-cyclohex-1-yl]-L-arginine The title compound was prepared according to procedures D, H and O above using 4,4-dimethylcyclohex-2-en-1-one as the electrophile and L-arginine methyl ester as the amino acid ester. Mass spectra data was as follows: M (calcd.): 478.60; M (found): 479.0 (M+H⁺). Selected nmr data was as follows: ¹H-nmr (CD₃OD): δ4.43 (H-1), 4.41, 4.38, and 4.32.

Example J10

Synthesis of Nα-[3-(1-Thio-β-D-galactopyranosyl)cyclohex-1-yl]-L-arginine

The title compound was prepared according to procedures D, H and O above using cyclohex-2-en-1-one as the electrophile and L-arginine methyl ester as the amino acid ester. Mass spectra data was as follows: M (calcd.): 450.55; M (found): 451.8 (M+H⁺). Selected nmr data was as follows: ¹H-nmr (CD₃OD): δ4.34 (H-1), 4.33, 4.32, and 4.29.

EXAMPLE 1

Synthesis of the Individual Diastereomers of 2,2-Dimethyl-4-(cyclobut-1-ylamino)-cyclopent-1-yl 1-Thio-β-D-galactopyranoside This example illustrates the preparation of individual diastereomers of a compound of formula I.

Step A

Synthesis of (1R,S)-2,2-Dimethylcyclopentan-4on-1-yl 2,3,4,6 -Tetra-O-lauroyl-1-thio-β-D-galactopyranoside To 1-S-acetyl-2,3,4,6-tetra-O-lauryl-1-thio-β-D-galactopyranose (5 g, 5 mmol) (from Example C above) and 4,4-dimethyl-2-cyclopenten-1-one (500 mg, 4.45 mmol) in dry CH₂Cl₂ (10 mL) under argon, was added Et₂NH (6 mL). After 3 h, the mixture was concentrated and purified by column chromatography (SiO₂, pentane/EtOAc, 9:1) to give the title compound as a mixture of diastereomers (3.54 g, 66%).

Step B

Separation of the Diastereomers of (1R,S)-2,2 -Dimethylcyclopentan-4-on-1-yl 2,3,4,6-Tetra-O-lauroyl-1-thio-β-D-galactopyranoside The two diastereomers from Step A (5 g, 4.8 mmol) were separated by column chromatography (SiO₂, pentane/EtOAc, 9:1) to give (1S)-2,2 -dimethylcyclopentan-4-on-1-yl 2,3,4,6-tetra-O-lauroyl-1-thio-β-D-galactopyranoside (428.8 mg, 8%) and (1R)-2,2-dimethylcyclopentan-4-on-1-yl 2,3,4,6-tetra-O-lauroyl-1-thio-β-D-galactopyranoside (373.8 mg, 6%) along with a mixture of unresolved compounds (2.74 g, 52%).

Step C

Synthesis of (1S, 4RS)- and (1R, 4RS)-2,2-Dimethyl-4 -hydroxycyclopent-1-yl 2,3 ,4,6-Tetra-O-lauroyl-1-thio-β-D-galactopyranoside To each of the purified diastereomers from Step B (in separate reaction flasks) (320 mg, 0.3 mmol) in dry tetrahydrofuran (3 mL), methanol (0.5 mL) and isopropanol (2 mL) under argon atmosphere, was added NaBH₄ (0.12 mmol). After 30 min, AcOH (1 drop) is added and the mixtures were concentrated and the residues dissolved MeOH (2 mL) and added to a column of C-18 silica (5 g). The columns were washed with MeOH (50 mL) and products eluted pentane (50 mL) to give (1S, 4RS)-2,2-dimethyl-4-hydroxy-cyclopent-1-yl 2,3,4, 6-tetra-O-lauroyl-1-thio-β-D-galactopyranoside (281 mg, 88%) and (1R, 4RS)-2,2-dimethyl-4-hydroxy-cyclopent-1-y 2,3,4,6-tetra-O-lauroyl-1-thio-β-D-galactopyranoside (297 mg, 93%).

Step D

Synthesis of (1S, 4RS)- and (1R, 4RS)-2,2-Dimethyl-4 -O-methanesulfonyloxycyclopent-1-yl 2,3,4,6-Tetra-O-lauroyl-1-thio-β-D-galactopyranoside To each of the (1S, 4RS) and (1R, 4RS) mixtures from Step C (in separate reaction flasks) (280 mg, 0.3 mmol) in dry tetrahydrofuran (2 mL) and dry pyridine (4 mL) under argon atmosphere, was added methanesulfonyl chloride (0.5 mL). After 12 h, the mixtures were washed with 0.5 M HCl and extracted with pentane. After concentration, the residues were purified on C18-silica (5 g) as described in Step C to afford (1S, 4RS)-2,2-dimethyl-4 -O-methanesulfonyloxycyclopent-1-yl 2,3,4,6-tetra-O-lauroyl-1-thio-β-D-galactopyranoside (281 mg, 88%) and (5) (1R, 4RS)-2,2-dimethyl-4 -O-methanesulfonyloxycyclopent-1-yl 2,3,4,6-tetra-O-lauroyl-1-thio-β-D-galactopyranoside (297 mg, 93%) as white solids after pentane evaporation.

Step E

Synthesis of (1S, 4R)-, (1S, 4S)-, (1R, 4S)- and (1R, 4R)-2,2 -Dimethyl-4-azidocyclopent-1-yl 2,3, 4,6-Tetra-O-lauroyl-1-thio-β-D-galactopyranoside To the (1S, 4RS) and (1R, 4RS) mixtures from Step D (in separate reaction flasks) (250 mg, 0.2 mmol) in dry DMF (8 mL) and dry THF (3 mL) under argon atmosphere at 60° C. was added NaN₃ (340 mg, 5 mmol) and 18 crown-6 (180 mg). After 2 h, the mixtures were concentrated and purified on C18 -silica (5 g) as described in Step C. Re-chromatography (SiO₂, pentane/EtOAc, 9:1) permitted the separation of diastereomers to give pure (1S, 4R)-2,2-dimethyl-4 -azidocyclopent-1-yl 2,3,4,6-tetra-O-lauroyl-1-thio-β-D-galactopyranoside (163 mg, 65%); (1S, 4S)-2,2-dimethyl-4-azidocyclopent-1-yl2,3,4,6-tetra-O-lauroyl-1-thio-β-D-galactopyranoside (29 mg, 9%); (1R, 4S)-2,2-dimethyl-4-azidocyclopent-1-yl2,3,4,6 -tetra-O-lauroyl-1-thio-β-D-galactopyranoside (68 mg, 28%); and (1R, 4R)-2,2 -dimethyl-4-azidocyclopent-1-yl 2,3,4, 6-tetra-O-lauroyl-1-thio-β-D-galactopyranoside (21 mg, 9%).

Step F

Synthesis of (1S, 4R)-, (1S, 4S)-, (1R, 4S)- and (1R, 4R)-2,2 -Dimethyl-4-aminocyclopent-1-yl 2,3, 4,6-Tetra-O-lauroyl-1-thio-β-D-galactopyranoside To each of the four diastereomers of 2,2-dimethyl-4 -azido-cyclopent-1-yl 1-thio-β-D-galactopyranoside from Step E (5 mg, 15 μmol) in dry isopropanol (1 mL) and dry ethanol (1 mL) under argon atmosphere, was added NaBH₄ (15 μmol) and NiCl₂ (30 μmol). After 1 h, the mixtures were neutralized with AcOH (1 drop), concentrated and purified on C18-silica (2 g) as described in Step C to give (1S, 4R)-, (1S, 4S)-, (1R, 4S)- and (1R, 4R)-2,2-dimethyl-4 -aminocyclopent-1-yl 1-thio-β-D-galactopyranoside (each 5 mg; quant.).

Step G

Synthesis of (1S, 4R)-, (1S, 4S)-, (1R, 4S)- and (1R, 4R)-2,2 -Dimethyl-4-(cyclobut-1-ylamino)cyclopent-1-yl 2,3,4,6-Tetra-O-lauroyI-1-thio-β-D-galactopyranoside To each of four diastereomers of 2,2-dimethyl-4-aminocyclopent-1-yl 1-thio-β-D-galactopyranoside from Step F (in separate reaction flasks) (2 mg, 6.8 μmol) in dry methanol (1 mL) and dry dichloromethane (1 mL) under argon atmosphere, was added cyclobutanone (250 μL, 3.4 mmol) and sodium triacetoxyborohydride (10 mg, 47 μmol). After 24–48 h, toluene (1 mL) was added and the mixture was concentrated and the residue purified on C18-silica as described in Step C to give 2.1–2.4 mg (quant.) each of:

(1S, 4R)-2,2-dimethyl-4-(cyclobut-1-ylamino)cyclopent-1-yl 1-thio-β-D-galactopyranoside (B6HA); M (calcd.): 361.50; M (found): 361.6 (M+H⁺); ¹H-nmr (CD₃OD): δ4.292 (H-1);

(1S, 4S)-2,2-dimethyl-4-(cyclobut-1-ylamino)cyclopent-1-yl 1-thio-β-D-galactopyranoside (B6HB); M (calcd.): 361.50; M (found): 361.6 (M+H⁺); ¹H-nmr (CD₃OD): 4.315 (H-1);

(1R, 4S)-2,2-dimethyl-4-(cyclobut-1-ylamino)cyclopent-1-yl 1-thio-β-D-galactopyranoside (B6HC); M (calcd.): 361.50; M (found): 361.6 (M+H⁺); ¹H-nmr (CD₃OD): δ4.300 (H-1);

(1R, 4R)-2,2-dimethyl-4-(cyclobut-1-ylamino)cyclopent-1-yl 1-thio-β-D-galactopyranoside (B6HD); M (calcd.): 361.50; M (found): 361.6 (M+H⁺); ¹H-nmr (CD₃OD): 8 4.290 (H-1).

EXAMPLE 2

Attachment of [3-(Carboxybenzamido)norborn-2-yl]methyl l-Thio-β-D-galactopyranoside to a Solid Support To [3-(carboxybenzamido)norborn-2-yl]methyl 1-thio-β-D-galactopyranoside (2.1 mg, 4.5 ,mol, from Example D4 above), silyl aminated Chromosorb P (449 mg, prepared as described in U.S. Pat. No. 4,137,401[10] and Westal et al.[11]), and hydroxybenzotriazole (1.3 mg, 9.4 μmol) in DMF (1 mL, dried over 4 Å molecular sieves), was added diisopropylcarbodiimide (1.4 μL, 9.0 μmol). The beads were filtered off after 75 hours, washed with water, DMF, MeOH, and CH₂Cl₂. To the resulting beads in MeOH (1.5 mL) was added acetic anhydride (0.5 mL) and after 16.5 hours, the beads were filtered and washed with water, DMF, MeOH, CH₂Cl₂, and pentane. Fine particles were removed by suspending the beads in MeOH and decanting the supernatant repeatedly. Drying under high-vacuum gave 433 mg of a product having [3-(carboxybenzamido)norborn-2-yl]methyl 1-thio-β-D-galactopyranoside covalently attached to the Chromasorb P by formation of an amide linkage between amine group of the chromasorb P and the carboxy group of the 1 -thiogalactose derivative as shown in formula III below. Phenol/H₂SO₄ assay using the procedure described in M. Dubois et al.[9] showed an incorporation yield of 4.0 μmol/g.

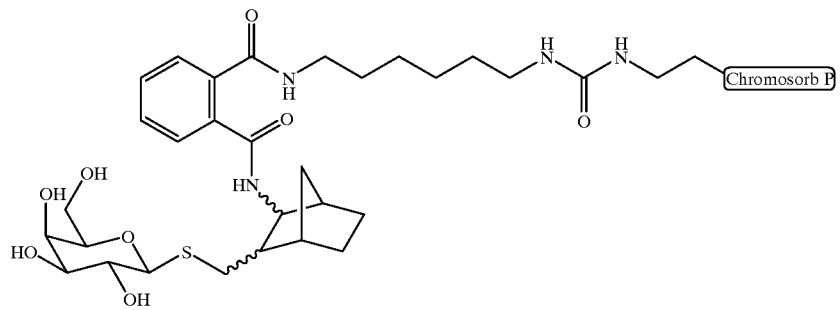

III

EXAMPLE 3

Solid-Phase Synthesis of 1-Thiogalactose Derivatives

The example illustrates the solid-phase synthesis of 1-thiogalactose derivatives of formula I.

Step A

Synthesis of 1-Dithioethyl-2,3,4,6-tetra-O-acetyl-galactopyranoside

1-Thio-2,3,4,6-tetra-O-acetyl-galactopyranoside (500 mg, 1.37 mmol) and diethyl-N-ethyl-sulfenylhydrazodicarboxylate (360 mg, 2.0 mmol) (prepared as described in T. Mukaiyama[12]) are dissolved in dichloromethane (14 mL) and stirred at room temperature. After 10 min, the solution is concentrated and column chromatography (SiO₂, hexane/ethylacetate 2:1) yields 1-dithioethyl-2,3,4,6 -tetra-O-acetyl-galactopyranoside (580 mg, quant) as a white solid ($R_f$ 0.27 in hexanes/ethyl acetate (2:1)).

¹H-NMR (360 MHz, CHCl₃): δ1.30 (dd, 3 H, J=7.4 Hz, CH₃), 1.96, 2.02, 2.03, 2.13 (4 s, 12 H, 4 CH₃CO), 2.79 (ddd, 2 H, J=7.4 Hz, J=7.4 Hz, J=1.3 CH2), 3.94 (ddd, 1 H, $J_{4,5}$=1.0 Hz, $J_{5,6}$=6.6 Hz, $J_{5,6b}$=7.6 Hz, 5-H), 4.10 (ddd, 2 H, 61-H, 6b-H), 4.51 (d, 1 H, $J_{1,2}$=10.0 Hz, 1-H), 5.05 (dd, 1 H, $J_{2,3}$ =10.0 Hz, $J_{3,4}$=3.3 Hz, 3-H)), 5.38 (dd, 1 H, $J_{1,2}$=10.0 Hz, $J_{3,3}$=10.0 Hz, 2-H), 5,40 (dd, 1 H, $J_{3,4}$=3.3 Hz, $J_{4,5}$=1.0 Hz, 4-H); m/z calcd. for C₁₆H₂₄O₉S₂ (M+Na) 447. 1, found 447.0.

Step B

Synthesis of 1-Dithioethyl-β-D-galactopyranoside

1-Dithioethyl-2,3,4,6-tetra-O-acetyl-galactopyranoside from Step A (500 mg, 1.18 mmol) was dissolved in dry methanol (10 mL) and treated with methanolic sodium methoxide (1 M, 150 μL). After 2 h, the solution was neutralized with Amberlite 1R-120 (H⁺) resin, filtered and concentrated to give 1-dithioethyl-6-β-D-galactopyranoside as a white solid (300 mg, quant).

Step C

Coupling of 1-Dithioethyl-β-D-galactopyranoside to a Resin

1-Dithioethyl-6-β-D-galactopyranoside (200 mg, 780 μmol) was dissolved in dry pyridine (8 mL). Trityl chloride-resin (1 g, 950 μmol trityl chloride resin, loading 0.95 mmol/g of active chlorine, polymer matrix: copolystyrene-1% DVB, 200–400 mesh, Novabiochem) and DMAP (5 mg) were added and the mixture was heated for 24 h at 60° C. The resin was filtered off, and washed successively with methanol, tetrahydrofuran, dichloromethane and diethyl ether (10 mL each) to afford 1-dithioethyl-β-D-galactopyranoside covalently linked to the trityl resin through the hydroxyl group in the 6-position.

Step D

Generation of the Free Thiol on the Resin

The resin from Step C (50 mg) is swollen in dry tetrahydrofuran (1.5 mL). Dry methanol (300 μL), dithiothreitol (74 mg) and triethylamine (180 μL) are added and the mixture is shaken for 10 hours at room temperature. The resin is filtered off and washed successively with methanol, tetrahydrofuran, dichloromethane and diethyl ether (10 mL/each). IR (of intact beads): 2565 cm$^{-1}$ (SH stretch).

Step E

Michael Addition Reaction

The resin from Step D (50 mg) was swollen in dry N,N-dimethylformamide (1 mL) and then cyclohept-2-en-1-one (70 μl, 63 μmol) was added and the mixture was shaken at room temperature. After 2 hours, the resin was filtered off and washed successively with methanol, tetrahydrofuran, dichloromethane and diethyl ether (10 mL each).

Step F

Reductive Amination with an Amino Acid

The resin from Step E (50 mg) was swollen in dichloromethane (1 mL). Glycine tert-butyl ester hydrochloride (75 mg, 447 μmol), sodium sulfate (100 mg), sodium triacetoxyborohydride (63 mg, 297 μmol) and acetic acid (10 μL) were added at room temperature under argon atmosphere and the mixture shaken for 24 hours. The resin was then filtered off and washed successively with water, methanol, tetrahydrofuran and dichloromethane.

Step G

Cleavage from the 1-Thiogalactose Derivative from the Resin and Deblocking of the Amino Acid Ester The resin from Step F (50 mg) was shaken with trifluoroacetic acid (1 mL) and triisopropylsilane (20 μL) in dichloromethane (2 mL) at room temperature. After 3 hours, the resin was removed by filtration and washed with dichloromethane (10 mL). After adding toluene (10 mL), the solution was concentrated, then co-evaporated twice with toluene. The residue was dissolved in water (1 mL) and applied onto two $C_{18}$-Sep-Pak-cartridges (Waters Sep-Pak Plus). The $C_{18}$ silica was washed with water (4 mL) and the final product was eluted with 20% methanol and concentrated. After freeze drying from 5 mL of water, Nα-[3-(1-thio-β-D-galactopyranosyl)cyclohept-1-yl]glycine was obtained as a white powder (4.8 mg). The diastereomers ratio was 10:10:8:6 as determined by $^1$H-NMR.

$^1$H-NMR (360 MHz, $CD_3OD$, anomeric protons): δ4.36 (d, $J_{1,2}$=9.6 Hz), 4.40 (d, $J_{1,2}$=9.5 Hz), 4.44 (d, $J_{1,2}$=9.1 Hz), 4.45 (d, $J_{1,2}$=9.2 Hz); m/z calcd. for $C_{15}H_{27}NO_7S$ (M+H), 366.2, found 366.1.

EXAMPLE 4

Inhibition of Heat-Labile Enterotoxin Binding to $G_{D1b}$

In this example, 1-thiogalactose derivatives of formula I above were tested for their ability to inhibit the binding of heat-labile enterotoxin from *E. coli* to ganglioside $G_{D1b}$. This bioassay was conducted using the procedure described by A.-M. Svennerholm[13] except that ganglioside $G_{D1b}$ was used instead of ganglioside $G_{M1}$. The compounds of Examples A1, A2, A4–A7, A10, A11, B1, B2, B4–B7, B10, B11, C2, C5, C7, C10, C11, D2, D4, D5, E1, E2, E4, E10, E11, F1, F2, F5, F7, F10, F11, G2, G5, I2, I5, and J7 were tested in this bioassay. All of the compounds tested inhibited binding of heat-labile enterotoxin to ganglioside $G_{D1b}$ by at least 20%, except for the compounds of Examples A2, A5, A7, C10, D2 and G2, which did not inhibit binding by at least 20% at the concentration employed in the assay.

EXAMPLE 5

Inhibition of Cholera Toxin Binding to $G_{D1b}$

In this example, 1-thiogalactose derivatives of formula I above were tested for their ability to inhibit the binding of cholera toxin to ganglioside $G_{D1b}$. This bioassay was conducted using the following modification of the procedure described by A.-M. Svennerholm[13].

On day 1, microtiter plates (C96 Maxisorp) were coated with 100 μL of 1 mg/mL GD1b (disialoganglioside GD1b, MW=2127, Fluka) in PBS per well and incubated overnight at 37° C.

On day 2, the samples to be tested were diluted in BSA-Tween-PBS (0.1% BSA and 0.05% Tween-20 in PBS; Sigma). A total of 500 μL of each solution was prepared so that each point could be measured in quadruplicate. A concentration curve of 10, 20 and 30 ng/mL of CTB5-HRP (CT-B5 conjugated to HRP, Sigma, lyophilized, diluted in Tween-PBS) was prepared. For the inhibition experiments, 20 ng/mL of CTB5-HRP was used. The samples were then incubated for 2 hours at room temperature. After incubation, the plates were emptied and unattached ganglioside was removed by washing the plates 2 times with 200 μL PBS per well. Additional binding sites on the plastic surface were then blocked by incubating the plates with 200 μL of 1% BSA in PBS per well for 30 minutes at 37° C. The plates were then emptied and unattached BSA was removed by washing the plates 3 times with 200 μL of 0.05% Tween 20-PBS per well. Samples (100 μL) were added to 4 different wells and incubated for 30 minutes at room temperature. The plates were emptied and unattached BSA was removed by washing the plates 3 times with 200 μL of 0.05% Tween 20-PBS per well.

A substrate solution was freshly prepared for each ELISA. Each solution contained 10 mg of o-phenylenediamine (Sigma), 5 mL of 0.1 M sodium citrate (filter sterile or autoclaved), 5 mL of 0.1 M citric acid (filter sterile or autoclaved) and 4 mL of 30% $H_2O_2$. (Gloves should be worn since o-phenylenediamine is carcinogenic). The substrate solution (100 μL) was then added to each well and incubated for 30 minutes at room temperature. After incubation, the $OD_{450}$ was recorded. Under the conditions of the assay, D-galactose had an $IC_{50}$ of 30 mM.

The compounds of Examples A1–A10, B1–B6, B6A–B6L, B6Q, B6T, B7–B8, B10, C1–C3, C5, C7, C8, C10, D1–D5, D8, E1–E9, F1–F10, G2, G3, G5–G10, H2, H3, H5–H10, I1–I3, I5–I10, J1–J3 and J5–J10 were tested in this bioassay. All of the compounds tested inhibited binding of cholera toxin to ganglioside $G_{D1B}$ by at least 20%, except for the compounds of Examples A1, A3, A4, A6–A8, A10, B1, B3, B4, B10, C1, C3, C8, D3, E5, E8, E9, F1, F5–F7, F9, F10, G3, G7–G10, H2, H5, H8–H10, I2, I8–I10, J5–J10, which did not inhibit binding by at least 20% at the concentration employed in the assay (i.e., 1 mg/mL).

EXAMPLE 6

Neutralization of the Cytotonic Activity of CT and LT

In this example, the solid support material of Example 2 was tested for its ability to neutralize the cytotonic activity of CT and LT. The cytotonic activity of CT and LT was measured by the use of Chinese hamster ovary cells (CHO) that were maintained in Hams F12 media supplemented with 10% fetal bovine serum (FBS) in an atmosphere of 5% $CO_2$ at 37° C. Toxin samples were diluted 1:5 in Hams media and filter sterilized through 0.22 micron syringe filters. Samples were then serial 5-fold diluted in media and 100 μL of each dilution was added to wells with confluent monolayers of CHO cells and incubated for 24 h at 37° C. (under 5% $CO_2$). Each sample was analyzed two times. Cytotonic effects were readily visible after 24 h incubation by comparing wells with controls that do not contain toxin. After 24 h, the cells were fixed with 95% methanol and stained with Geimsa stain. Toxin containing samples from neutralization experiments were treated in an analogous fashion except that the percent neutralization was determined by comparing the endpoint dilutions of samples with and without the solid support material of Example 2.

A solution containing purified CT or LT (2, 10 or 20 μg in 1 mL PBS) was added to the solid support material of Example 2 (20 mg) in 1.5 mL microcentrifuge tubes and incubated at room temperature for I h on an end-over rotator. After incubation, the solid support material was allowed to settle to the bottom of the tubes and the supernatants were carefully removed. The supernatants were added to CHO cells and the cytotonic endpoint determined after incubation for 24 h as described above. The extent of reduction in the endpoint in the presence of the solid support material was determined by comparing with controls in which solid support material was not added.

Results showed that the solid support material of Example 2 neutralized more than 90% of CT and LT activity, regardless of toxin concentration, i.e., less than 10% toxin activity remained.

EXAMPLE 7

Inhibition of Colonization Factor Antigens (CFA pili) Binding to Glycophorin

In this example, 1-thiogalactose derivatives of formula I above were tested for their ability to inhibit CFA pili binding to glycophorin. Bacterial surface adhesion antigens such as CFA pili are a virulence factor expressed by certain enteric pathogens, including enterotoxigenic *E. coli*. These pili are important factors in bacterial attachment to cell surface receptors. Accordingly, inhibition of CFA pili binding is a useful test to determine whether a compound will inhibit the binding of a pathogenic microorganism to cell surface receptors.

Binding assays were done by coating microtitre wells with 50 μL of glycophorin (10 μg/mL) in PBS for 2 h at 37° C. The solution was removed by aspiration and replaced with 100 iL of 1% BSA in PBS containing 0.05% Tween 20 (PBST) and incubated at 37° C. for an additional 1 h. The microtitre wells were washed three times with 200 μL of PBST and then replaced with biotinylated CFA I (5 μg/mL) in 50 μL of PBS containing 0.05% BSA. After incubating for 2 h at 37° C. the binding reaction was stopped by aspirating the solutions and the plate was washed with PBST (3×200 μL). Avidin-peroxidase (50 μL of a 1/3000 dilution of a 1 mg/mL solution in PBST containing 0.05% BSA) was added and the plates were incubated for an additional 1 h. After washing the wells as described above, 100 μL of the substrate solution (0.42 mM tetramethylbenzidine (TMB) in 0.1 M sodium citrate buffer, pH 6.0, containing 0.5 AM urea peroxide) was added and the plates were incubated for 10 min at ambient temperature and the enzyme reaction stopped by adding 50 μL of 2 N $H_2SO_4$. Binding assays were done in triplicate and background binding was measured in wells coated with BSA only.

Binding inhibition assays were done using oligosaccharide analogs at a concentration of 1 mg/mL in PBS. Inhibitors were preincubated with biotinylated CFA I pili (5 μ/mL) for 1 h at 37° C. prior to adding to glycophorin-coated microtitre wells as outlined above. o-Nitrophenyl-β-D-galactose was utilized as a control inhibitor for these experiments.

The 1-thiogalactose derivatives of Examples A1–A10, B1–B8, B10, C1–C3, C5, C7, C8, C10, D1–D5, D8, D10, E1–E10, F1–F10, G1–G3, G5–G10, H1–H3, H5–H10, I1–I3, I5–I10, J1–J3 and J5–J10 were tested. Of these compounds, the results showed that the compounds of Examples B2, B5, H2, H3, H5, H6, H7, H8, H9, H10, I1, I2 and J9 inhibited CFA I pili binding to glycophorin, with the amount of inhibition ranging from 13 to 71%. The compounds having a histidine or a tryptophan (Group H and I) moiety were particularly good inhibitors in this experiment.

From the foregoing description, various modifications and changes in the composition and method will occur to those skilled in the art. All such modifications coming within the scope of the appended claims are intended to be included therein.

I claim:

1. A compound of formula I:

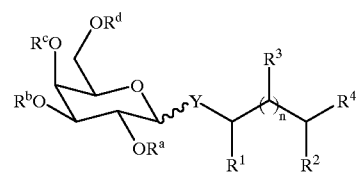

wherein
- $R^1$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;
- $R^2$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;
- $R^3$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;
- or $R^1$ and $R^2$, or $R^1$ and $R^3$, or $R^2$ and $R^3$, or $R^1$, $R^2$ and $R^3$ can be joined, together with the carbon atoms to which $R^1$ and/or $R^2$ and/or $R^3$ are attached, to form a cycloalkyl, cycloalkyl substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, aryloxy, carboxy, carboxyalkyl, cyano, halo, nitro, heteroaryl and trihalomethyl, cycloalkenyl or heterocyclic ring;

$R^4$ is selected from the group consisting of —$XR^5$, —$XC(W)R^6$, —$XC(W)X'R^7$ and —$C(W)XR^8$; wherein W is selected from the group consisting of oxygen, sulfur and NH; and X and X' are each independently selected from the group consisting of oxygen, sulfur and —$NR^9$—, wherein $R^9$ is selected from the group consisting of hydrogen and alkyl; or when $R^4$ is —$XR^5$ and $R^5$ is not hydrogen, X can also be selected from the group consisting of —S(O)— and —$SO_2$—;

$R^5$ is selected from the group consisting of hydrogen, alkyl, alkenyl, alkaryl, alkoxyalkyl, aryl, cycloalkyl, cycloalkenyl, heteroaryl, heterocyclic and thioalkoxyalkyl, and when X is —$NR^9$—, then $R^9$ together with X can form an amino acid; or $R^5$ and $R^1$, or $R^5$ and $R^2$, or $R^5$ and $R^3$ can be joined, together with X of the —$XR^5$ group and the carbon atoms to which $R^1$ and/or $R^2$ and/or $R^3$ are attached, to form a heterocyclic ring;

$R^6$ is selected from the group consisting of alkyl, alkenyl, alkaryl, alkoxyalkyl, aryl, cycloalkyl, cycloalkenyl, heteroaryl, heterocyclic and thioalkoxyalkyl; or $R^6$ and $R^1$, or $R^6$ and $R^2$, or $R^6$ and $R^3$ can be joined, together with the —XC(W)— moiety of the —$XC(W)R^6$ group and the carbon atoms to which $R^1$ and/or $R^2$ and/or $R^3$ are attached, to form a heterocyclic ring;

$R^7$ is selected from the group consisting of alkyl, alkenyl, alkaryl, alkoxyalkyl, aryl, cycloalkyl, cycloalkenyl, heteroaryl, heterocyclic and thioalkoxyalkyl; or $R^7$ and $R^1$, or $R^7$ and $R^2$, or $R^7$ and $R^3$ can be joined, together with the —XC(W)X'— moiety of the —$XC(W)X'R^7$ group and the carbon atoms to which $R^1$ and/or $R^2$ and/or $R^3$ are attached, to form a heterocyclic ring;

$R^8$ is selected from the group consisting of alkyl, alkenyl, alkaryl, alkoxyalkyl, aryl, cycloalkyl, cycloalkenyl, heteroaryl, heterocyclic and thioalkoxyalkyl; or $R^8$ and $R^1$, or $R^8$ and $R^2$, or $R^8$ and $R^3$ can be joined, together with the —C(W)X— moiety of the —$C(W)XR^8$ group and the carbon atoms to which $R^1$, $R^2$ and/or $R^3$ are attached, to form a heterocyclic ring;

Y is selected from the group consisting of sulfur, —S(O)— and —$S(O)_2$—;

$R^a$, $R^b$, $R^c$ and $R^d$ are each independently selected from the group consisting of hydrogen; sulfate; —$C(O)R^{10}$, wherein $R^{10}$ is selected from the group consisting of alkyl, alkenyl, alkaryl, alkoxyalkyl, aryl, cycloalkyl, cycloalkenyl, heteroaryl, heterocyclic and thioalkoxyalkyl; and —$P(O)(OR^{11})_2$, wherein each $R^{11}$ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl; and n is an integer equal to 0 or 1; or pharmaceutically acceptable salts thereof;

with the proviso that when $R^1$ and $R^2$ are joined, together with the carbon atoms to which $R^1$, $R^2$ and $R^3$ are attached, to form a cyclopentyl ring, $R^3$ is hydrogen, $R^4$ is —$XR^5$, X is oxygen, Y is sulfur, $R^a$, $R^b$, $R^c$ and $R^d$ are each hydrogen and n is 1, then $R^5$ is not hydrogen; and with the proviso that when $R^1$ and $R^2$ are each hydrogen, $R^4$ is —$XR^5$, X is oxygen, Y is sulfur, $R^a$, $R^b$, $R^c$, and $R^d$ are each hydrogen and n is 0, then $R^5$ is not hydrogen or phenyl; and when $R^1$ and $R^2$ are each hydrogen, $R^4$ is —$XR^5$, X is —NH—, Y is sulfur, $R^a$, $R^b$, $R^c$ and $R^d$ are each hydrogen and n is 0, then $R^5$ is not phenyl.

2. A compound of claim 1 wherein the compound of formula I is an α-anomer.

3. A compound of claim 1 wherein the compound of formula I is a β-anomer.

4. A compound of claim 1 wherein, when n is 0, $R^1$ and $R^2$ are joined, together with the carbon to which they are attached, to form a cycloalkyl ring having 5 to 7 carbon atoms or a cycloalkyl ring having 5 to 7 carbon atoms substituted with 1 to 3 alkyl groups.

5. A compound of claim 4 wherein $R^1$ and $R^2$ are joined, together with the carbon to which they are attached, to form a cyclopentane or cyclohexane ring.

6. A compound of claim 1 wherein, when n is 1, $R^1$ and $R^2$ are joined, together with the carbon atoms to which $R^1$, $R^2$ and $R^3$ are attached, to form a cycloalkyl ring having 5 to 7 carbon atoms or a cycloalkyl ring having 5 to 7 carbon atoms substituted with 1 to 3 alkyl groups.

7. A compound of claim 6 wherein $R^1$ and $R^2$ are joined, together with the carbon atoms to which $R^1$, $R^2$ and $R^3$ are attached, to form a cyclopentane, dimethylcyclopentane, cyclohexane, dimethylcyclohexane or cycloheptane ring.

8. A compound of claim 6 wherein $R^4$ is —$XR^5$, where X is —NH— and $R^5$ is cycloalkyl.

9. A compound of claim 1 wherein, when n is 1, $R^2$ and $R^3$ are joined, together with the carbon atoms to which they are attached, to form a norbornene ring.

10. A compound of claim 1 wherein $R^4$ is —$XR^5$, where X and $R^5$ form an amino group, a hydroxy group or an amino acid selected from the group consisting of glycine, β-alanine, leucine, histidine, tryptophan and arginine.

11. A compound of claim 1 wherein $R^4$ is —$XC(O)R^6$, where X is —NH— and $R^6$ is methyl or 2-carboxyphenyl.

12. A compound selected from the group consisting of:
2-hydroxycyclopent-1-yl 1-thio-β-D-galactopyranoside,
2-hydroxycyclohex-1-yl 1-thio-β-D-galactopyranoside,
3-hydroxy-1-phenylbut-1-yl 1-thio-β-D-galactopyranoside,
(3-hydroxynorborn-2-yl)methyl 1-thio-β-D-galactopyranoside,
3-hydroxycyclohept-1-yl 1-thio-β-D-galactopyranoside,
3-hydroxycyclohept-1-yl 1-thio-α-D-galactopyranoside,
2,2-dimethyl-4-hydroxycyclopent-1-yl 1-thio-β-D-galactopyranoside,
4-hydroxypent-2-yl 1-thio-β-D-galactopyranoside,
2,2-dimethyl-5-hydroxycyclohex-1-yl 1-thio-β-D-galactopyranoside,
3-hydroxycyclohex-1-yl 1-thio-β-D-galactopyranoside,
4,4-dimethyl-3-hydroxycyclohex-1-yl 1-thio-β-D-galactopyranoside,
2-aminocyclopent-1-yl 1-thio-β-D-galactopyranoside,
2-aminocyclohex-1-yl 1-thio-β-D-galactopyranoside,
3-amino-1-phenylbut-1-yl 1-thio-β-D-galactopyranoside,
(3-aminonorborn-2-yl)methyl 1-thio-β-D-galactopyranoside,
3-aminocyclohept-1-yl 1-thio-β-D-galactopyranoside,
2,2-dimethyl-4-aminocyclopent-1-yl 1-thio-β-D-galactopyranoside,
3-aminocyclopent-1-yl 1-thio-β-D-galactopyranoside,
4-aminopent-2-yl 1-thio-β-D-galactopyranoside,
3-aminocyclohex-1-yl 1-thio-β-D-galactopyranoside,
3-amino-4,4-dimethylcyclohex-1-yl 1-thio-β-D-galactopyranoside, 2-acetamidocyclopent-1-yl 1-thio-β-D-galactopyranoside,
2-acetamidocyclohex-1-yl 1-thio-β-D-galactopyranoside,
3-acetamido-1-phenylbut-1-yl 1-thio-β-D-galactopyranoside,
3-acetamidocyclohept-1-yl 1-thio-β-D-galactopyranoside,
3-acetamidocyclopent-1-yl 1-thio-β-D-galactopyranoside,
4-acetamidopent-2-yl 1-thio-β-D-galactopyranoside,
3-acetamidocyclohexyl 1-thio-β-D-galactopyranoside,
3-acetamido-4,4-dimethylcyclohexyl 1-thio-β-D-galactopyranoside,
2-(2-carboxybenzamido)cyclopent-1-yl 1-thio-β-D-galactopyranoside,
2-(2-carboxybenzamido)cyclohex-1-yl 1-thio-β-D-galactopyranoside,
3-(2-carboxybenzamido)-1-phenylbut-1-yl 1-thio-β-D-galactopyranoside,
[3-(carboxybenzamido)norborn-2-yl]methyl 1-thio-β-D-galactopyranoside,
3-(2-carboxybenzamido)cyclohept-1-yl 1-thio-β-D-galactopyranoside,
3-(2-carboxybenzamido)pent-2-yl 1-thio-β-D-galactopyranoside,
5-(2-carboxybenzamido)-2,2-dimethylcyclohex-1-yl 1-thio-β-D-galactopyranoside,
3-(2-carboxybenzamido)cyclohex-1-yl 1-thio-β-D-galactopyranoside,
Nα-[2-(1-thio-β-D-galactopyranosyl)cyclopent-1-yl] glycine,
Nα-[2-(1-thio-β-D-galactopyranosyl)cyclohex-1-yl] glycine,
Nα-[4-phenyl-4-(1-thio-β-D-galactopyranosyl)but-2-yl] glycine,
Nα-[3-((1-thio-β-D-galactopyranosyl)methyl)norborn-2-yl] glycine,
Nα-[3-(1-thio-β-D-galactopyranosyl)cyclohept-1-yl] glycine,
Nα-[3 -(1-thio-α-D-galactopyranosyl)cyclohept-1-yl] glycine,
Nα-[4,4-dimethyl-3-(1-thio-β-D-galactopyranosyl)cyclopent-1-yl]glycine,
Nα-[3-(1-thio-β-D-galactopyranosyl)cyclopent-1-yl] glycine,
Nα-[4-(1-thio-β-D-galactopyranosyl)pent-2-yl]glycine,
Nα-[4,4-dimethyl-3-(1-thio-β-D-galactopyranosyl)cyclohex-1-yl]glycine,
Nα-[3-(1-thio-β-D-galactopyranosyl)cyclohex-1-yl] glycine,
Nα-[5-(1-thio-β-D-galactopyranosyl)-2,2-dimethylcyclohex-1-yl]glycine,
Nβ-[2-(1-thio-β-D-galactopyranosyl)cyclopent-1-yl]-β-alanine,
Nβ-[2-(1-thio-β-D-galactopyranosyl)cyclohex-1-yl]-β-alanine,
Nβ-[4-phenyl-4-(1-thio-β-D-galactopyranosyl)but-2-yl]-β-alanine,
Nβ-[3-((1-thio-β-D-galactopyranosyl)methyl)norborn-2-yl]-β-alanine,
Nβ-[3 -(1-thio-β-D-galactopyranosyl)cyclohept-1-yl]-β-alanine,
Nβ-[4,4-dimethyl-3-(1-thio-β-D-galactopyranosyl)cyclopent-1-yl]-β-alanine,
Nβ-[3-(1-thio-β-D-galactopyranosyl)cyclopent-1-yl]-β-alanine,
Nβ-[4-(1-thio-β-D-galactopyranosyl)pent-2-yl]-β-alanine,
Nβ-[4,4-dimethyl-3-(1-thio-β-D-galactopyranosyl)cyclohex-1-yl]-β-alanine,
Nβ-[3-(1-thio-β-D-galactopyranosyl)cyclohex-1-yl]-β-alanine,
Nβ-[5-(1-thio-β-D-galactopyranosyl)-2,2-dimethylcyclohex-1-yl]-β-alanine,
Nα-[2-(1-thio-β-D-galactopyranosyl)cyclopent-1-yl]-L-leucine,
Nα-[2-(1-thio-β-D-galactopyranosyl)cyclohex-1-yl]-L-leucine,
Nα-[4-phenyl-4-(1-thio-β-D-galactopyranosyl)but-2-yl]-L-leucine,
Nα-[1-(1-thio-β-D-galactopyranosyl)cyclohept-3-yl]-L-leucine,
Nα-[4,4-dimethyl-3-(1-thio-β-D-galactopyranosyl)cyclopent-1-yl]-L-leucine,
Nα-[3-(1-thio-β-D-galactopyranosyl)cyclopent-1-yl]-L-leucine,
Nα-[4-(1-thio-β-D-galactopyranosyl)pent-2-yl]-L-leucine,
Nα-[4,4-dimethyl-3-(1-thio-β-D-galactopyranosyl)cyclohex-1-yl]-L-leucine,
Nα-[3-(1-thio-β-D-galactopyranosyl)cyclohex-1-yl]-L-leucine,
Nα-[2-(1-thio-β-D-galactopyranosyl)cyclopent-1-yl]-L-histidine,
Nα-[2-(1-thio-β-D-galactopyranosyl)cyclohex-1-yl]-L-histidine,
Nα-[4-phenyl-4-(1-thio-β-D-galactopyranosyl)but-2-yl]-L-histidine,
Nα-[3-(1-thio-β-D-galactopyranosyl)cyclohept-1-yl]-L-histidine,
Nα-[4,4-dimethyl-3-(1-thio-β-D-galactopyranosyl)cyclopent-1-yl]-L-histidine,
Nα-[3-(1-thio-β-D-galactopyranosyl)cyclopent-1-yl]-L-histidine,
Nα-[4-(1-thio-β-D-galactopyranosyl)pent-2-yl]-L-histidine,
Nα-[4,4-dimethyl-3-(1-thio-β-D-galactopyranosyl)cyclohex-1-yl]-L-histidine,
Nα-[3-(1-thio-β-D-galactopyranosyl)cyclohex-1-yl]-L-histidine,
Nα-[2-(1-thio-β-D-galactopyranosyl)cyclopent-1-yl]-L-tryptophan,
Nα-[2-(1-thio-β-D-galactopyranosyl)cyclohex-1-yl]-L-tryptophan,
Nα-[4-phenyl-4-(1-thio-β-D-galactopyranosyl)but-2-yl]-L-tryptophan,
Nα-[3-(1-thio-β-D-galactopyranosyl)cyclohept-1-yl]-L-tryptophan,
Nα-[4,4-dimethyl-3-(1-thio-β-D-galactopyranosyl)cyclopent-1-yl]-L-tryptophan,
Nα-[3-(1-thio-β-D-galactopyranosyl)cyclopent-1-yl]-L-tryptophan,
Nα-[4-(1-thio-β-D-galactopyranosyl)pent-2-yl]-L-tryptophan,
Nα-[4,4-dimethyl-3-(1-thio-β-D-galactopyranosyl)cyclohex-1-yl]-L-tryptophan,
Nα-[3 -(1-thio-β-D-galactopyranosyl)cyclohex-1-yl]-L-tryptophan,
Nα-[2-(1-thio-β-D-galactopyranosyl)cyclopent-1-yl]-L-arginine-,
Nα-[2-(1-thio-β-D-galactopyranosyl)cyclohex-1-yl]-L-arginine,
Nα-[4-phenyl-4-(1-thio-β-D-galactopyranosyl)but-2-yl]-L-arginine,
Nα-[3-(1-thio-β-D-galactopyranosyl)cyclohept-1-yl]-L-arginine,
Nα-[4,4-dimethyl-3-(1-thio-β-D-galactopyranosyl)cyclopent-1-yl]-L-arginine,
Nα-[3-(1-thio-β-D-galactopyranosyl)cyclopent-1-yl]-L-arginine,
Nα-[4-(1-thio-β-D-galactopyranosyl)pent-2-yl]-L-arginine, Nα-[4,4-dimethyl-3-(1-thio-β-D-galactopyranosyl) cyclohex-1-yl]-L-arginine,
Nα-[3-(1-thio-β-D-galactopyranosyl)cyclohex-1-yl]-L-arginine,
2,2-dimethyl-4-(methylamino)cyclopent-1-yl 1-thio-β-D-galactopyranoside,
2,2-dimethyl-4-(isopropylamino)cyclopent-1-yl 1-thio-β-D-galactopyranoside,
2,2-dimethyl-4-(n-propylamino)cyclopent-1-yl 1-thio-β-D-galactopyranoside,
2,2-dimethyl-4-((R)-sec-butylamino)cyclopent-1-yl 1-thio-β-D-galactopyranoside,
2,2-dimethyl-4-((S)-sec-butylamino)cyclopent-1-yl 1-thio-β-D-galactopyranoside,
2,2-dimethyl-4-(pent-3-ylamino)cyclopent-1-yl 1-thio-β-D-galactopyranoside,
2,2-dimethyl-4-(n-hexylamino)cyclopent-1-yl 1-thio-β-D-galactopyranoside,
2,2-dimethyl-4-(cyclobutylamino)cyclopent-1-yl 1-thio-β-D-galactopyranoside,
2,2-dimethyl-4-(3,3-dimethylcyclobut-1-ylamino) cyclopent-1-yl 1-thio-β-D-galactopyranoside,
2,2-dimethyl-4-(cyclopentylamino)cyclopent-1-yl 1-thio-β-D-galactopyranoside,
2,2-dimethyl-4-(3-methylcyclopent-1-ylamino)cyclopent-1-yl 1-thio-β-D-galactopyranoside,
2,2-dimethyl-4-(3,3-dimethylcyclopent-1-ylamino) cyclopent-1-yl 1-thio-β-D-galactopyranoside,
2,2-dimethyl-4-(cyclohexylamino)cyclopent-1-yl 1-thio-β-D-galactopyranoside,
2,2-dimethyl-4-(3-methylcyclohex-1-ylamino)cyclopent-1-yl 1-thio-β-D-galactopyranoside,
2,2-dimethyl-4-(4-methylcyclohex-1-ylamino)cyclopent-1-yl 1-thio-β-D-galactopyranoside,
and pharmaceutically acceptable salts thereof.

13. A compound of formula I:

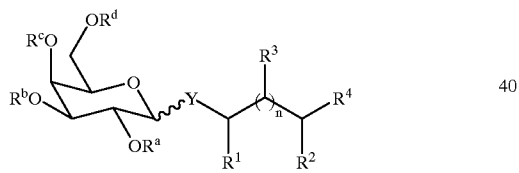

I wherein
$R^1$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;
$R^2$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;
$R^3$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;
or $R^1$ and $R^2$, or $R^1$ and $R^3$, or $R^2$ and $R^3$, or $R^1$, $R^2$ and $R^3$ can be joined, together with the carbon atoms to which $R^1$ and/or $R^2$ and/or $R^3$ are attached, to form a cycloalkyl, cycloalkyl substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, aryloxy, carboxy, carboxyalkyl, cyano, halo, nitro, heteroaryl and trihalomethyl, cycloalkenyl or heterocyclic ring;

$R^4$ is selected from the group consisting of —$XR^5$, —$XC(W)R^6$, —$XC(W)X'R^7$ and —$C(W)XR^8$; wherein W is selected from the group consisting of oxygen, sulfur and NH; and X and X' are each independently selected from the group consisting of oxygen, sulfur and —$NR^9$—, wherein $R^9$ is selected from the group consisting of hydrogen and alkyl; or when $R^4$ is —$XR^5$ and $R^5$ is not hydrogen, X can also be selected from the group consisting of —S(O)— and —$SO_2$—;
$R^5$ is selected from the group consisting of hydrogen, alkyl, alkenyl, alkaryl, alkoxyalkyl, aryl, cycloalkyl, cycloalkenyl, heteroaryl, heterocyclic and thioalkoxyalkyl, and when X is —$NR^9$—, then $R^9$ together with X can form an amino acid; or $R^5$ and $R^1$, or $R^5$ and $R^2$, or $R^5$ and $R^3$ can be joined, together with X of the —$XR^5$ group and the carbon atoms to which $R^1$ and/or $R^2$ and/or $R^3$ are attached, to form a heterocyclic ring;
$R^6$ is selected from the group consisting of alkyl, alkenyl, alkaryl, alkoxyalkyl, aryl, cycloalkyl, cycloalkenyl, heteroaryl, heterocyclic and thioalkoxyalkyl; or $R^6$ and $R^1$, or $R^6$ and $R^2$, or $R^6$ and $R^3$ can be joined, together with the —XC(W)— moiety of the —$XC(W)R^6$ group and the carbon atoms to which $R^1$ and/or $R^2$ and/or $R^3$ are attached, to form a heterocyclic ring;
$R^7$ is selected from the group consisting of alkyl, alkenyl, alkaryl, alkoxyalkyl, aryl, cycloalkyl, cycloalkenyl, heteroaryl, heterocyclic and thioalkoxyalkyl; or $R^7$ and $R^1$, or $R^7$ and $R^2$, or $R^7$ and $R^3$ can be joined, together with the —XC(W)X'— moiety of the —$XC(W)X'R^7$ group and the carbon atoms to which $R^1$ and/or $R^2$ and/or $R^3$ are attached, to form a heterocyclic ring;
$R^8$ is selected from the group consisting of alkyl, alkenyl, alkaryl, alkoxyalkyl, aryl, cycloalkyl, cycloalkenyl, heteroaryl, heterocyclic and thioalkoxyalkyl; or $R^8$ and $R^1$, or $R^8$ and $R^2$, or $R^8$ and $R^3$ can be joined, together with the —C(W)X— moiety of the —$C(W)XR^8$ group and the carbon atoms to which $R^1$, $R^2$ and/or $R^3$ are attached, to form a heterocyclic ring;
Y is selected from the group consisting of sulfur, —S(O)— and —$S(O)_2$—;
$R^a$, $R^b$, $R^c$ and $R^d$ are each independently selected from the group consisting of hydrogen; sulfate; —$C(O)R^{10}$, wherein $R^{10}$ is selected from the group consisting of alkyl, alkenyl, alkaryl, alkoxyalkyl, aryl, cycloalkyl, cycloalkenyl, heteroaryl, heterocyclic and thioalkoxyalkyl; and —$P(O)(OR^{11})_2$, wherein each $R^{11}$ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl; and
n is an integer equal to 0 or 1; or pharmaceutically acceptable salts thereof;
wherein said compound inhibits the binding of a toxin to its receptor, or said compound inhibits the binding of an organism to its cell surface receptor;
and with the proviso that when $R^1$ and $R^2$ are each hydrogen, $R^4$ is —$XR^5$, X is oxygen, Y is sulfur, $R^a$, $R^b$, $R^c$, and $R^d$ are each hydrogen and n is 0, then $R^5$ is not hydrogen or phenyl; and when $R^1$ and $R^2$ are each hydrogen, $R^4$ is —$XR^5$, X is —NH—, Y is sulfur, $R^a$, $R^b$, $R^c$, and $R^d$ are each hydrogen and n is 0, then $R^5$ is not phenyl.

14. A compound of claim 13 wherein the toxin is heat-labile enterotoxin or cholera toxin.

15. A compound of claim 13 wherein the organism is *Vibrio cholerae* or an enterotoxigenic strain of *Escherichia coli*.

16. A compound of claim 13 wherein the compound of formula I is an α-anomer.

17. A compound of claim 13 wherein the compound of formula I is a β-anomer.

18. A compound of claim 13 wherein, when n is 0, $R^1$ and $R^2$ are joined, together with the carbon to which they are attached, to form a cycloalkyl ring having 5 to 7 carbon atoms or a cycloalkyl ring having 5 to 7 carbon atoms substituted with 1 to 3 alkyl groups.

19. A compound of claim 13 wherein, when n is 1, $R^1$ and $R^2$ are joined, together with the carbon atoms to which $R^1$, $R^2$ and $R^3$ are attached, to form a cycloalkyl ring having 5 to 7 carbon atoms or a cycloalkyl ring having 5 to 7 carbon atoms substituted with 1 to 3 alkyl groups.

20. A compound of claim 19 wherein $R^4$ is —$XR^5$, where X is —NH— and $R^5$ is cycloalkyl.

21. A compound of claim 13 wherein, when n is 1, $R^2$ and $R^3$ are joined, together with the carbon atoms to which they are attached, to form a norbornene ring.

22. A compound of claim 13 wherein $R^4$ is —$XR^5$, where X and $R^5$ form an amino group, a hydroxy group or an amino acid selected from the group consisting of glycine, β-alanine, leucine, histidine, tryptophan and arginine; or $R^4$ is —$XC(O)R^6$, where X is —NH— and $R^6$ is methyl or 2-carboxyphenyl.

23. A pharmaceutical composition comprising from 1 to 99 weight percent of a pharmaceutically acceptable carrier and from 1 to 99 weight percent of at least one compound of formula I:

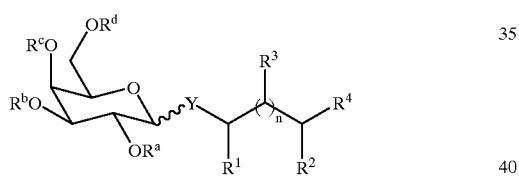

I wherein
$R^1$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;

$R^2$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;

$R^3$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;

or $R^1$ and $R^2$, or $R^1$ and $R^3$, or $R^2$ and $R^3$, or $R^1$, $R^2$ and $R^3$ can be joined, together with the carbon atoms to which $R^1$ and/or $R^2$ and/or $R^3$ are attached, to form a cycloalkyl, cycloalkyl substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, aryloxy, carboxy, carboxyalkyl, cyano, halo, nitro, heteroaryl and trihalomethyl, cycloalkenyl or heterocyclic ring;

$R^4$ is selected from the group consisting of —$XR^5$, —$XC(W)R^6$, —$XC(W)X'R^7$ and —$C(W)XR^8$;

wherein W is selected from the group consisting of oxygen, sulfur and NH; and X and X' are each independently selected from the group consisting of oxygen, sulfur and —$NR^9$—, wherein $R^9$ is selected from the group consisting of hydrogen and alkyl; or when $R^4$ is —$XR^5$ and $R^5$ is not hydrogen, X can also be selected from the group consisting of —S(O)— and —$SO_2$—;

$R^5$ is selected from the group consisting of hydrogen, alkyl, alkenyl, alkaryl, alkoxyalkyl, aryl, cycloalkyl, cycloalkenyl, heteroaryl, heterocyclic and thioalkoxyalkyl, and when X is —$NR^9$—, then $R^9$ together with X can form an amino acid; or $R^5$ and $R^1$, or $R^5$ and $R^2$, or $R^5$ and $R^3$ can be joined, together with X of the —$XR^5$ group and the carbon atoms to which $R^1$ and/or $R^2$ and/or $R^3$ are attached, to form a heterocyclic ring;

$R^6$ is selected from the group consisting of alkyl, alkenyl, alkaryl, alkoxyalkyl, aryl, cycloalkyl, cycloalkenyl, heteroaryl, heterocyclic and thioalkoxyalkyl; or $R^6$ and $R^1$, or $R^6$ and $R^2$, or $R^6$ and $R^3$ can be joined, together with the —XC(W)— moiety of the —$XC(W)R^6$ group and the carbon atoms to which $R^1$ and/or $R^2$ and/or $R^3$ are attached, to form a heterocyclic ring;

$R^7$ is selected from the group consisting of alkyl, alkenyl, alkaryl, alkoxyalkyl, aryl, cycloalkyl, cycloalkenyl, heteroaryl, heterocyclic and thioalkoxyalkyl; or $R^7$ and $R^1$, or $R^7$ and $R^2$, or $R^7$ and $R^3$ can be joined, together with the —XC(W)X'— moiety of the —$XC(W)X'R^7$ group and the carbon atoms to which $R^1$ and/or $R^2$ and/or $R^3$ are attached, to form a heterocyclic ring;

$R^8$ is selected from the group consisting of alkyl, alkenyl, alkaryl, alkoxyalkyl, aryl, cycloalkyl, cycloalkenyl, heteroaryl, heterocyclic and thioalkoxyalkyl; or $R^8$ and $R^1$, or $R^8$ and $R^2$, or $R^8$ and $R^3$ can be joined, together with the —C(W)X— moiety of the —$C(W)XR^8$ group and the carbon atoms to which $R^1$, $R^2$ and/or $R^3$ are attached, to form a heterocyclic ring;

Y is selected from the group consisting of sulfur, —S(O)— and —$S(O)_2$—;

$R^a$, $R^b$, $R^c$ and $R^d$ are each independently selected from the group consisting of hydrogen; sulfate; —$C(O)R^{10}$, wherein $R^{10}$ is selected from the group consisting of alkyl, alkenyl, alkaryl, alkoxyalkyl, aryl, cycloalkyl, cycloalkenyl, heteroaryl, heterocyclic and thioalkoxyalkyl; and —$P(O)(OR^{11})_2$, wherein each $R^{11}$ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl; and n is an integer equal to 0 or 1; or pharmaceutically acceptable salts thereof;

with the proviso that when $R^1$ and $R^2$ are joined, together with the carbon atoms to which $R^1$, $R^2$ and $R^3$ are attached, to form a cyclopentyl ring, $R^3$ is hydrogen, $R^4$ is —$XR^5$, X is oxygen, Y is sulfur, $R^a$, $R^b$, $R^c$ and $R^d$ are each hydrogen and n is 1, then $R^5$ is not hydrogen;

and with the proviso that when $R^1$ and $R^2$ are each hydrogen, $R^4$ is —$XR^5$, X is oxygen, Y is sulfur, $R^a$, $R^b$, $R^c$ and $R^d$ are each hydrogen and n is 0, then $R^5$ is not hydrogen or phenyl; and when $R^1$ and $R^2$ are each hydrogen, $R^4$ is —$XR^5$, X is —NH—, Y is sulfur, $R^a$, $R^b$, $R^c$, and $R^d$ are each hydrogen and n is 0, then $R^5$ is not phenyl.

24. The pharmaceutical composition of claim 23 wherein, when n is 0, $R^1$ and $R^2$ are joined, together with the carbon to which they are attached, to form a cycloalkyl ring having 5 to 7 carbon atoms or a cycloalkyl ring having 5 to 7 carbon atoms substituted with 1 to 3 alkyl groups.

25. The pharmaceutical composition of claim 23 wherein, when n is 1, $R^1$ and $R^2$ are joined, together with the carbon atoms to which $R^1$, $R^2$ and $R^3$ are attached, to form a cycloalkyl ring having 5 to 7 carbon atoms or a cycloalkyl ring having 5 to 7 carbon atoms substituted with 1 to 3 alkyl groups.

26. The pharmaceutical composition of claim 25 wherein $R^4$ is —$XR^5$, where X is —NH— and $R^5$ is cycloalkyl.

27. The pharmaceutical composition of claim 23 wherein, when n is 1, $R^2$ and $R^3$ are joined, together with the carbon atoms to which they are attached, to form a norbornene ring.

28. The pharmaceutical composition of claim 23 wherein $R^4$ is —$XR^5$, where X and $R^5$ form an amino group, a hydroxy group or an amino acid selected from the group consisting of glycine, β-alanine, leucine, histidine, tryptophan and arginine; or $R^4$ is —$XC(O)R^6$, where X is —NH— and $R^6$ is methyl or 2-carboxyphenyl.

29. A pharmaceutical composition comprising from 1 to 99 weight percent of a pharmaceutically acceptable carrier and from 1 to 99 weight percent of at least one compound selected from the group consisting of:
2-hydroxycyclopent-1-yl 1-thio-β-D-galactopyranoside,
2-hydroxycyclohex-1-yl 1-thio-β-D-galactopyranoside,
3-hydroxy-1-phenylbut-1-yl 1-thio-β-D-galactopyranoside,
(3-hydroxynorborn-2-yl)methyl 1-thio-β-D-galactopyranoside,
3-hydroxycyclohept-1-yl 1-thio-β-D-galactopyranoside,
3-hydroxycyclohept-1-yl 1-thio-α-D-galactopyranoside,
2,2-dimethyl-4-hydroxycyclopent-1-yl 1-thio-β-D-galactopyranoside,
4-hydroxypent-2-yl 1-thio-β-D-galactopyranoside,
2,2-dimethyl-5-hydroxycyclohex-1-yl 1-thio-β-D-galactopyranoside,
3-hydroxycyclohex-1-yl 1-thio-β-D-galactopyranoside,
4,4-dimethyl-3-hydroxycyclohex-1-yl 1-thio-β-D-galactopyranoside,
2-aminocyclopent-1-yl 1-thio-β-D-galactopyranoside,
2-aminocyclohex-1-yl 1-thio-β-D-galactopyranoside,
3-amino-1-phenylbut-1-yl 1-thio-β-D-galactopyranoside,
(3-aminonorborn-2-yl)methyl 1-thio-β-D-galactopyranoside,
3-aminocyclohept-1-yl 1-thio-β-D-galactopyranoside,
2,2-dimethyl-4-aminocyclopent-1-yl 1-thio-β-D-galactopyranoside,
3-aminocyclopent-1-yl 1-thio-β-D-galactopyranoside,
4-aminopent-2-yl 1-thio-β-D-galactopyranoside,
3-aminocyclohex-1-yl 1-thio-β-D-galactopyranoside,
3-amino-4,4-dimethylcyclohex-1-yl 1-thio-β-D-galactopyranoside,
2-acetamidocyclopent-1-yl 1-thio-β-D-galactopyranoside,
2-acetamidocyclohex-1-yl 1-thio-β-D-galactopyranoside,
3-acetamido-1-phenylbut-1-yl 1-thio-β-D-galactopyranoside,
3-acetamidocyclohept-1-yl 1-thio-β-D-galactopyranoside,
3-acetamidocyclopent-1-yl 1-thio-β-D-galactopyranoside,
4-acetamidopent-2-yl 1-thio-β-D-galactopyranoside,
3-acetamidocyclohexyl 1-thio-β-D-galactopyranoside,
3-acetamido-4,4-dimethylcyclohexyl 1-thio-β-D-galactopyranoside,
2-(2-carboxybenzamido)cyclopent-1-yl 1-thio-β-D-galactopyranoside,
2-(2-carboxybenzamido)cyclohex-1-yl 1-thio-β-D-galactopyranoside,
3-(2-carboxybenzamido)-1-phenylbut-1-yl 1-thio-β-D-galactopyranoside,
[3-(carboxybenzamido)norborn-2-yl]methyl 1-thio-β-D-galactopyranoside,
3-(2-carboxybenzamido)cyclohept-1-yl 1-thio-β-D-galactopyranoside,
3-(2-carboxybenzamido)pent-2-yl 1-thio-β-D-galactopyranoside,
5-(2-carboxybenzamido)-2,2-dimethylcyclohex-1-yl 1-thio-β-D-galactopyranoside
3-(2-carboxybenzamido)cyclohex-1-yl 1-thio-β-D-galactopyranoside,
Nα-[2-(1-thio-β-D-galactopyranosyl)cyclopent-1-yl]glycine,
Nα-[2-(1-thio-β-D-galactopyranosyl)cyclohex-1-yl]glycine,
Nα-[4-phenyl-4-(1-thio-β-D-galactopyranosyl)but-2-yl]glycine,
Nα-[3-((1-thio-β-D-galactopyranosyl)methyl)norborn-2-yl]glycine,
Nα-[3-(1-thio-β-D-galactopyranosyl)cyclohept-1-yl]glycine,
Nα-[3-(1-thio-α-D-galactopyranosyl)cyclohept-1-yl]glycine,
Nα-[4,4-dimethyl-3-(1-thio-β-D-galactopyranosyl)cyclopent-1-yl]glycine,
Nα-[3-(1-thio-β-D-galactopyranosyl)cyclopent-1-yl]glycine,
Nα-[4-(1-thio-β-D-galactopyranosyl)pent-2-yl]glycine,
Nα-[4,4-dimethyl-3-(1-thio-β-D-galactopyranosyl)cyclohex-1-yl]glycine,
Nα-[3-(1-thio-β-D-galactopyranosyl)cyclohex-1-yl]glycine,
Nα-[5-(1-thio-β-D-galactopyranosyl)-2,2-dimethylcyclohex-1-yl]glycine,
Nβ-[2-(1-thio-β-D-galactopyranosyl)cyclopent-1-yl]-β-alanine,
Nβ-[2-(1-thio-β-D-galactopyranosyl)cyclohex-1-yl]-β-alanine,
Nβ-[4-phenyl-4-(1-thio-β-D-galactopyranosyl)but-2-yl]-β-alanine,
Nβ-[3-((1-thio-β-D-galactopyranosyl)methyl)norborn-2-yl]-β-alanine,
Nβ-[3-(1-thio-β-D-galactopyranosyl)cyclohept-1-yl]-β-alanine,
Nβ-[4,4-dimethyl-3-(1-thio-β-D-galactopyranosyl)cyclopent-1-yl]-β-alanine,
Nβ-[3-(1-thio-β-D-galactopyranosyl)cyclopent-1-yl]-β-alanine,
Nβ-[4-(1-thio-β-D-galactopyranosyl)pent-2-yl]-alanine,
Nβ-[4,4-dimethyl-3-(1-thio-β-D-galactopyranosyl)cyclohex-1-yl]-β-alanine,
Nβ-[3-(1-thio-β-D-galactopyranosyl)cyclohex-1-yl]-β-alanine,
Nβ-[5-(1-thio-β-D-galactopyranosyl)-2,2-dimethylcyclohex-1-yl]-β-alanine,
Nα-[2-(1-thio-β-D-galactopyranosyl)cyclopent-1-yl]-L-leucine,
Nα-[2-(1-thio-β-D-galactopyranosyl)cyclohex-1-yl]-L-leucine,
Nα-[4-phenyl-4-(1-thio-β-D-galactopyranosyl)but-2-yl]-L-leucine,
Nα-[1 -(1-thio-β-D-galactopyranosyl)cyclohept-3-yl]-L-leucine,
Nα-[4,4-dimethyl-3-(1-thio-β-D-galactopyranosyl)cyclopent-1-yl]-L-leucine,
Nα-[3-(1-thio-β-D-galactopyranosyl)cyclopent-1-yl]-L-leucine,
Nα-[4-(1-thio-β-D-galactopyranosyl)pent-2-yl]-L-leucine, Nα-[4,4-dimethyl-3-(1-thio-β-D-galactopyranosyl)
  cyclohex-1-yl]-L-leucine,
Nα-[3-(1-thio-β-D-galactopyranosyl)cyclohex-1-yl]-L-
  leucine,
Nα-[2-(1-thio-β-D-galactopyranosyl)cyclopent-1-yl]-L-
  histidine,
Nα-[2-(1-thio-β-D-galactopyranosyl)cyclohex-1-yl]-L-
  histidine,
Nα-[4-phenyl-4-(1-thio-β-D-galactopyranosyl)but-2-yl]-L-
  histidine,
Nα-[3-(1-thio-β-D-galactopyranosyl)cyclohept-1-yl]-L-
  histidine,
Nα-[4,4-dimethyl-3 -(1-thio-β-D-galactopyranosyl)
  cyclopent-1-yl]-L-histidine,
Nα-[3-(1-thio-β-D-galactopyranosyl)cyclopent-1-yl]-L-
  histidine,
Nα-[4-(1-thio-β-D-galactopyranosyl)pent-2-yl]-L-histidine,
Nα-[4,4-dimethyl-3-(1-thio-β-D-galactopyranosyl)
  cyclohex-1-yl]-L-histidine,
Nα-[3-(1-thio-β-D-galactopyranosyl)cyclohex-1-yl]-L-
  histidine,
Nα-[2-(1-thio-β-D-galactopyranosyl)cyclopent-1-yl]-L-
  tryptophan,
Nα-[2-(1-thio-β-D-galactopyranosyl)cyclohex-1-yl]-L-
  tryptophan,
Nα-[4-phenyl-4-(1-thio-β-D-galactopyranosyl)but-2-yl]-L-
  tryptophan,
Nα-[3-(1-thio-β-D-galactopyranosyl)cyclohept-1-yl]-L-
  tryptophan,
Nα-[4,4-dimethyl-3-(1-thio-β-D-galactopyranosyl)
  cyclopent-1-yl]-L-tryptophan,
Nα-[3-(1-thio-β-D-galactopyranosyl)cyclopent-1-yl]-L-
  tryptophan,
Nα-[4-(1-thio-β-D-galactopyranosyl)pent-2-yl]-L-
  tryptophan,
Nα-[4,4-dimethyl-3-(1-thio-β-D-galactopyranosyl)
  cyclohex-1-yl]-L-tryptophan,
Nα-[3-(1-thio-β-D-galactopyranosyl)cyclohex-1-yl]-L-
  tryptophan,
Nα-[2-(1-thio-β-D-galactopyranosyl)cyclopent-1-yl]-L-
  arginine,
Nα-[2-(1-thio-β-D-galactopyranosyl)cyclohex-1-yl]-L-
  arginine,
Nα-[4-phenyl-4-(1-thio-β-D-galactopyranosyl)but-2-yl]-L-
  arginine,
Nα-[3-(1-thio-β-D-galactopyranosyl)cyclohept-1-yl]-L-
  arginine,
Nα-[4,4-dimethyl-3-(1-thio-β-D-galactopyranosyl)
  cyclopent-1-yl]-L-arginine,
Nα-[3-(1-thio-β-D-galactopyranosyl)cyclopent-1-yl]-L-
  arginine,
Nα-[4-(1-thio-β-D-galactopyranosyl)pent-2-yl]-L-arginine,
Nα-[4,4-dimethyl-3-(1-thio-β-D-galactopyranosyl)
  cyclohex-1-yl]-L-arginine,
Nα-[3-(1-thio-β-D-galactopyranosyl)cyclohex-1-yl]-L-
  arginine,
2,2-dimethyl-4-(methylamino)cyclopent-1-yl 1-thio-β-D-
  galactopyranoside,
2,2-dimethyl-4-(isopropylamino)cyclopent-1-yl 1-thio-β-D-
  galactopyranoside,
2,2-dimethyl-4-(n-propylamino)cyclopent-1-yl 1-thio-β-D-
  galactopyranoside,
2,2-dimethyl-4-((R)-sec-butylamino)cyclopent-1-yl 1-thio-
  β-D-galactopyranoside,
2,2-dimethyl-4-((S)-sec-butylamino)cyclopent-1-yl 1-thio-
  β-D-galactopyranoside,
2,2-dimethyl-4-(pent-3-ylamino)cyclopent-1-yl 1-thio-β-D-
  galactopyranoside,
2,2-dimethyl-4-(n-hexylamino)cyclopent-1-yl 1-thio-β-D-
  galactopyranoside,
2,2-dimethyl-4-(cyclobutylamino)cyclopent-1-yl 1-thio-β-
  D-galactopyranoside,
2,2-dimethyl-4-(3,3-dimethylcyclobut-1-ylamino)
  cyclopent-1-yl 1-thio-β-D-galactopyranoside,
2,2-dimethyl-4-(cyclopentylamino)cyclopent-1-yl 1-thio-β-
  D-galactopyranoside,
2,2-dimethyl-4-(3-methylcyclopent-1-ylamino)cyclopent-1-
  yl 1-thio-β-D-galactopyranoside,
2,2-dimethyl-4-(3,3-dimethylcyclopent-1-ylamino)
  cyclopent-1-yl 1-thio-β-D-galactopyranoside,
2,2-dimethyl-4-(cyclohexylamino)cyclopent-1-yl 1-thio-β-
  D-galactopyranoside,
2,2-dimethyl-4-(3-methylcyclohex-1-ylamino)cyclopent-1-
  yl 1-thio-β-D-galactopyranoside,
2,2-dimethyl-4-(4-methylcyclohex-1-ylamino)cyclopent-1-
  yl 1-thio-β-D-galactopyranoside,
and pharmaceutically acceptable salts thereof.

30. A pharmaceutical composition comprising from 1 to 99 weight percent of a pharmaceutically acceptable carrier and from 1 to 99 weight percent of at least one compound of formula I:

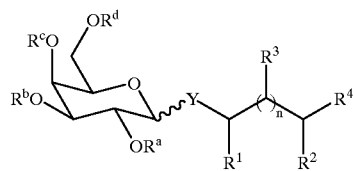

wherein
R$^1$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalk R$^2$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;

R$^3$ is selected from the group consisting of hydrogen, alkyl, substituted alkyl, alkenyl, alkaryl, alkoxyalkyl, aryl, cycloalkyl, cycloalkenyl, heteroaryl, heterocyclic and thioalkoxyalkyl;

or R$^1$ and R$^2$, or R$^1$ and R$^3$, or R$^2$ and R$^3$, or R$^1$, R$^2$ and R$^3$ can be joined, together with the carbon atoms to which R$^1$ and/or R$^2$ and/or R$^3$ are attached, to form a cycloalkyl, cycloalkyl substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, aryloxy, carboxy, carboxyalkyl, cyano, halo, nitro, heteroaryl and trihalomethyl, cycloalkenyl or heterocyclic ring;

R$^4$ is selected from the group consisting of —XR$^5$, —XC(W)R$^6$, —XC(W)X'R$^7$ and —C(W)XR$^8$; wherein W is selected from the group consisting of oxygen, sulfur and NH; and X and X' are each independently selected from the group consisting of oxygen, sulfur and —NR$^9$—, wherein R$^9$ is selected from the group consisting of hydrogen and alkyl; or when R$^4$ is —XR$^5$ and R$^5$ is not hydrogen, X can also be selected from the group consisting of —S(O)— and —SO$_2$—;

R⁵ is selected from the group consisting of hydrogen, alkyl, alkenyl, alkaryl, alkoxyalkyl, aryl, cycloalkyl, cycloalkenyl, heteroaryl, heterocyclic and thioalkoxyalkyl, and when X is —NR⁹—, then R⁹ together with X can form an amino acid; or R⁵ and R¹, or R⁵ and R², or R⁵ and R³ can be joined, together with X of the —XR⁵ group and the carbon atoms to which R¹ and/or R² and/or R³ are attached, to form a heterocyclic ring;

R⁶ is selected from the group consisting of alkyl, alkenyl, alkaryl, alkoxyalkyl, aryl, cycloalkyl, cycloalkenyl, heteroaryl, heterocyclic and thioalkoxyalkyl; or R⁶ and R¹, or R⁶ and R², or R⁶ and R³ can be joined, together with the —XC(W)— moiety of the —XC(W)R⁶ group and the carbon atoms to which R¹ and/or R² and/or R³ are attached, to form a heterocyclic ring;

R⁷ is selected from the group consisting of alkyl, alkenyl, alkaryl, alkoxyalkyl, aryl, cycloalkyl, cycloalkenyl, heteroaryl, heterocyclic and thioalkoxyalkyl; or R⁷ and R¹, or R⁷ and R², or R⁷ and R³ can be joined, together with the —XC(W)X'— moiety of the —XC(W)X'R⁷ group and the carbon atoms to which R¹ and/or R² and/or R³ are attached, to form a heterocyclic ring;

R⁸ is selected from the group consisting of alkyl, alkenyl, alkaryl, alkoxyalkyl, aryl, cycloalkyl, cycloalkenyl, heteroaryl, heterocyclic and thioalkoxyalkyl; or R⁸ and R¹, or R⁸ and R², or R⁸ and R³ can be joined, together with the —C(W)X— moiety of the —C(W)XR⁸ group and the carbon atoms to which R¹, R² and/or R³ are attached, to form a heterocyclic ring;

Y is selected from the group consisting of sulfur, —S(O)— and —S(O)₂—;

R$^a$, R$^b$, R$^c$ and R$^d$ are each independently selected from the group consisting of hydrogen; sulfate; —C(O)R¹⁰, wherein R¹⁰ is selected from the group consisting of alkyl, alkenyl, alkaryl, alkoxyalkyl, aryl, cycloalkyl, cycloalkenyl, heteroaryl, heterocyclic and thioalkoxyalkyl; and —P(O)(OR¹¹)₂, wherein each R¹¹ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl; and n is an integer equal to 0 or 1; or pharmaceutically acceptable salts thereof;

wherein said compound inhibits the binding of a toxin to its receptor, or said compound inhibits the binding of an organism to its cell surface receptor;

aryl, cycloalkyl, cycloalkenyl, heteroaryl, heterocyclic, thioalkoxyalkyl and a linking arm covalently linking the compound of formula I' to the support;

$R^2$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support;

$R^3$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support;

or $R^1$ and $R^2$, or $R^1$ and $R^3$, or $R^2$ and $R^3$, or $R^1$, $R^2$ and $R^3$ can be joined, together with the carbon atoms to which $R^1$ and/or $R^2$ and/or $R^3$ are attached, to form a cycloalkyl, cycloalkyl substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, aryloxy, carboxy, carboxyalkyl, cyano, halo, nitro, heteroaryl and trihalomethyl, cycloalkenyl or heterocyclic ring;

$R^4$ is selected from the group consisting of —$XR^5$, —$XC(W)R^6$, —$XC(W)X'R^7$ and —$C(W)XR^8$; wherein W is selected from the group consisting of oxygen, sulfur and NH; and X and X' are each independently selected from the group consisting of oxygen, sulfur and —$NR^9$—, wherein $R^9$ is selected from the group consisting of hydrogen and alkyl; or when $R^4$ is —$XR^5$ and $R^5$ is not hydrogen, X can also be selected from the group consisting of —S(O)— and —$SO_2$—;

$R^5$ is selected from the group consisting of hydrogen, alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support, and when X is —$NR^9$—, then $R^9$ together with X can form an amino acid; or $R^5$ and $R^1$, or $R^5$ and $R^2$, or $R^5$ and $R^3$ can be joined, together with X of the —$XR^5$ group and the carbon atoms to which $R^1$ and/or $R^2$ and/or $R^3$ are attached, to form a heterocyclic ring;

$R^6$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^6$ and $R^1$, or $R^6$ and $R^2$, or $R^6$ and $R^3$ can be joined, together with the —XC(W)— moiety of the —$XC(W)R^6$ group and the carbon atoms to which $R^1$ and/or $R^2$ and/or $R^3$ are attached, to form a heterocyclic ring;

$R^7$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^7$ and $R^1$, or $R^7$ and $R^2$, or $R^7$ and $R^3$ can be joined, together with the —XC(W)X'— moiety of the —$XC(W)X'R^7$ group and the carbon atoms to which $R^1$ and/or $R^2$ and/or $R^3$ are attached, to form a heterocyclic ring;

$R^8$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^8$ and $R^1$, or $R^8$ and $R^2$ or $R^8$ and $R^3$ can be joined, together with the —C(W)X— moiety of the —$C(W)XR^8$ group and the carbon atoms to which $R^1$, $R^2$ and/or $R^3$ are attached, to form a heterocyclic ring;

Y is selected from the group consisting of sulfur, —S(O)— and —$S(O)_2$—;

$R^a$, $R^b$, $R^c$ and $R^d$ are each independently selected from the group consisting of hydrogen; sulfate; —$C(O)R^{10}$, wherein $R^{10}$ is selected from the group consisting of alkyl, alkenyl, alkaryl, alkoxyalkyl, aryl, cycloalkyl, cycloalkenyl, heteroaryl, heterocyclic, and thioalkoxyalkyl; and —$P(O)(OR^{11})_2$, wherein each $R^{11}$ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl; and a linking arm covalently linking the compound of formula I' to the support; and n is an integer equal to 0 or 1; or pharmaceutically acceptable salts thereof;

with the proviso that only one of $R^1$, $R^2$, $R^3$, $R^5$, $R^6$, $R^7$, $R^8$, $R^a$, $R^b$, $R^c$ and $R^d$ is linked to the support; and with the further proviso that when $R^1$ and $R^2$ are joined, together with the carbon atoms to which $R^1$, $R^2$ and $R^3$ are attached, to form a cyclopentyl ring, $R^3$ is hydrogen, $R^4$ is —$XR^5$, X is oxygen, Y is sulfur and n is 1, then $R^a$, $R^b$, $R^c$, $R^d$ and $R^5$ are neither hydrogen nor a linking arm covalently linking the compound of formula I' to the support.

49. The 1-thiogalactose derivative-containing support of claim 48 wherein the support is a solid support.

50. The 1-thiogalactose derivative-containing support of claim 48 wherein the compound of formula I' is an α-anomer.

51. The 1-thiogalactose derivative-containing support of claim 48 wherein the compound of formula I' is a β-anomer.

52. The 1-thiogalactose derivative-containing support of claim 48 wherein, when n is 0, $R^1$ and $R^2$ are joined, together with the carbon to which they are attached, to form a cycloalkyl ring having 5 to 7 carbon atoms or a cycloalkyl ring having 5 to 7 carbon atoms substituted with 1 to 3 alkyl groups.

53. The 1-thiogalactose derivative-containing support of claim 48 wherein, when n is 1, $R^1$ and $R^2$ are joined, together with the carbon atoms to which $R^1$, $R^2$ and $R^3$ are attached, to form a cycloalkyl ring having 5 to 7 carbon atoms or a cycloalkyl ring having 5 to 7 carbon atoms substituted with 1 to 3 alkyl groups.

54. The 1-thiogalactose derivative-containing support of claim 53 wherein $R^4$ is —$XR^5$, where X is —NH— and $R^5$ is cycloalkyl.

55. The 1-thiogalactose derivative-containing support of claim 48 wherein, when n is 1, $R^2$ and $R^3$ are joined, together with the carbon atoms to which they are attached, to form a norbornene ring.

56. A 1-thiogalactose derivative-containing support comprising a support having covalently bound thereto a plurality of at least one compound of formula I':

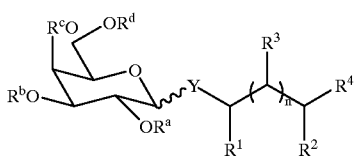

I' wherein
- $R^1$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support;
- $R^2$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support;
- $R^3$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support;
- or $R^1$ and $R^2$, or $R^1$ and $R^3$, or $R^2$ and $R^3$, or $R^1$, $R^2$ and $R^3$ can be joined, together with the carbon atoms to which $R^1$ and/or $R^2$ and/or $R^3$ are attached, to form a cycloalkyl, cycloalkyl substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, aryloxy, carboxy, carboxyalkyl, cyano, halo, nitro, heteroaryl and trihalomethyl, cycloalkenyl or heterocyclic ring;
- $R^4$ is selected from the group consisting of —$XR^5$, —$XC(W)R^6$, —$XC(W)X'R^7$ and —$C(W)XR^8$; wherein W is selected from the group consisting of oxygen, sulfur and NH; and X and X' are each independently selected from the group consisting of oxygen, sulfur and —$NR^9$—, wherein $R^9$ is selected from the group consisting of hydrogen and alkyl; or when $R^4$ is —$XR^5$ and $R^5$ is not hydrogen, X can also be selected from the group consisting of —S(O)— and —$SO_2$—;
- $R^5$ is selected from the group consisting of hydrogen, alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support, and when X is —$NR^9$—, then $R^9$ together with X can form an amino acid; or $R^5$ and $R^1$, or $R^5$ and $R^2$, or $R^5$ and $R^3$ can be joined, together with X of the —$XR^5$ group and the carbon atoms to which $R^1$ and/or $R^2$ and/or $R^3$ are attached, to form a heterocyclic ring;
- $R^6$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^6$ and $R^1$, or $R^6$ and $R^2$, or $R^6$ and $R^3$ can be joined, together with the —XC(W)— moiety of the —$XC(W)R^6$ group and the carbon atoms to which $R^1$ and/or $R^2$ and/or $R^3$ are attached, to form a heterocyclic ring;
- $R^7$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^7$ and $R^1$, or $R^7$ and $R^2$, or $R^7$ and $R^3$ can be joined, together with the —XC(W)X'— moiety of the —$XC(W)X'R^7$ group and the carbon atoms to which $R^1$ and/or $R^2$ and/or $R^3$ are attached, to form a heterocyclic ring;
- $R^8$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^8$ and $R^1$, or $R^8$ and $R^2$, or $R^8$ and $R^3$ can be joined, together with the —C(W)X— moiety of the —$C(W)XR^8$ group and the carbon atoms to which $R^1$, $R^2$ and/or $R^3$ are attached, to form a heterocyclic ring;
- Y is selected from the group consisting of sulfur, —S(O)— and —$S(O)_2$—;
- $R^a$, $R^b$, $R^c$ and $R^d$ are each independently selected from the group consisting of hydrogen; sulfate; —$C(O)R^{10}$, wherein $R^{10}$ is selected from the group consisting of alkyl, alkenyl, alkaryl, alkoxyalkyl, aryl, cycloalkyl, cycloalkenyl, heteroaryl, heterocyclic, and thioalkoxyalkyl; and —$P(O)(OR^{11})_2$, wherein each $R^{11}$ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl; and a linking arm covalently linking the compound of formula I' to the support; and
- n is an integer equal to 0 or 1; or pharmaceutically acceptable salts thereof;
- wherein said compound inhibits the binding of a toxin to its receptor, or said compound inhibits the binding of an organism to its cell surface receptor; and
- with the proviso that only one of $R^1$, $R^2$, $R^3$, $R^5$, $R^6$, $R^7$, $R^8$, $R^a$, $R^b$, $R^c$ and $R^d$ is linked to the support.

57. The 1-thiogalactose derivative-containing support of claim 56 wherein the toxin is heat-labile enterotoxin or cholera toxin.

58. The 1-thiogalactose derivative-containing support of claim 56 wherein the organism is *Vibrio cholerae* or an enterotoxigenic strain of *Escherichia coli*.

59. The 1-thiogalactose derivative-containing support of claim 56 wherein the support is a solid support.

60. The 1-thiogalactose derivative-containing support of claim 56 wherein the compound of formula I' is an α-anomer.

61. The 1-thiogalactose derivative-containing support of claim 56 wherein the compound of formula I' is a β-anomer.

62. The 1-thiogalactose derivative-containing support of claim 56 wherein, when n is 0, $R^1$ and $R^2$ are joined, together with the carbon to which they are attached, to form a cycloalkyl ring having 5 to 7 carbon atoms or a cycloalkyl ring having 5 to 7 carbon atoms substituted with 1 to 3 alkyl groups.

63. The 1-thiogalactose derivative-containing support of claim 56 wherein, when n is 1, $R^1$ and $R^2$ are joined, together with the carbon atoms to which $R^1$, $R^2$ and $R^3$ are attached, to form a cycloalkyl ring having 5 to 7 carbon atoms or a cycloalkyl ring having 5 to 7 carbon atoms substituted with 1 to 3 alkyl groups.

64. The 1-thiogalactose derivative-containing support of claim 63 wherein $R^4$ is —$XR^5$, where X is —NH— and $R^5$ is cycloalkyl.

65. The 1-thiogalactose derivative-containing support of claim 56 wherein, when n is 1, $R^2$ and $R^3$ are joined, together with the carbon atoms to which they are attached, to form a norbornene ring.

66. A pharmaceutical composition comprising from 1 to 99 weight percent of a pharmaceutically acceptable carrier and from 1 to 99 weight percent of a 1-thiogalactose derivative-containing support comprising a support having covalently bound thereto a plurality of at least one compound of formula I':

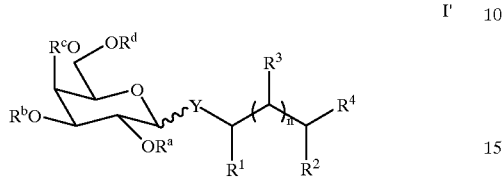

wherein
- $R^1$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support;
- $R^2$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support;
- $R^3$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support;
- or $R^1$ and $R^2$, or $R^1$ and $R^3$, or $R^2$ and $R^3$, or $R^1$, $R^2$ and $R^3$ can be joined, together with the carbon atoms to which $R^1$ and/or $R^2$ and/or $R^3$ are attached, to form a cycloalkyl, cycloalkyl substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, arvloxy, carboxy, carboxyalkyl, cyano, halo, nitro, heteroaryl and trihalomethyl, cycloalkenyl or heterocyclic ring;
- $R^4$ is selected from the group consisting of —$XR^5$, —$XC(W)R^6$, —$XC(W)X'R^7$ and —$C(W)XR^8$; wherein W is selected from the group consisting of oxygen, sulfur and NH; and X and X' are each independently selected from the group consisting of oxygen, sulfur and —$NR^9$—, wherein $R^9$ is selected from the group consisting of hydrogen and alkyl; or when $R^4$ is —$XR^5$ and $R^1$ is not hydrogen, X can also be selected from the group consisting of —S(O)— and —$SO_2$—;
- $R^5$ is selected from the group consisting of hydrogen, alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support, and when X is —$NR^9$—, then $R^9$ together with X can form an amino acid; or $R^5$ and $R^1$, or $R^5$ and $R^2$, or $R^5$ and $R^3$ can be joined, together with X of the —$XR^5$ group and the carbon atoms to which $R^1$ and/or $R^2$ and/or $R^3$ are attached, to form a heterocyclic ring;
- $R^6$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^6$ and $R^1$, or $R^6$ and $R^2$, or $R^6$ and $R^3$ can be joined, together with the —XC(W)— moiety of the —$XC(W)R^6$ group and the carbon atoms to which $R^1$ and/or $R^2$ and/or $R^3$ are attached, to form a heterocyclic ring;
- $R^7$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^7$ and $R^1$, or $R^7$ and $R^2$, or $R^7$ and $R^3$ can be joined, together with the —XC(W)X'— moiety of the —$XC(W)X'R^7$ group and the carbon atoms to which $R^1$ and/or $R^2$ and/or $R^3$ are attached, to form a heterocyclic ring;
- $R^8$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^8$ and $R^1$, or $R^8$ and $R^2$, or $R^8$ and $R^3$ can be joined, together with the —C(W)X— moiety of the —$C(W)XR^8$ group and the carbon atoms to which $R^1$, $R^2$ and/or $R^3$ are attached, to form a heterocyclic ring;
- Y is selected from the group consisting of sulfur, —S(O)— and —$S(O)_2$—;
- $R^a$, $R^b$, $R^c$ and $R^d$ are each independently selected from the group consisting of hydrogen; sulfate; —$C(O)R^{10}$, wherein $R^{10}$ is selected from the group consisting of alkyl, alkenyl, alkaryl, alkoxyalkyl, aryl, cycloalkyl, cycloalkenyl, heteroaryl, heterocyclic, and thioalkoxyalkyl; and —$P(O)(OR^{11})_2$, wherein each $R^{11}$ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl; and a linking arm covalently linking the compound of formula I' to the support; and
- n is an integer equal to 0 or 1; or pharmaceutically acceptable salts thereof;

with the proviso that only one of $R^1$, $R^2$, $R^3$, $R^5$, $R^6$, $R^7$, $R^8$, $R^a$, $R^b$, $R^c$ and $R^d$ is linked to the support; and with the further proviso that when $R^1$ and $R^2$ are joined, together with the carbon atoms to which $R^1$, $R^2$ and $R^3$ are attached, to form a cyclopentyl ring, $R^3$ is hydrogen, $R^4$ is —$XR^5$, X is oxygen, Y is sulfur and n is 1, then $R^a$, $R^b$, $R^c$, $R^d$ and $R^5$ are neither hydrogen nor a linking arm covalently linking the compound of formula I' to the support.

67. The pharmaceutical composition of claim 66 wherein the support is a solid support.

68. The pharmaceutical composition of claim 66 wherein, when n is 0, $R^1$ and $R^2$ are joined, together with the carbon to which they are attached, to form a cycloalkyl ring having 5 to 7 carbon atoms or a cycloalkyl ring having 5 to 7 carbon atoms substituted with 1 to 3 alkyl groups.

69. The pharmaceutical composition of claim 66 wherein, when n is 1, $R^1$ and $R^2$ are joined, together with the carbon atoms to which $R^1$, $R^2$ and $R^3$ are attached, to form a cycloalkyl ring having 5 to 7 carbon atoms or a cycloalkyl ring having 5 to 7 carbon atoms substituted with 1 to 3 alkyl groups.

70. The pharmaceutical composition of claim 69 wherein $R^4$ is —$XR^5$, where X is —NH— and $R^5$ is cycloalkyl.

71. The pharmaceutical composition of claim 66 wherein, when n is 1, $R^2$ and $R^3$ are joined, together with the carbon atoms to which they are attached, to form a norbornene ring.

72. A pharmaceutical composition comprising from 1 to 99 weight percent of a pharmaceutically acceptable carrier and from 1 to 99 weight percent of a 1-thiogalactose derivative-containing support comprising a support having covalently bound thereto a plurality of at least one compound of formula I':

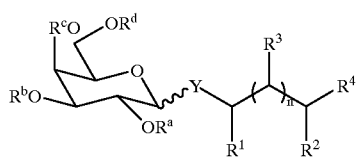

I' wherein
- $R^1$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support;
- $R^2$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support;
- $R^3$ is selected from the group consisting of hydrogen, alkyl, substituted alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support;
- or $R^1$ and $R^2$, or $R^1$ and $R^3$, or $R^2$ and $R^3$, or $R^1$, $R^2$ and $R^3$ can be joined, together with the carbon atoms to which $R^1$ and/or $R^2$ and/or $R^3$ are attached, to form a cycloalkyl, cycloalkyl substituted with from 1 to 3 substituents selected from the group consisting of hydroxy, acyl, acyloxy, alkyl, substituted alkyl, alkylene, alkoxy, alkenyl, alkynyl, amino, aminoacyl, aryl, arvloxy, carboxy, carboxyalkyl, cyano, halo, nitro, heteroaryl and trihalomethyl, cycloalkenyl or heterocyclic ring;
- $R^4$ is selected from the group consisting of —$XR^5$, —$XC(W)R^6$, —$XC(W)X'R^7$ and —$C(W)XR^8$; wherein W is selected from the group consisting of oxygen, sulfur and NH; and X and X' are each independently selected from the group consisting of oxygen, sulfur and —$NR^9$—, wherein $R^9$ is selected from the group consisting of hydrogen and alkyl; or when $R^4$ is —$XR^5$ and $R^5$ is not hydrogen, X can also be selected from the group consisting of —S(O)— and —$SO_2$—;
- $R^5$ is selected from the group consisting of hydrogen, alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support, and when X is —$NR^9$—, then $R^9$ together with X can form an amino acid; or $R^5$ and $R^1$, or $R^5$ and $R^2$, or $R^5$ and $R^3$ can be joined, together with X of the —$XR^5$ group and the carbon atoms to which $R^1$ and/or $R^2$ and/or $R^3$ are attached, to form a heterocyclic ring;
- $R^6$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^6$ and $R^1$, or $R^6$ and $R^2$, or $R^6$ and $R^3$ can be joined, together with the —XC(W)— moiety of the —$XC(W)R^6$ group and the carbon atoms to which $R^1$ and/or $R^2$ and/or $R^3$ are attached, to form a heterocyclic ring;
- $R^7$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^7$ and $R^1$, or $R^7$ and $R^2$, or $R^7$ and $R^3$ can be joined, together with the —XC(W)X'— moiety of the —$XC(W)X'R^7$ group and the carbon atoms to which $R^1$ and/or $R^2$ and/or $R^3$ are attached, to form a heterocyclic ring;
- $R^8$ is selected from the group consisting of alkyl, alkenyl, alkaryl, alkoxyalkyl, aryl, cycloalkyl, cycloalkenyl, heteroaryl, heterocyclic, thioalkoxyalkyl and a linking arm covalently linking the compound of formula I' to the support; or $R^8$ and $R^1$, or $R^8$ and $R^2$, or $R^8$ and $R^3$ can be joined, together with the —C(W)X— moiety of the —$C(W)XR^8$ group and the carbon atoms to which $R^1$, $R^2$ and/or $R^3$ are attached, to form a heterocyclic ring;
- Y is selected from the group consisting of sulfur, —S(O)— and —$S(O)_2$—;
- $R^a$, $R^b$, $R^c$ and $R^d$ are each independently selected from the group consisting of hydrogen; sulfate; —$C(O)R^{10}$, wherein $R^{10}$ is selected from the group consisting of alkyl, alkenyl, alkaryl, alkoxyalkyl, aryl, cycloalkyl, cycloalkenyl, heteroaryl, heterocyclic, and thioalkoxyalkyl; and —$P(O)(OR^{11})_2$, wherein each $R^{11}$ is independently selected from the group consisting of hydrogen, alkyl, alkenyl, alkaryl, alkoxyalkyl, aryl, cycloalkyl, cycloalkenyl, heteroaryl, heterocyclic and thioalkoxyalkyl; and a linking arm covalently linking the compound of formula I' to the support; and
- n is an integer equal to 0 or 1; or pharmaceutically acceptable salts thereof;
- wherein said compound inhibits the binding of a toxin to its receptor, or said compound inhibits the binding of an organism to its cell surface receptor; and
- with the proviso that only one of $R^1$, $R^2$, $R^3$, $R^5$, $R^6$, $R^7$, $R^8$, $R^a$, $R^b$, $R^c$ and $R^d$ is linked to the support.

73. The pharmaceutical composition of claim 72 wherein the toxin is heat-labile enterotoxin or cholera toxin.

74. The pharmaceutical composition of claim 72 wherein the organism is *Vibrio cholerae* or an enterotoxigenic strain of *Escherichia coli*.

75. The pharmaceutical composition of claim 72 wherein the support is a solid support.

76. The pharmaceutical composition of claim 72 wherein, when n is 0, $R^1$ and $R^2$ are joined, together with the carbon to which they are attached, to form a cycloalkyl ring having 5 to 7 carbon atoms or a cycloalkyl ring having 5 to 7 carbon atoms substituted with 1 to 3 alkyl groups.

77. The pharmaceutical composition of claim 72 wherein, when n is 1, $R^1$ and $R^2$ are joined, together with the carbon atoms to which $R^1$, $R^2$ and $R^3$ are attached, to form a cycloalkyl ring having 5 to 7 carbon atoms or a cycloalkyl ring having 5 to 7 carbon atoms substituted with 1 to 3 alkyl groups.

78. The pharmaceutical composition of claim 77 wherein $R^4$ is —$XR^5$, where X is —NH— and $R^5$ is cycloalkyl.

79. The pharmaceutical composition of claim 72 wherein, when n is 1, $R^2$ and $R^3$ are joined, together with the carbon atoms to which they are attached, to form a norbornene ring.

80. A method of ameliorating conditions associated with binding of a toxin to its receptor in an animal which method comprises administering to said animal an effective amount of a pharmaceutical composition of claim 66, wherein the compound of formula I' inhibits the binding of the toxin to its receptor.

81. The method of claim 80 wherein the toxin is heat-labile enterotoxin or cholera toxin.

82. A method of ameliorating conditions associated with binding of a toxin to its receptor in an animal which method comprises administering to said animal an effective amount of a pharmaceutical composition of claim 72, wherein the compound of formula I' inhibits the binding of the toxin to its receptor.

83. The method of claim 82 wherein the toxin is heat-labile enterotoxin or cholera toxin.

84. A method of ameliorating conditions associated with binding of an organism to its cell surface receptors in an animal which method comprises administering to said animal an effective amount of a pharmaceutical composition of claim 66, wherein the compound of formula I' inhibits the binding of the organism to its cell surface receptor.

85. The method of claim 84 wherein the organism is *Vibrio cholerae* or an enterotoxigenic strain of *Escherichia coli.*

86. A method of ameliorating conditions associated with binding of an organism to its cell surface receptors in an animal which method comprises administering to said animal an effective amount of a pharmaceutical composition of claim 72, wherein the compound of formula I' inhibits the binding of the organism to its cell surface receptor.

87. The method of claim 86 wherein the organism is *Vibrio cholerae* or an enterotoxigenic strain of *Escherichia coli.*

* * * * *